(12) United States Patent
Ueno et al.

(10) Patent No.: US 9,080,960 B2
(45) Date of Patent: *Jul. 14, 2015

(54) BIOSENSOR, BIOSENSOR CHIP AND BIOSENSOR DEVICE

(71) Applicant: PANASONIC HEALTHCARE HOLDINGS CO., LTD., Tokyo (JP)

(72) Inventors: Hiroya Ueno, Kadoma (JP); Junji Nakatsuka, Kadoma (JP)

(73) Assignee: PANASONIC HEALTHCARE HOLDINGS CO., LTD., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/512,207

(22) Filed: Oct. 10, 2014

(65) Prior Publication Data

US 2015/0060305 A1    Mar. 5, 2015

Related U.S. Application Data

(63) Continuation of application No. 13/934,766, filed on Jul. 3, 2013, now Pat. No. 8,900,430, which is a continuation of application No. 12/618,084, filed on Nov. 13, 2009, now Pat. No. 8,568,579, which is a (Continued)

(30) Foreign Application Priority Data

Jul. 2, 2002    (JP) .................................. 2002-193547
Oct. 18, 2002   (JP) .................................. 2002-304858

(51) Int. Cl.
*G01N 27/327* (2006.01)
*C12Q 1/00* (2006.01)

(Continued)

(52) U.S. Cl.
CPC .............. *G01N 27/327* (2013.01); *C12Q 1/001* (2013.01); *G01N 27/30* (2013.01); *G01N 27/307* (2013.01); *G01N 27/3271* (2013.01);

(Continued)

(58) Field of Classification Search
CPC ....................... G01N 27/3272; G01N 27/3273
See application file for complete search history.

(56) References Cited

U.S. PATENT DOCUMENTS 3,922,205 A    11/1975    McLean et al.
4,011,746 A    3/1977     Weitz, Jr. et al.

(Continued)

FOREIGN PATENT DOCUMENTS

CA    2296608 A1    2/1999
DE    4100727 A1    7/1992

(Continued)

OTHER PUBLICATIONS

JPO machine-language English language translation of Miyashita JP 11-344460 A, patent published Dec. 14, 1999.*

(Continued)

*Primary Examiner* — Alex Noguerola

(74) *Attorney, Agent, or Firm* — Amster, Rothstein & Ebenstein LLP

(57) ABSTRACT

A biosensor includes a working electrode 101, a counter electrode 102 opposing the working electrode 101, a working electrode terminal 103 and a working electrode reference terminal 10 connected to the working electrode 101 by wires, and a counter electrode terminal 104 connected to the counter electrode 102 by a wire. By employing a structure with at least three electrodes, it is possible to assay a target substance without being influenced by the line resistance on the working electrode side.

16 Claims, 38 Drawing Sheets

Related U.S. Application Data continuation of application No. 12/360,639, filed on Jan. 27, 2009, now Pat. No. 8,388,820, which is a continuation of application No. 10/488,325, filed as application No. PCT/JP03/07593 on Jun. 16, 2003, now Pat. No. 7,540,947.

(51) Int. Cl.
*G01N 27/416* (2006.01)
*G01N 27/30* (2006.01)

(52) U.S. Cl.
CPC ....... *G01N 27/3272* (2013.01); *G01N 27/3273* (2013.01); *G01N 27/416* (2013.01)

(56) References Cited

U.S. PATENT DOCUMENTS

| | | | |
|---|---|---|---|
| 4,013,522 A | | 3/1977 | Nischik et al. |
| 4,227,984 A | | 10/1980 | Dempsey et al. |
| 4,294,115 A | | 10/1981 | Labus |
| 4,326,927 A | | 4/1982 | Stetter et al. |
| 4,627,906 A | | 12/1986 | Gough |
| 4,795,542 A | | 1/1989 | Ross et al. |
| 4,822,474 A | | 4/1989 | Corrado |
| 4,950,378 A | | 8/1990 | Nagata |
| 4,999,582 A | | 3/1991 | Parks et al. |
| 5,120,420 A | | 6/1992 | Nankai |
| 5,217,595 A | | 6/1993 | Smith et al. |
| 5,264,103 A | | 11/1993 | Yoshioka et al. |
| 5,266,179 A | | 11/1993 | Nankai et al. |
| 5,282,950 A | | 2/1994 | Dietze et al. |
| 5,438,271 A | | 8/1995 | White et al. |
| 5,565,085 A | * | 10/1996 | Ikeda et al. ................. 205/777.5 |
| 5,698,083 A | | 12/1997 | Glass |
| 5,746,511 A | | 5/1998 | Eryurek et al. |
| 5,925,021 A | | 7/1999 | Castellano et al. |
| 5,977,757 A | | 11/1999 | Felps |
| 5,985,129 A | | 11/1999 | Gough et al. |
| 5,985,130 A | | 11/1999 | Ikeda et al. |
| 5,986,910 A | | 11/1999 | Nakatsuka |
| 5,997,817 A | | 12/1999 | Crismore et al. |
| 6,144,869 A | | 11/2000 | Berner et al. |
| 6,176,989 B1 | | 1/2001 | Shi |
| 6,233,471 B1 | | 5/2001 | Berner et al. |
| 6,272,364 B1 | | 8/2001 | Kurnik |
| 6,290,827 B1 | | 9/2001 | Johansson |
| 6,299,757 B1 | | 10/2001 | Feldman et al. |
| 6,326,160 B1 | | 12/2001 | Dunn et al. |
| 6,341,232 B1 | | 1/2002 | Conn et al. |
| 6,391,643 B1 | | 5/2002 | Chen et al. |
| 6,473,018 B2 | | 10/2002 | Ueno et al. |
| 6,599,406 B1 | | 7/2003 | Kawanaka et al. |
| 7,232,510 B2 | | 6/2007 | Miyazaki et al. |
| 7,326,384 B2 | | 2/2008 | Oka et al. |
| 7,418,285 B2 | | 8/2008 | Ghesquiere et al. |
| 7,540,947 B2 | | 6/2009 | Ueno et al. |
| 7,601,299 B2 | | 10/2009 | Beaty et al. |
| 7,678,261 B2 | | 3/2010 | Bae et al. |
| 7,695,600 B2 | | 4/2010 | Ho et al. |
| 7,718,439 B2 | | 5/2010 | Groll |
| 8,142,629 B2 | | 3/2012 | Miyazaki et al. |
| 8,206,565 B2 | | 6/2012 | Groll et al. |
| 8,231,768 B2 | | 7/2012 | Ueno et al. |
| 8,388,820 B2 | | 3/2013 | Ueno et al. |
| 8,496,794 B2 | | 7/2013 | Ueno et al. |
| 8,568,579 B2 | | 10/2013 | Ueno et al. |
| 8,574,423 B2 | | 11/2013 | Ueno et al. |
| 8,888,974 B2 | | 11/2014 | Ueno et al. |
| 8,888,975 B2 | | 11/2014 | Ueno et al. |
| 8,900,430 B2 | | 12/2014 | Ueno et al. |
| 2002/0026110 A1 | | 2/2002 | Parris et al. |
| 2003/0168335 A1 | | 9/2003 | Rankin et al. |
| 2003/0204313 A1 | | 10/2003 | Ou-Yang et al. |
| 2004/0106190 A1 | | 6/2004 | Yang et al. |
| 2005/0016845 A1 | | 1/2005 | Groll et al. |
| 2005/0016846 A1 | | 1/2005 | Groll et al. |
| 2005/0279647 A1 | | 12/2005 | Beaty |
| 2010/0140087 A1 | | 6/2010 | Ueno et al. |
| 2012/0135508 A1 | | 5/2012 | Burke et al. |
| 2012/0228160 A1 | | 9/2012 | Ueno et al. |
| 2012/0234677 A1 | | 9/2012 | Ueno et al. |

FOREIGN PATENT DOCUMENTS

| | | | | |
|---|---|---|---|---|
| DE | 198 42 735 | | 3/2000 | |
| DE | 94 22 381 U1 | | 12/2000 | |
| EP | 0471986 A2 | | 2/1992 | |
| EP | 0 775 897 B1 | | 5/1997 | |
| EP | 1 024 358 A1 | | 8/2000 | |
| EP | 1024358 A1 | | 8/2000 | |
| EP | 1 582 864 A1 | | 10/2005 | |
| GB | 1448715 A | | 9/1976 | |
| GB | 2 229 005 | | 9/1990 | |
| JP | 8 504953 | | 5/1996 | |
| JP | 2704046 | | 1/1998 | |
| JP | 11-154833 | | 6/1999 | |
| JP | 11-344460 A | * | 12/1999 | ........... G01N 27/327 |
| JP | 2001 215208 A | | 8/2001 | |
| JP | 2001 330581 A | | 11/2001 | |
| JP | 2002 168821 A | | 6/2002 | |
| WO | 94 29705 | | 12/1994 | |
| WO | WO 9429705 A1 | | 12/1994 | |
| WO | WO 9504272 A1 | | 2/1995 | |
| WO | 99 05516 | | 2/1999 | |
| WO | 99 05516 A1 | | 2/1999 | |
| WO | WO 9953301 A1 | | 10/1999 | |
| WO | WO 0064533 A1 | | 11/2000 | |
| WO | WO 0171328 A1 | | 9/2001 | |
| WO | 02 44705 A1 | | 6/2002 | |
| WO | WO 03091717 A1 | | 11/2003 | |

OTHER PUBLICATIONS

U.S. Office Action mailed Nov. 30, 2012 issued in corresponding U.S. Appl. No. 13/481,413.
United States Office Action, issued in U.S. Appl. No. 12/399,444, dated Mar. 13, 2012.
German Office Action, with English translation thereof only, issued in German Patent Application No. 103 92 159.1, dated Aug. 2, 2010.
German Search Report, issued in German Patent Application No. 103 92 159.1, dated Dec. 29, 2011.
Peng Jin., et al., "Glucose Sensing Based on Interdigitated Array Microelectrode", Analytical Sciences, Jul. 2001, p. 841-846, vol. 17, The Japan Society for Analytical Chemistry.
Jan C. Myland, et al., "Uncompensated Resistance. 1. The Effect of Cell Geometry", Analytical Chemistry, Sep. 1, 2000, p. 3972-3980, vol. 72 No. 17, American Chemical Society.
Keith B. Oldham, et al., "Uncompensated Resistance. 2. The Effect of Reference Electrode Nonideality", Analytical Chemistry, Sep. 1, 2000, p. 3981-3988, vol. 72, No. 17, American Chemical Society.
Eskil Sahlin, et al., "Miniaturized Electrochemical Flow Cells", Analytical Chemistry, Feb. 15, 2003, p. 1031-1036, vol. 75 No. 4, American Chemical Society.
Reza K. Shervedani, et al., "A novel method for glucose determination based on electrochemical impedance spectroscopy using glucose oxidase self-assembled biosensor", Bioelectrochemistry, 2006, p. 201-208, vol. 69, Elsevier B.V.
Zhu. et al. "Fabrication and characterization of glucose sensors based on a microarray H2O2 electrode", Biosensors & Bioelectronrcs, 1994, p. 295-300, vol. 9, Elsevier Science, Ltd.
Notice of Allowance, issued in U.S. Appl. No. 13/481,413, dated Apr. 24, 2013.
German Office Action dated May 5, 2014 with English translation (German patent application No. 10394377.3).
German Office Action dated Mar. 27, 2014 with English translation (German patent application No. 10397002.9).
German Office Action dated May 5, 2014 with English translation (German patent application No. 10397003.7).

(56) References Cited

OTHER PUBLICATIONS

Wang, J., "Portable electrochemical systems," in Trends in Analytical Chemistry, vol. 21, No. 4, 2002, pp. 226-232.
Notice of Allowance, issued in U.S. Appl. No. 13/934,766, dated Jul. 23, 2014.
Notice of Allowance, issued in U.S. Appl. No. 13/934,847, dated Jul. 21, 2014.
Notice of Allowance, issued in U.S. Appl. No. 13/934,915, dated Aug. 5, 2014.
Gamry Industries, PCA Potentiostat/Galvanostat/ZRA Operator's Manual, Jun. 2, 1999.
G. Krucker, Elektronische Signalverarbeitung, 1st Ed., Summer 2000, pp. 1-4, Figs. 1-7.
R. Kakerow, et al., Low-Power Single-Chip CMOS Potentiostat, The 8th International Conference on Solid-State Sensor and Actuators and Eurosensors IX, Stockholm, Sweden, Jun. 1995.
Koopal, et al., "Third-Generation Glucose Biosensor Incorporated in a Conducting Printing Ink," Sensors & Actuators B, vol. 18-19 (1994), pp. 166-170.
Langereis, et al., "Using a Single Structure for Three Sensor Operations and Two Actuator Operations," Sensors & Actuators B, vol. 53 (1998), pp. 197-203.
Ruger, et al., "Glucose and Ethanol Biosensors Based on Thick-Film Technology," Sensors & Actuators B, vol. 4 (1991), pp. 267-271.
Buttner, et al., "An Integrated Amperometric Microsensor," Sensors & Actuators B, vol. 1 (1990), pp. 303-307.
Steinschaden, et al., "Miniaturised Thin Film Conductometric Biosensors with High Dynamic Range and High Sensitivity," Sensors & Actuators B, vol. 44 (1997), pp. 365-369.
Kell, et al., "Conductimetric and Impedimetric Devices," in Biosensors: A Practical Approach (A.E.G. Cass ed., 1990), pp. 125-154.
Palleschi, et al., "Sensor Fabrication," in in Vivo Chemical Sensors: Recent Developments (Alcock et al. ed., 1993), pp. 153-156.
Yi-Feng Tu, et al., "The Fabrication and Optimization of the Disposable Amperometric Biosensor," Sensors & Actuators B, 80 (2001), pp. 101-105.
Non-Final Office Action for U.S. Appl. No. 14/508,780 dated Jan. 23, 2015.
Non-Final Office Action for U.S. Appl. No. 14/509,802 dated Jan. 23, 2015.
Non-Final Office Action for U.S. Appl. No. 14/512,817 dated Jan. 26, 2015.
Non-Final Office Action for U.S. Appl. No. 14/508,668 dated Dec. 10, 2014.
Non-Final Office Action for U.S. Appl. No. 14/509,728 dated Feb. 5, 2015.
Non-Final Office Action for U.S. Appl. No. 14/512,243 dated Feb. 10, 2015.
Notice of Allowance for U.S. Appl. No. 14/508,668 dated Mar. 23, 2015.
Notice of Allowance for U.S. Appl. No. 14/508,780 dated Mar. 3, 2015.
Notice of Allowance for U.S. Appl. No. 14/509,728 dated Mar. 13, 2015.
Non-Final Office Action for U.S. Appl. No. 14/509,762 dated Feb. 20, 2015.
Notice of Allowance for U.S. Appl. No. 14/509,762 dated Mar. 27, 2015.
Non-Final Office Action for U.S. Appl. No. 14/512,157 dated Mar. 6, 2015.
Notice of Allowance for U.S. Appl. No. 14/512,157 dated Apr. 15, 2015.
Notice of Allowance for U.S. Appl. No. 14/509,802 dated Mar. 5, 2015.
Non-Final Office Action for U.S. Appl. No. 14/512,227 dated Mar. 5, 2015.
Notice of Allowance for U.S. Appl. No. 14/512,227 dated Apr. 24, 2015.
Notice of Allowance for U.S. Appl. No. 14/512,243 dated Mar. 3, 2015.
Non-Final Office Action for U.S. Appl. No. 14/512,781 dated Mar. 13, 2015.
Notice of Allowance for U.S. Appl. No. 14/512,781 dated Apr. 20, 2015.
Notice of Allowance for U.S. Appl. No. 14/512,817 dated Mar. 17, 2015.
Non-Final Office Action for U.S. Appl. No. 14/512,838 dated Feb. 13, 2015.
Notice of Allowance for U.S. Appl. No. 14/512,838 dated Apr. 15, 2015.

\* cited by examiner

BIOSENSOR, BIOSENSOR CHIP AND BIOSENSOR DEVICE

CROSS REFERENCE TO RELATED APPLICATIONS

This application is a continuation of U.S. application Ser. No. 13/934,766, filed on Jul. 3, 2013, now U.S. Pat. No. 8,900,430, which is a continuation of U.S. application Ser. No. 12/618,084, filed on Nov. 13, 2009, now U.S. Pat. No. 8,568,579, which is a continuation of U.S. application Ser. No. 12/360,639, filed on Jan. 27, 2009, now U.S. Pat. No. 8,388,820, which is a continuation of U.S. application Ser. No. 10/488,325, filed on Mar. 2, 2004, now U.S. Pat. No. 7,540,947, which is a U.S. National Phase under 35 U.S.C. §371 of International Application No. PCT/JP2003/007593, filed on Jun. 16, 2003, claiming priority of Japanese Patent Application Nos. JP 2002-193547, filed on Jul. 2, 2002, and JP 2002-304858, filed on Oct. 18, 2002, the entire contents of each of which are hereby incorporated by reference.

TECHNICAL FIELD

The present invention relates to a biosensor and a biosensor device for electronically detecting the binding reaction of a biological substance such as an oligonucleotide, an antigen, an enzyme, a peptide, an antibody, a DNA fragment, an RNA fragment, glucose, lactic acid, or cholesterol.

BACKGROUND ART

Recently, the use of biosensing instruments using disposable sample pieces has been increasing each year, and it is expected to enable simple and quick assay and analysis of a particular component in a biological body fluid such as blood, plasma, urine, or saliva, or the whole set of proteins created in a cell at a certain point in time, i.e., a proteome. Moreover, individually-tailored medical treatments, in which individuals are treated and administered medicines according to their SNP (acronym for Single Nucleotido Polymorphism) information, are expected to be put into practice in the future by genetic diagnosis using disposable DNA chips.

A conventional biosensor device for detecting the grape sugar level, i.e., the blood glucose level, of a blood sample described in Japanese Patent Application No. 11-509644 will now be described. Note that the term "biosensor" as used herein refers to a disposable portion including a detection section for detecting a biological substance, the term "biosensor chip" refers to a disposable portion including a biosensor, a measurement circuit, etc., mounted on a substrate. Moreover, the term "biosensor device" refers to the entire device including a biosensor or a biosensor chip together with an analysis circuit and other parts.

FIG. 45 is a plan view illustrating the structure of a conventional biosensor. A biosensor 1122 illustrated in the figure includes a working electrode (anode) 1101, and a counter electrode (cathode) 1102 opposing the working electrode 1101, and an assay reagent (not shown) made of an enzyme, a mediator, etc., corresponding to the assayed component is applied on the working electrode 1101 and the counter electrode 1102. The working electrode 1101 is connected to a working electrode terminal 1103 via a conductive line having a line resistance Rp1. Similarly, the counter electrode 1102 is connected to a counter electrode terminal 1104 via a conductive line having a line resistance Rm1.

FIG. 43 is a circuit diagram illustrating a portion of a conventional biosensor device. As illustrated in the figure, the conventional biosensor device has a structure in which the working electrode terminal 1103 and the counter electrode terminal 1104 of the biosensor 1122 illustrated in FIG. 45 are connected to a measurement circuit 1123. For example, the measurement circuit 1123 includes a base voltage source 1117, a counter electrode voltage application section 1106, a working electrode voltage application section 1105 having an ammeter, and a signal processing circuit 1121. In the conventional biosensor device, a working electrode base voltage Vpr1 generated from the base voltage source 1117 is impedance-converted by the working electrode voltage application section 1105, and then a working electrode terminal voltage Vp1 is supplied from the working electrode voltage application section 1105 to the working electrode terminal 1103. At this time, the following expression holds.

$$Vp1 = Vpr1 \quad (1)$$

Vp1 and Vpr1 in Expression (1) represent potential or voltage values. This also applies to Vm1 and Vmr below.

Moreover, a counter electrode base voltage Vmr1 generated from the base voltage source 1117 is impedance-converted by the counter electrode voltage application section 1106, and then a counter electrode terminal voltage Vm1 is supplied from the counter electrode voltage application section 1106 to the counter electrode terminal 1104. At this time, the following expression holds.

$$Vm1 = Vmr1 \quad (2)$$

The value of the current flowing out to the working electrode terminal 1103 is measured by the working electrode voltage application section 1105, and a working electrode current level signals 1120 indicating the measurement result is supplied to the signal processing circuit 1121. The conventional biosensor device calculates the concentration of the assayed component based on the measured current level, and performs a result displaying operation, or the like. Then, Expression (3) below holds, where Vf1 is the electrode application voltage between the working electrode terminal 1103 and the counter electrode terminal 1104.

$$Vf1 = Vpr1 - Vmr1 \quad (3)$$

Moreover, Vf is the sensor application voltage between the working electrode 1101 and the counter electrode 1102. Furthermore, when the blood sample is dripped onto the biosensor 1122, a charge according to the grape sugar level thereof is generated at the working electrode 1101 and the counter electrode 1102, whereby a current flows between the electrodes. Then, the following expression holds, where If1 is the current flowing on the working electrode 1101 side, and If2 is the current flowing on the counter electrode 1102 side.

$$If1 = If2 \quad (4)$$

The grape sugar level, i.e., the blood glucose level, is obtained by measuring the current If1 by the measurement circuit 1123.

FIG. 44 is a circuit diagram illustrating the conventional biosensor device including specific circuit configuration examples of the working electrode voltage application section 1105 and the counter electrode voltage application section 1106. As illustrated in the figure, the working electrode voltage application section 1105 has a circuit configuration in which a feedback resistance Rf is negatively fed back to an operational amplifier, and the counter electrode voltage application section 1106 has an operational amplifier in a null-amplifier configuration, i.e., a buffer circuit configuration, thereby realizing the function described above.

FIG. 46 is a plan view illustrating the structure of a biosensor chip 1124 in the conventional biosensor device illustrated in FIG. 44. In this example, only one pair of the biosensor 1122 and the measurement circuit 1123 is formed on the same substrate.

Moreover, in the conventional biosensor device illustrated in FIG. 43, when the biosensor 1122 measures the blood glucose level, the following expression holds for the electrode application voltage Vf1 and the sensor application voltage Vf, which is the voltage difference between a working electrode voltage Vp and a counter electrode voltage Vm, due to the presence of the conductive line on the working electrode side having the line resistance Rp1 and the conductive line on the counter electrode having the line resistance Rm1.

$$Vf = Vf1 - (Rp1 \cdot If1 + Rm1 \cdot If2) \quad (5)$$

Moreover, for the current If1 flowing on the working electrode 1101 side and the current If2 flowing on the counter electrode 1102 side, the following expression holds based on the Kirchhoff's law.

$$If1 = If2 \quad (6)$$

Substituting Expression (3) and Expression (6) into Expression (5) and rearranging the expression yields the following expression.

$$Vf = (Vpr1 - Vmr1) - (Rp1 + Rm1) \cdot If1 \quad (7)$$

Therefore, it can be seen that the electrode application voltage (Vpr1−Vmr1) supplied from the measurement circuit 1123 to the biosensor 1122 drops by (Rp1+Rm1)·If1 to be equal to the sensor application voltage Vf.

As described above, with the conventional biosensor device, it is possible to easily assay the glucose level in blood.

PROBLEMS TO BE SOLVED BY THE INVENTION

The current If1 caused by the charge generated from the assay reagent is as shown in the following expression with respect to the grape sugar level Q and the sensor application voltage Vf.

$$If1 = f\{Q, Vf\} \quad (8)$$

Therefore, substituting Expression (4) into Expression (3) yields the following expression.

$$If1 = f\{Q, (Vpr1 - Vmr1) - (Rp1 + Rm1) \cdot If1\} \quad (9)$$

Thus, there was a problem in that the potential drop caused by the line resistance Rp1 of the conductive line of the working electrode 1101 and the line resistance Rm1 of the conductive line of the counter electrode 1102 introduces an error in the current If1, thereby causing an error in the final blood glucose level measured by the biosensor device.

In the prior art, a low-resistance noble metal material such as platinum (Pt), gold (Au), or silver (Ag), is used for the conductive line in order to solve the problem. However, this causes another problem that it makes the biosensor 1122 expensive. Since the biosensor portion is basically disposable, it should desirably be as inexpensive as possible. Therefore, there is a strong demand for novel means for reducing the line resistance.

In addition, when the biosensor device is formed as the biosensor chip 1124, a microfabrication technique is used for forming the conductive lines. Moreover, it is speculated that biosensor chips will be further miniaturized in the future. Then, the line resistance will be further increased to cause substantial errors, significantly lowering the assay precision of the biosensor device.

An object of the present invention is to solve the problems in the prior art as described above, and to provide a biosensor and a biosensor device capable of performing an assay without being influenced by the line resistance of a conductive line.

DISCLOSURE OF THE INVENTION

A biosensor of the present invention includes: a working electrode to be in contact with an assayed fluid during an assay; a counter electrode to be in contact with the assayed fluid during an assay, the counter electrode opposing the working electrode with an interval therebetween for allowing a flow of the assayed fluid; a working electrode terminal connected to the working electrode; a counter electrode terminal connected to the counter electrode; and a reference terminal connected to one or both of the working electrode and the counter electrode, through which substantially no current flows during an assay.

In this structure, the reference terminal is provided, whereby it is possible to assay an assayed fluid without being influenced by the resistance between the working electrode and the working electrode terminal or the resistance between the counter electrode and the counter electrode terminal, thus realizing a biosensor capable of performing a high-precision assay.

A biological substance or a microorganism that changes a state of a substance contained in the assayed fluid may be immobilized on at least one of the working electrode and the counter electrode. Then, it is possible to electrically detect a change in the assayed fluid through, for example, a catalytic reaction of an enzyme, an antigen-antibody reaction, a binding reaction between genes, or the like. Thus, it is possible to perform a more detailed assay than with an assay using fluorescence.

The reference terminal may be connected to only one of the working electrode and the counter electrode. Then, it is possible to realize a high-precision assay with fewer components, as compared with a case where the reference terminal is provided both for the working electrode and for the counter electrode. Therefore, the biosensor is particularly effective when a reduction in the manufacturing cost or a reduction in the area is required.

The biosensor may further include: a first line connecting the working electrode to the working electrode terminal; a second line connecting the working electrode or the counter electrode to the reference terminal; and a third line connecting the counter electrode to the counter electrode terminal. Then, it is possible to realize a high-precision assay by appropriately designing the pattern of these lines.

The reference terminal may include: a working electrode reference terminal connected to the working electrode; and a counter electrode reference terminal connected to the counter electrode. Then, it is possible to perform an assay with a higher precision than in a case where the reference terminal is provided only for one of the working electrode and the counter electrode.

The biosensor may further include: a fourth line connecting the working electrode to the working electrode terminal; a fifth line connecting the working electrode to the working electrode reference terminal; a sixth line connecting the counter electrode to the counter electrode reference terminal; and a seventh line connecting the counter electrode to the counter electrode terminal, wherein at least two of the fourth line, the fifth line, the sixth line and the seventh line are provided in different wiring layers so as to at least partially overlap each other as viewed from above. Then, it is possible to reduce the circuit area as compared with a case where all the lines are provided in the same wiring layer.

The first line and the second line may be provided in different wiring layers. Then, it is possible to reduce the circuit area by, for example, arranging the lines so as to overlap each other.

Also when the second line and the third line are provided in different wiring layers, it is possible to reduce the circuit area.

The working electrode, the counter electrode, the reference terminal, the working electrode terminal, the counter electrode terminal, the first line, the second line and the third line may be provided on a substrate; and one of the working electrode terminal and the counter electrode terminal may be provided on a reverse surface of the substrate. Then, it is possible to ensure an even larger wiring area, whereby it is possible to bring the resistance closer to the ideal value of 0Ω.

Moreover, the working electrode terminal and the counter electrode terminal may be provided in different wiring layers.

The third line may be provided so as to extend across a plurality of wiring layers.

Moreover, in a case where the reference terminal is connected to only one of the working electrode and the counter electrode, the counter electrode may have a generally-circular shape; and a portion of an inner periphery of the working electrode may be circular with a substantially constant distance from the counter electrode. Then, it is possible to make the reaction of the assayed fluid uniform, while the electric field acting upon the first and counter electrodes is made uniform, thereby further improving the assay precision.

Alternatively, the working electrode may have a generally-circular shape; and a portion of an inner periphery of the counter electrode may be circular with a substantially constant distance from the working electrode. Also in such a case, it is possible to make the reaction of the assayed fluid uniform, while the electric field acting upon the first and counter electrodes is made uniform, thereby further improving the assay precision.

A plurality of the working electrodes may be provided; and the counter electrodes, each opposing one of the working electrodes, may be integrated together. Then, it is possible to reduce the number of electrodes, thus reducing the manufacturing steps and the manufacturing cost. Moreover, since the cross-sectional area of the line connected to the counter electrode terminal can be increased, whereby it is possible to reduce the line resistance on the counter electrode terminal side.

A plurality of the counter electrodes may be provided; and the working electrodes, each opposing one of the working electrodes, may be integrated together. Also in such a case, it is possible to reduce the number of electrodes, thus reducing the manufacturing cost.

A cross-sectional area of the third line may be greater than that of the first line. Then, the resistance of the third line can be brought closer to the ideal value of 0Ω.

A biosensor chip of the present invention includes: a biosensor including: a working electrode to be in contact with an assayed fluid during an assay; a counter electrode to be in contact with the assayed fluid during an assay, the counter electrode opposing the working electrode with an interval therebetween for allowing a flow of the assayed fluid; a sensor section for holding the assayed fluid; a working electrode terminal connected to the working electrode; a counter electrode terminal connected to the counter electrode; and a reference terminal connected to one or both of the working electrode and the counter electrode, through which substantially no current flows during an assay, the biosensor being provided on a substrate; and a measurement circuit connected to the biosensor and provided on a substrate.

In this structure, the reference terminal is connected to one or both of the working electrode and the counter electrode, whereby it is possible to assay an assayed substance in the assayed fluid irrespective of the resistance value between the working electrode and the working electrode terminal or the resistance value between the counter electrode and the counter electrode terminal. Thus, it is possible to perform a high-precision assay.

A biological substance or a microorganism that changes a state of a substance contained in the assayed fluid may be immobilized on at least one of the working electrode and the counter electrode. Then, it is possible to realize a quick and detailed assay.

The reference terminal may be connected to only one of the working electrode and the counter electrode. Then, it is possible to realize a high-precision assay with fewer components.

For example, the reference terminal may be connected to the working electrode; and the measurement circuit may include: a working electrode voltage application section connected to the working electrode terminal and having an ammeter; a working electrode potential reference circuit connected to the reference terminal; a counter electrode voltage application section connected to the counter electrode terminal; a base voltage source for supplying a base voltage to each of the working electrode potential reference circuit and the counter electrode voltage application section; and a signal processing circuit for processing a current level signal output from the working electrode voltage application section according to a level of a current flowing through the working electrode terminal during an assay.

In such a case, it is preferred, for performing a high-precision assay, that the working electrode potential reference circuit generates a signal so that a voltage applied to the reference terminal is substantially equal to the base voltage supplied to the working electrode potential reference circuit during an assay.

The reference terminal may be connected to the counter electrode; and the measurement circuit may include: a working electrode voltage application section connected to the working electrode terminal; a counter electrode voltage application section connected to the counter electrode terminal and having an ammeter; a counter potential reference circuit connected to the reference terminal; a base voltage source for supplying a base voltage to each of the counter electrode potential reference circuit and the working electrode voltage application section; and a signal processing circuit for processing a current level signal output from the counter electrode voltage application section according to a level of a current flowing through the counter electrode terminal during an assay.

In such a case, it is preferred that the counter electrode potential reference circuit generates a signal so that a voltage applied to the reference terminal is substantially equal to the base voltage supplied to the counter electrode potential reference circuit during an assay.

The reference terminal may be connected to the working electrode; and the measurement circuit may include: a working electrode voltage application section connected to the working electrode terminal and the reference terminal and having an ammeter; a counter electrode voltage application section connected to the counter electrode terminal; a base voltage source for supplying a base voltage to each of the working electrode voltage application section and the counter electrode voltage application section; and a signal processing circuit for processing a current level signal output from the working electrode voltage application section according to a level of a current flowing through the working electrode terminal during an assay. Then, it is possible to assay an assayed substance without providing the working electrode potential reference circuit.

The reference terminal may be connected to the counter electrode; and the measurement circuit may include: a working electrode voltage application section connected to the working electrode terminal; a counter electrode voltage application section connected to the counter electrode terminal and the reference terminal and having an ammeter; a base voltage source for supplying a base voltage to each of the counter electrode voltage application section and the working electrode voltage application section; and a signal processing circuit for processing a current level signal output from the counter electrode voltage application section according to a level of a current flowing through the counter electrode terminal during an assay. Then, it is possible to assay an assayed substance without providing the counter potential reference circuit.

A working electrode reference terminal connected to the working electrode and a counter electrode reference terminal connected to the counter electrode may be included. Then, it is possible to improve the assay precision as compared with a case where only the working electrode reference terminal or only the counter electrode reference terminal is provided.

The measurement circuit may include: a working electrode voltage application section connected to the working electrode terminal and the working electrode reference terminal; a counter electrode voltage application section connected to the counter electrode terminal and the counter electrode reference terminal; a base voltage source for supplying a base voltage to each of the counter electrode voltage application section and the working electrode voltage application section; and a signal processing circuit for processing at least one of a first current level signal output from the working electrode voltage application section according to a level of a current flowing through the working electrode terminal and a second current level signal output from the counter electrode voltage application section according to a level of a current flowing through the counter electrode terminal, during an assay.

In such a case, especially if the signal processing circuit processes both the first current level signal and the second current level signal, it is possible to perform an assay by using two current level signals, thereby further improving the assay precision.

The substrate on which the biosensor is provided and the substrate on which the measurement circuit is provided may be the same substrate. Then, it is possible to simplify the manufacturing process.

The biosensor chip may further include a common substrate; and the substrate on which the biosensor is provided and the substrate on which the measurement circuit is provided may be mounted on the common substrate. Then, it is possible to manufacture a biosensor chip even in a case where the substrate of the measurement circuit reacts with the biological substance or the reagent immobilized on the first and counter electrodes, or in a case where lines of the measurement circuit and lines of the biosensor cannot be integrated together into common lines, for example.

The substrate on which the biosensor is provided and the substrate on which the measurement circuit is provided may be stacked on each other. Then, it is possible to further reduce the area of the biosensor chip while reducing the manufacturing cost.

A plurality of the biosensors may be provided on the same substrate, and at least two of the biosensors may be connected to the same measurement circuit; and a switch for turning ON/OFF a connection between each of the biosensors and the measurement circuit may be further provided between the working electrode terminal of the biosensor and the measurement circuit, between the reference terminal of the biosensor and the measurement circuit, and between the counter electrode terminal of the biosensor and the measurement circuit. Then, it is possible to reduce the number of measurement circuits required, whereby it is possible to further reduce the chip area.

A plurality of the biosensors may be provided on the same substrate, and the sensor sections of two of the biosensors may be provided adjacent to each other. Then, it is possible to perform a plurality of assays at the same time, while requiring a very small amount of sample.

A biosensor device of the present invention may include: a biosensor including: a working electrode to be in contact with an assayed fluid during an assay; a counter electrode to be in contact with the assayed fluid during an assay, the counter electrode opposing the working electrode with an interval therebetween for allowing a flow of the assayed fluid; a sensor section for holding the assayed fluid; a working electrode terminal connected to the working electrode; a counter electrode terminal connected to the counter electrode; and a reference terminal connected to one or both of the working electrode and the counter electrode, through which substantially no current flows during an assay, the biosensor being provided on a substrate; and a measurement circuit connected to the biosensor and provided on a substrate, wherein the biosensor device has a function of assaying a concentration of an assayed substance contained in the assayed fluid from one or both of a value of a current flowing through the working electrode terminal and a value of a current flowing through the counter electrode terminal during an assay. Then, it is possible to assay the target substance more quickly and with a higher precision over the prior art.

The reference terminal may be connected only to one of the working electrode and the counter electrode. Then, it is possible to realize an assay with a higher precision over the prior art, while reducing the number of components as compared with a case where the reference terminal is provided both for the working electrode and for the counter electrode.

The reference terminal may include: a working electrode reference terminal connected to the working electrode; and a counter electrode reference terminal connected to the counter electrode; and the measurement circuit may include: a working electrode voltage application section connected to the working electrode terminal and the working electrode reference terminal; a counter electrode voltage application section connected to the counter electrode terminal and the counter electrode reference terminal; a base voltage source for supplying a base voltage to each of the counter electrode voltage application section and the working electrode voltage application section; and a signal processing circuit for processing at least one of a first current level signal output from the working electrode voltage application section according to a level of a current flowing through the working electrode terminal and a second current level signal output from the counter electrode voltage application section according to a level of a current flowing through the counter electrode terminal, during an assay. Then, it is possible to perform an assay without being influenced by the resistance between the working electrode and the working electrode terminal or the resistance between the counter electrode and the counter electrode terminal, whereby it is possible to improve the assay precision as compared with a case where the reference terminal is connected to only one of the working electrode and the counter electrode.

It is preferred, for an accurate assay, that a voltage applied to the working electrode reference terminal is substantially equal to the base voltage supplied to the working electrode voltage application section during an assay; and a voltage applied to the counter electrode reference terminal is substantially equal to the base voltage supplied to the counter electrode voltage application section during an assay.

The biosensor device may further include a circuit connected to the measurement circuit for analyzing a signal output from the measurement circuit. Then, it is possible to realize an accurate assay.

The biosensor and the measurement circuit may be provided on the same chip; and the chip can be replaced with another. Then, it is possible to prevent the contamination between samples, thereby simplifying the assay process.

The measurement circuit may further include a current level signal generation section for receiving the first current level signal and the second current level signal to output, to the signal processing circuit, a third current level signal representing a level of a current flowing between the working electrode and the counter electrode. Then, it is possible to simplify the configuration of the signal processing circuit to be provided in a subsequent stage, thereby reducing the size of the device.

The reference terminal may be connected to the working electrode; and the measurement circuit may include: a working electrode voltage application section connected to the working electrode terminal and having an ammeter; a working electrode potential reference circuit connected to the reference terminal; a counter electrode voltage application section connected to the counter electrode terminal; a base voltage source for supplying a base voltage to each of the working electrode potential reference circuit and the counter electrode voltage application section; and a signal processing circuit for processing a current level signal output from the working electrode voltage application section according to a level of a current flowing through the working electrode terminal during an assay.

It is preferred, for a high-precision assay, that the working electrode potential reference circuit generates a signal so that a voltage applied to the reference terminal is substantially equal to the base voltage supplied to the working electrode potential reference circuit during an assay.

The reference terminal may be connected to the counter electrode; and the measurement circuit may include: a working electrode voltage application section connected to the working electrode terminal; a counter electrode voltage application section connected to the counter electrode terminal and having an ammeter; a counter potential reference circuit connected to the reference terminal; a base voltage source for supplying a base voltage to each of the counter electrode potential reference circuit and the working electrode voltage application section; and a signal processing circuit for processing a current level signal output from the counter electrode voltage application section according to a level of a current flowing through the counter electrode terminal during an assay.

In such a case, it is preferred, for a high-precision assay, that the counter electrode potential reference circuit generates a signal so that a voltage applied to the reference terminal is substantially equal to the base voltage supplied to the counter electrode potential reference circuit during an assay.

The reference terminal may be connected to the working electrode; and the measurement circuit may include: a working electrode voltage application section connected to the working electrode terminal and the reference terminal and having an ammeter; a counter electrode voltage application section connected to the counter electrode terminal; a base voltage source for supplying a base voltage to each of the working electrode voltage application section and the counter electrode voltage application section; and a signal processing circuit for processing a current level signal output from the working electrode voltage application section according to a level of a current flowing through the working electrode terminal during an assay.

The reference terminal may be connected to the counter electrode; and the measurement circuit may include: a working electrode voltage application section connected to the working electrode terminal; a counter electrode voltage application section connected to the counter electrode terminal and the reference terminal and having an ammeter; a base voltage source for supplying a base voltage to each of the counter electrode voltage application section and the working electrode voltage application section; a signal processing circuit for processing a current level signal output from the counter electrode voltage application section according to a level of a current flowing through the counter electrode terminal during an assay.

Moreover, the device as a whole may be disposable. Then, it is possible to perform an assay more easily.

BEST MODE FOR CARRYING OUT THE INVENTION

Figure 1:
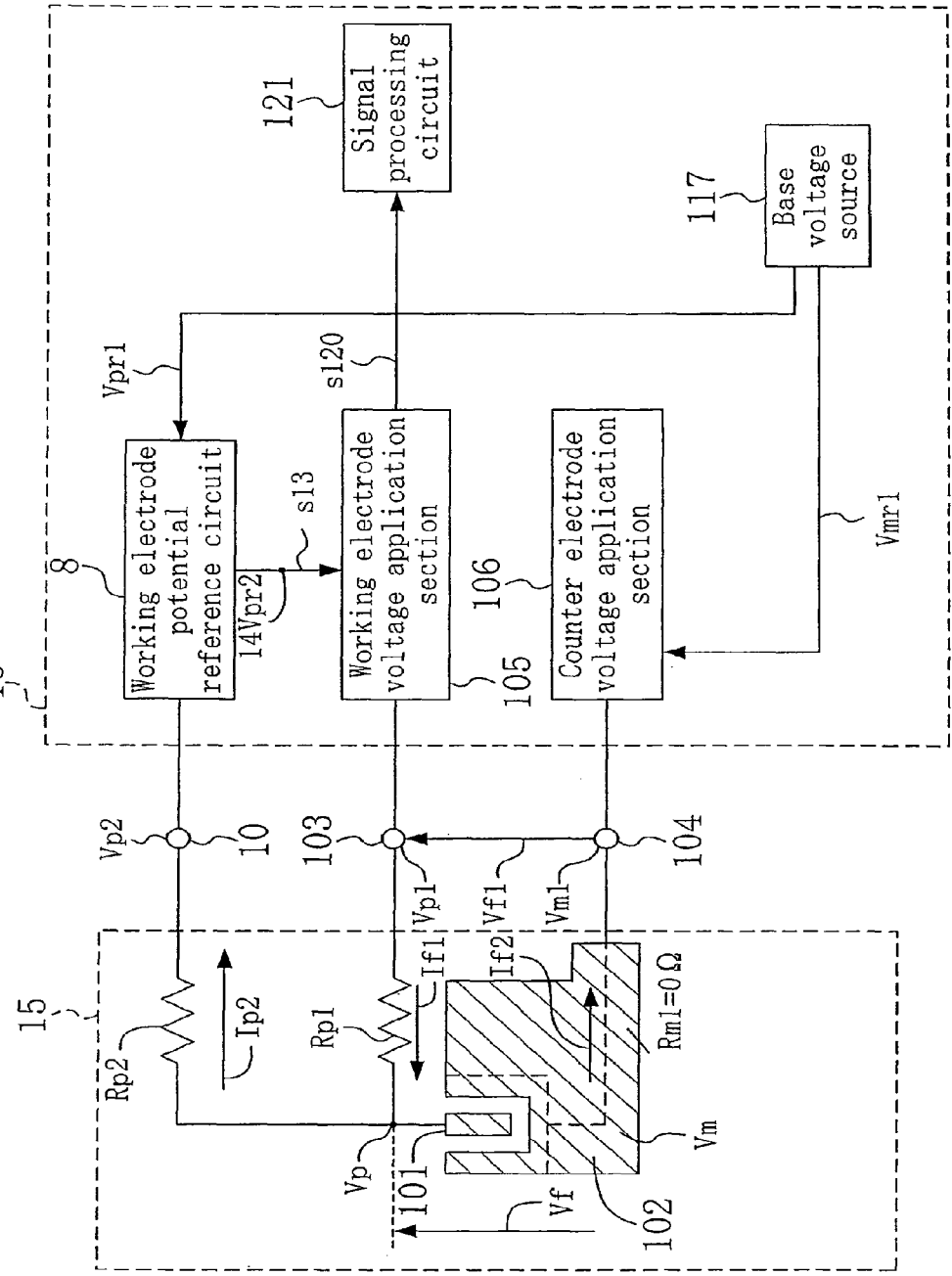
FIG. 1 is a circuit diagram illustrating a portion of a biosensor device of the first embodiment of the present invention.

Embodiments of the present invention will now be described with reference to the drawings. Note that like reference numerals denote like members throughout the various embodiments, and those members will not repeatedly be described in detail.

First Embodiment

Figure 9:
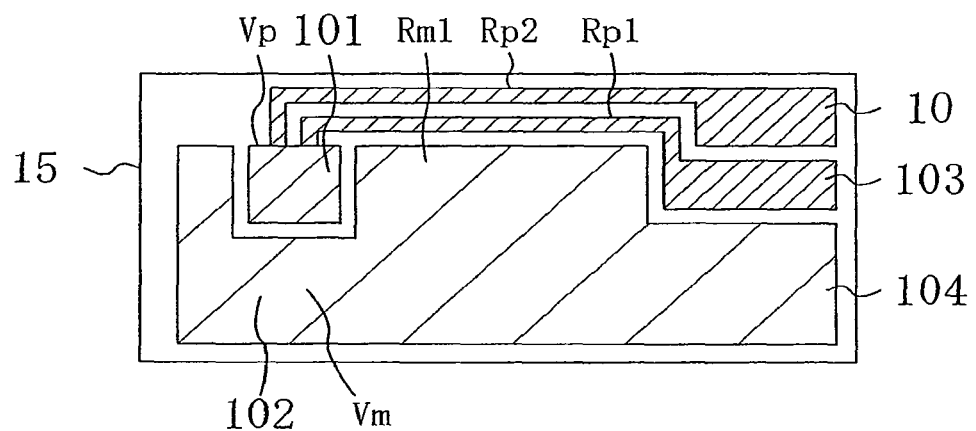
FIG. 9 is a plan view illustrating a biosensor of the first embodiment.

FIG. 1 is a circuit diagram illustrating a portion of a biosensor device of the first embodiment of the present invention, and FIG. 9 is a plan view illustrating a biosensor of the first embodiment.

As illustrated in FIG. 9, a biosensor 15 of the present embodiment includes a working electrode 101, a counter electrode 102 opposing the working electrode 101, a working electrode terminal 103 and a working electrode reference terminal 10 both connected to the working electrode 101, and a counter electrode terminal 104 connected to the counter electrode 102. The connection of the working electrode 101 with the working electrode terminal 103 and the working electrode reference terminal 10, and the connection between the counter electrode 102 and the counter electrode terminal 104 are made by conductive lines made of a relatively inexpensive metal such as Al (aluminum) or Cu (copper). Moreover, the counter electrode 102 is connected to the counter electrode terminal 104 via a conductive line having a sufficient cross-sectional area, whereby a line resistance Rm on the counter electrode side can be regarded to be substantially 0Ω. Therefore, the cross-sectional area of the conductive line between the counter electrode 102 and the counter electrode terminal 104 is greater than that of the conductive line between the working electrode 101 and the working electrode terminal 103.

A sample containing an assayed substance such as glucose is introduced from outside into a reaction section including the working electrode 101 and the counter electrode 102, and is assayed. Where glucose is assayed, for example, when a blood sample contacts glucose oxidase immobilized on the working electrode 101 and the counter electrode 102, hydrogen peroxide is generated through a chemical reaction and electrons are generated. Then, a current flows between the electrodes, and the glucose level is assayed by measuring the current. Note that glucose oxidase does not need to be immobilized on both electrodes, but may alternatively be immobilized on either the working electrode 101 or the counter electrode 102.

Next, the biosensor device of the present embodiment illustrated in FIG. 1 includes the biosensor 15 as described above and a measurement circuit 16 connected to the working electrode reference terminal 10, the working electrode terminal 103 and the counter electrode terminal 104.

The measurement circuit 16 includes a working electrode potential reference circuit 8 connected to the working electrode reference terminal 10, a working electrode voltage application section 105 connected to the working electrode terminal 103 and having an ammeter, a counter electrode voltage application section 106 connected to the counter electrode terminal 104, a base voltage source 117 supplying the working electrode base voltage Vpr1 and the counter electrode base voltage Vmr1 to the working electrode potential reference circuit 8 and the counter electrode voltage application section 106, respectively, and a signal processing circuit 121 connected to the working electrode voltage application section 105.

Figure 2:
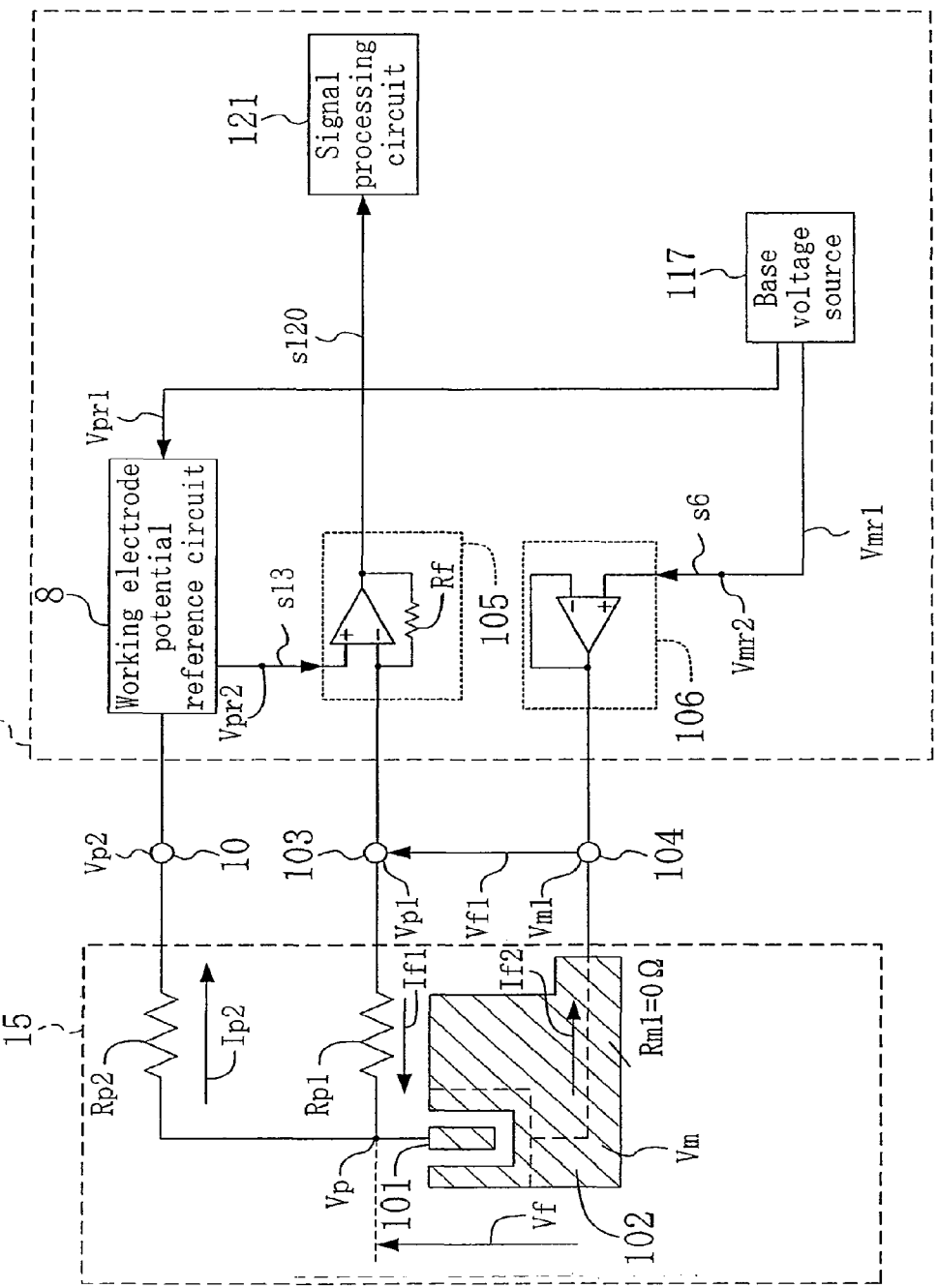
FIG. 2 is a circuit diagram illustrating a portion of the biosensor device of the first embodiment including specific circuit configurations of a working electrode voltage application section and a counter electrode voltage application section.

FIG. 2 is a circuit diagram illustrating the biosensor device of the present embodiment including specific circuit configurations of the working electrode voltage application section 105 and the counter electrode voltage application section 106. As illustrated in the figure, the working electrode voltage application section 105 has a circuit configuration in which a feedback resistance Rf is negatively fed back to an operational amplifier, and the counter electrode voltage application section 106 has an operational amplifier in a null-amplifier configuration, i.e., a buffer circuit configuration, thereby realizing the function described above.

A feature of the biosensor and the biosensor device of the present embodiment is that the electrode connected to the working electrode 101 is divided into two, i.e., the working electrode terminal 103 and the working electrode reference terminal 10. The effect of this feature will be described below.

First, in the biosensor device of the present embodiment, the counter electrode base voltage Vmr1 generated from the base voltage source 117 is impedance-converted by the counter electrode voltage application section 106, and then the application voltage Vm1 is supplied from the counter electrode voltage application section 106 to the counter electrode terminal 104. At this time, the following expression holds.

$$Vm1 = Vmr1 \quad (10)$$

Moreover, as the working electrode base voltage Vpr1 generated from the base voltage source 117 and a working electrode reference terminal voltage Vp2 from the working electrode reference terminal 10 are input to the working electrode potential reference circuit 8, the working electrode potential reference circuit 8 generates a working electrode control signal s13 so that the voltage difference therebetween is 0 V. The working electrode control signal voltage, which is the voltage of the working electrode control signal s13, is Vpr2. Then, the relationship of the following expression holds.

$$Vp2 = Vpr1 \quad (11)$$

$$Vp1 = Vpr2 \quad (12)$$

Moreover, the working electrode control signal voltage Vpr2 is impedance-converted by the working electrode voltage application section 105, and then the working electrode control signal voltage Vpr2 is supplied from the working electrode voltage application section 105 to the working electrode terminal 103.

Next, in FIG. 1, the line resistance of the conductive line between the working electrode 101 and the working electrode reference terminal 10 is Rp2, and the working electrode reference terminal current flowing through the line is Ip2.

The input on the side of the working electrode potential reference circuit 8 that is closer to the working electrode reference terminal 10 is at a high input impedance, and the current flowing through the working electrode reference terminal 10 is as shown in the following expression.

$$Ip2 = 0 \quad (13)$$

Therefore, the working electrode reference terminal voltage Vp2 and the working electrode voltage Vp satisfy the following expression.

$$Vp2 = Vp \quad (14)$$

Therefore, from Expressions (10), (11), (13) and (14), the following expression holds for the sensor application voltage Vf.

$$Vf = Vp - Vm$$
$$= Vp2 - (Vm1 + If2 \cdot Rm1)$$

Now, since Rm1=0Ω, $$Vf = Vp2 - Vm1$$
$$= Vpr1 - Vmr1.$$

Therefore, $$Vf = Vpr1 - Vmr1 \quad (15)$$

Thus, the voltage applied to the sensor application voltage Vf is always constant.

Therefore, in the biosensor device of the present embodiment, substituting Expression (15) into Expression (8) yields the following expression.

$$If1 = f\{Q, (Vpr1 - Vmr1)\}$$

Therefore, $$If1 = f(Q). \quad (16)$$

Thus, there is no influence from the line resistance Rp1 of the conductive line of the working electrode 101, and no error occurs in the final blood glucose level measured by the biosensor device. The working electrode terminal voltage Vp1 is controlled by the working electrode potential reference circuit 8 and the working electrode voltage application section 105 as shown in the following expression.

$$Vp1 = Vpr2$$

Therefore, $$Vp1 = Vpr1 + Rp1 \cdot If1. \quad (17)$$

As described above, the biosensor device of the present embodiment includes the biosensor having three electrodes, i.e., the working electrode terminal and the working electrode reference terminal branching from the working electrode, and the counter electrode terminal connected to the counter electrode, and the biosensor device of the present embodiment includes the working electrode potential reference circuit 8 for generating the working electrode control signal s13 so that the potential difference between a working electrode reference voltage Vp2 and the working electrode base potential Vpr1 is 0, whereby it can perform an assay without being influenced by the line resistance. Therefore, it is possible to perform an assay with a higher precision than the conventional biosensor device.

Moreover, since the assayed value is not influenced by the line resistance, it is not necessary to use an expensive noble metal for lines as in the prior art, thus reducing the manufacturing cost.

Note that in the biosensor device of the present embodiment, the current flowing through the working electrode voltage application section 105 is processed by the signal processing circuit 121 to calculate the concentration of the assayed substance, and the calculated concentration is displayed in a display section (not shown), or the like.

Moreover, in the biosensor device of the present embodiment, the conductive lines may be multilayered.

Figure 10:
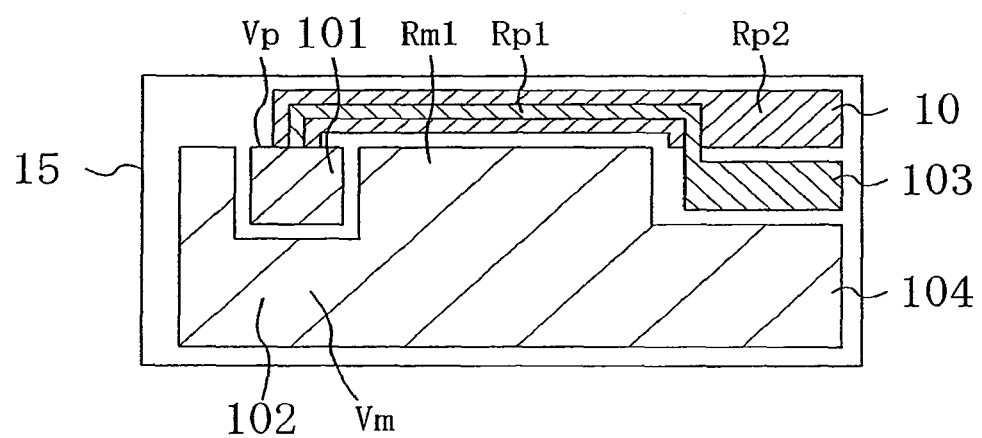
FIG. 10 is a diagram illustrating the biosensor of the first embodiment, where the conductive lines are multilayered.

FIG. 10 is a diagram illustrating the biosensor of the present embodiment, where the conductive lines are multilayered. In the example illustrated in the figure, the conductive line connecting the working electrode 101 to the working electrode reference terminal 10 is provided in a different layer than the conductive line connected to the working electrode terminal 103, i.e., the two conductive lines overlap each other as viewed from above.

With such a structure, the area of the biosensor can be reduced from that of the biosensor illustrated in FIG. 9. Moreover, the reduction in the area is advantageous in integrating biosensors for assaying different substances together on a chip, and it may also lead to a reduction in the manufacturing cost. For example, a biosensor for measuring the grape sugar level and a biosensor for measuring the liver function indicators such as GOT and GTP may be multilayered together, whereby different assays can be done with a single blood sample, thus reducing the burden on the patient.

Moreover, multilayered lines may be used not only for the conductive lines for the working electrode but also for those for the counter electrode. As biosensors are further miniaturized, the wiring area for the counter electrode is reduced, thereby making it more difficult to bring the resistance close to 0. Therefore, by multilayering the conductive lines for the counter electrode by providing them in two or more layers, the substantial wiring area can be increased, and the resistance value can be reduced.

Note that biosensor devices currently being sold widely are those for assaying glucose in which glucose oxidase, or the like, is immobilized on the counter electrode and the working electrode. However, a different substance may be immobilized on the electrodes in order to assay a substance that binds to the immobilized substance, a substance that reacts with the immobilized substance, or a substance that is decomposed or synthesized through a catalytic reaction with the immobilized substance. For example, a single-stranded DNA may be immobilized on the electrodes in order to detect a DNA or an RNA that pairs with the immobilized DNA. As a DNA becomes double-stranded, the electrical conductivity thereof changes, whereby it can be detected electrically. This can be used in tests for diseases. For example, while a test for AIDS requires months before the antibody is generated, it is possible to detect an infection soon after the infection by performing an RNA assay.

Alternatively, a biological substance such as any of various enzymes may be immobilized on the electrodes, or a microorganism may be immobilized on the electrodes. For example, a microorganism assimilating carbon dioxide may be immobilized in order to assay carbon dioxide in blood. Note that the term "biological substance" as used herein refers to proteins, amino acids, genes, and other organic matters in general, contained in the body of a living thing.

Moreover, it is possible to obtain a more detailed assayed value with an electric assay than with a colorimetric assay using fluorescence. Therefore, the biosensor device of the present embodiment, capable of performing a precise assay, is useful in making a treatment plan.

Note that in the biosensor device of the present embodiment, only the biosensor 15 or the biosensor with the measurement circuit 16 is disposable. Alternatively, the device assembly including the display section and various other units may be disposable.

Note that while it is possible to employ a 4-terminal structure with a counter electrode reference terminal on the counter electrode side, the biosensor of the present embodiment, as compared with one having a 4-electrode structure, requires a smaller number of components, whereby it is possible to reduce the cost and increase the wiring area. In contrast, where a high precision is required, a 4-terminal biosensor device is preferred. This will be described in detail in subsequent embodiments.

Note that in the biosensor of the present embodiment, the working electrode terminal and working electrode reference terminal are branching from the working electrode. Alternatively, the conductive line connected to the working electrode terminal and the conductive line connected to the working electrode reference terminal may be a partially shared conductive line branching into two lines at a certain point.

Second Embodiment

Figure 11:
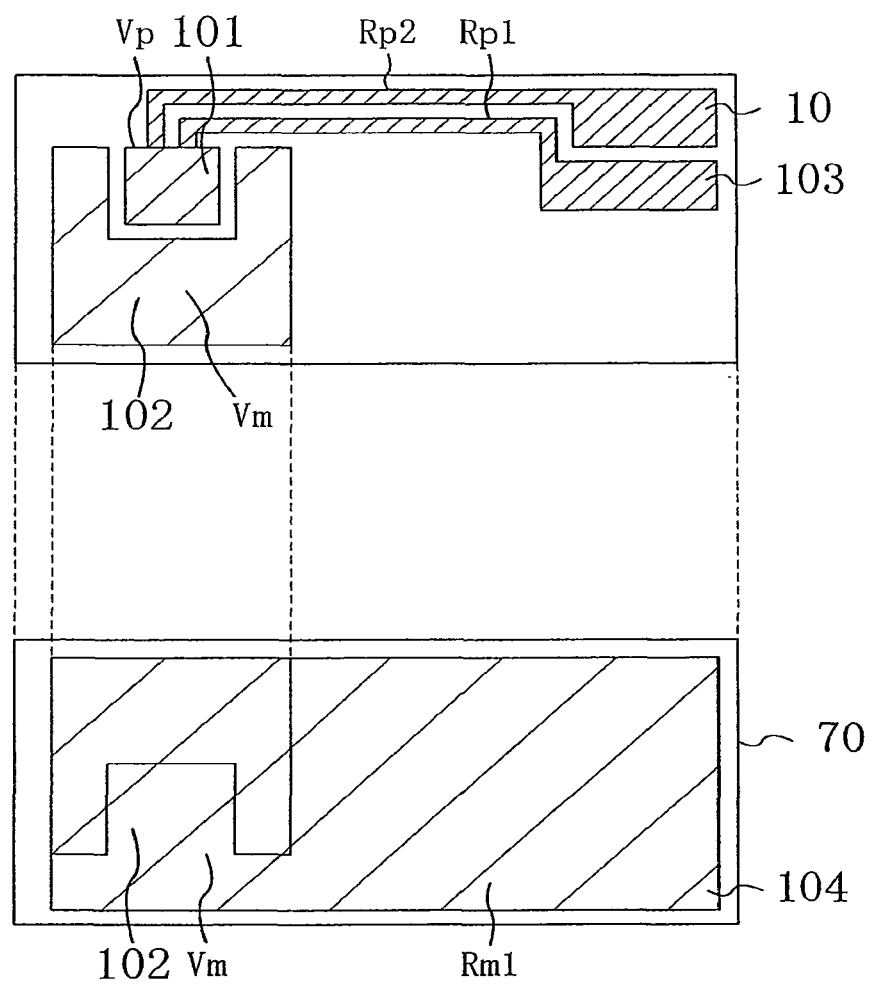
FIG. 11 shows a plan view and a perspective view illustrating a biosensor of the second embodiment of the present invention.

FIG. 11 shows a plan view and a perspective view illustrating a biosensor 70 of the second embodiment of the present invention.

As illustrated in the figure, the biosensor of the present embodiment includes the working electrode 101, the counter electrode 102 opposing the working electrode 101, the working electrode reference terminal 10 and the working electrode terminal 103 connected to the working electrode 101, and the counter electrode terminal 104 connected to the counter electrode 102.

A feature of the biosensor of the present embodiment is that the counter electrode terminal 104 connected to the counter electrode 102 extends through the structure from the surface on which the working electrode 101 is formed to the reverse surface, making the entire reverse surface the counter electrode terminal.

With such a structure, it is possible to further reduce the line resistance value Rm1 on the counter electrode terminal side without changing the size of the biosensor, thereby realizing a high-precision biosensor.

As described above, the biosensor of the present embodiment has a 3-electrode structure with the working electrode, the working electrode reference terminal and the counter electrode, wherein the counter electrode terminal extends through the structure from the surface on which the working electrode is formed to the reverse surface, making the entire reverse surface the counter electrode, whereby it is possible to realize a high-precision assay.

Third Embodiment

Figure 12:
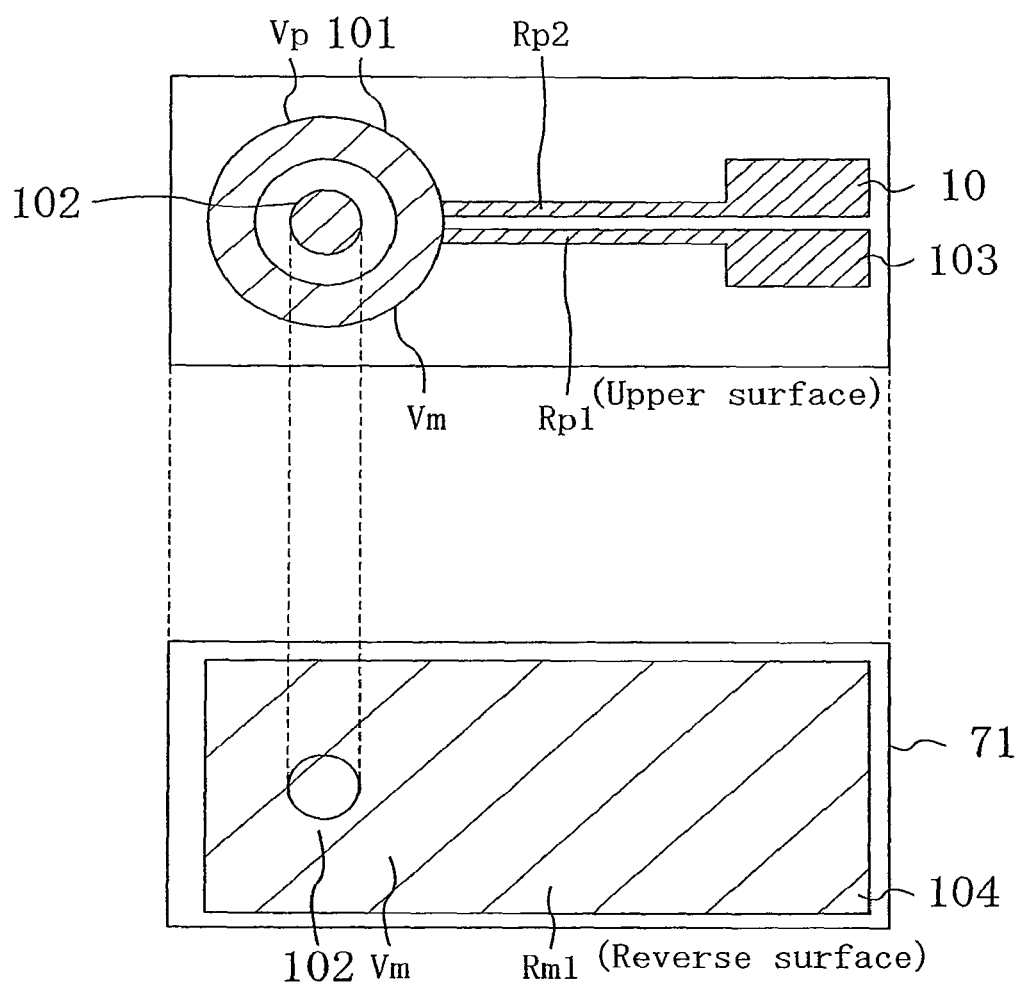
FIG. 12 shows a plan view and a perspective view illustrating a biosensor of the third embodiment of the present invention.

FIG. 12 shows a plan view and a perspective view illustrating a biosensor of the third embodiment of the present invention.

As illustrated in the figure, the biosensor of the present embodiment includes the generally-circular counter electrode 102, the concentric ring-shaped working electrode 101 surrounding the counter electrode 102 with a constant interval therebetween, the working electrode reference terminal 10 and the working electrode terminal 103 connected to the working electrode 101, and the counter electrode terminal 104 connected to the counter electrode 102. The counter electrode terminal 104 extends through the structure from the surface on which the working electrode 101 is formed to the reverse surface and extends across the entire reverse surface.

In the biosensor of the present embodiment, the working electrode 101 is formed in a concentric shape, whereby an enzyme and an assayed substance can be reacted with each other in a uniform manner. Moreover, the electric field acting upon the working electrode is made uniform, whereby it is possible to further improve the assay precision.

Moreover, the counter electrode terminal 104 is provided so as to extend across the entire reverse surface, as in the second embodiment, thereby reducing the resistance on the counter electrode side and improving the assay precision.

Thus, with the biosensor of the present embodiment, it is possible to perform an assay with a significantly higher precision as compared with the prior art.

Note that while the working electrode 101 is in a concentric shape in the biosensor of the present embodiment, it may alternatively take a partial circular shape, e.g., by a semicircular shape, for making the electric field acting upon the working electrode uniform.

Fourth Embodiment

Figure 13:
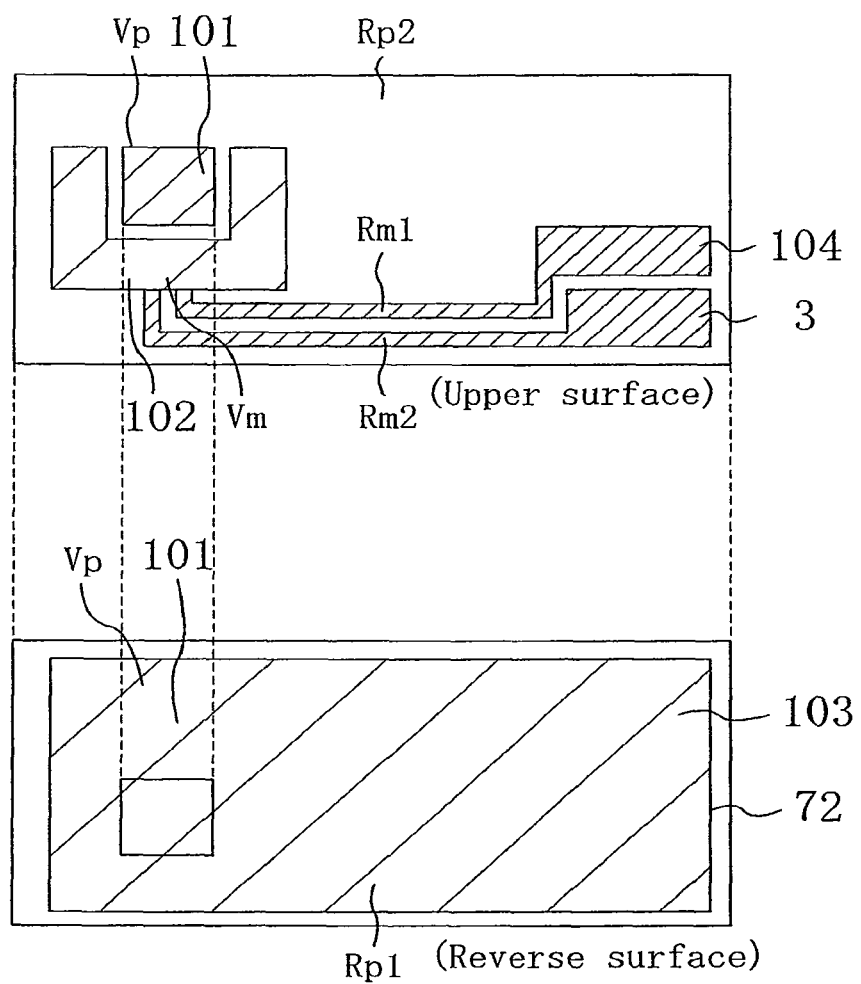
FIG. 13 shows a plan view and a perspective view illustrating a biosensor of the fourth embodiment of the present invention.

FIG. 13 shows a plan view and a perspective view illustrating a biosensor of the fourth embodiment of the present invention. As illustrated in the figure, a biosensor 72 of the present embodiment includes the working electrode 101, the counter electrode 102 provided so as to oppose the working electrode, the working electrode terminal 103 connected to the working electrode 101 and provided so as to extend across the entire reverse surface, and the counter electrode terminal 104 and a counter electrode reference terminal 3 connected to the counter electrode 102.

A 3-electrode structure may be obtained by providing a reference electrode on the counter electrode side, as in the present embodiment. Also in this case, it is possible to perform a high-precision assay as the resistance of the conductive lines does not influence the assayed value, as described in the first embodiment. Thus, it is possible to use an inexpensive metal for the conductive lines, thereby reducing the manufacturing cost.

Note that in the example illustrated in FIG. 13, the working electrode terminal 103 is formed across the entire reverse surface opposite to the surface on which the working electrode 101 is formed, thereby suppressing the resistance value on the working electrode side to a significantly small value. Note however that it is not necessary that the working electrode terminal 103 is provided on the reverse surface.

As described above, with the biosensor of the present embodiment, it is possible to realize a high-precision assay. Moreover, since the problem of the line resistance due to miniaturization can be solved, the assay precision does not decrease even when biosensors are further miniaturized.

Fifth Embodiment

Figure 14:
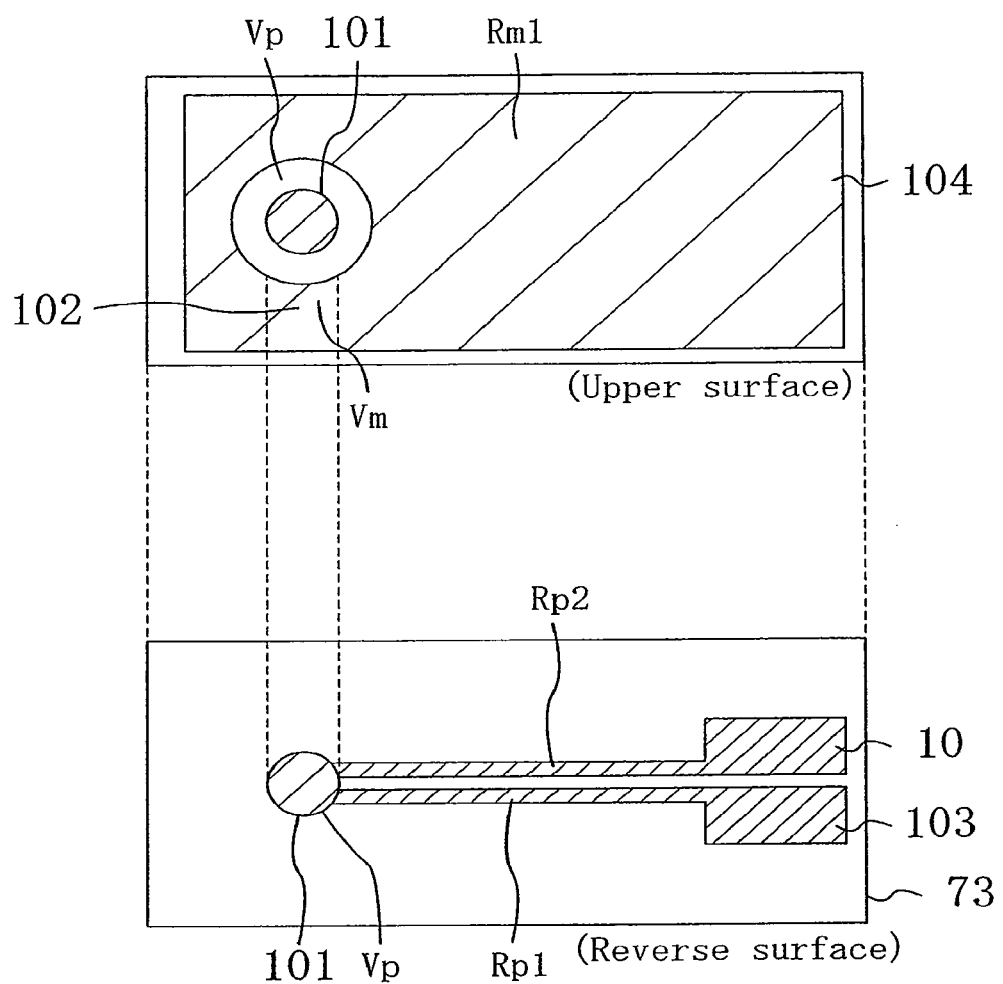
FIG. 14 shows a plan view and a perspective view illustrating a biosensor of the fifth embodiment of the present invention.

FIG. 14 shows a plan view and a perspective view illustrating a biosensor of the fifth embodiment of the present invention. As illustrated in the figure, a biosensor 73 of the present embodiment includes the generally-circular working electrode 101, the counter electrode 102 surrounding the working electrode 101 with a constant interval therebetween, the working electrode reference terminal 10 and the working electrode terminal 103 connected to the working electrode 101 and provided on the reverse surface of the substrate, and the counter electrode terminal 104 provided so as to extend across the entire upper surface of the substrate.

With the biosensor 73 of the present embodiment, the working electrode 101 and the inner periphery of the counter electrode 102 surrounding the working electrode 101 are concentric with each other, whereby an enzyme and an assayed substance can be reacted with each other in a uniform manner. Moreover, the electric field acting upon the electrode is made uniform, thereby further improving the assay precision.

In addition, since the counter electrode terminal 104 is provided so as to extend across the entire upper surface of the substrate, it is possible to suppress the resistance Rm1 on the counter electrode side to a very small value. Therefore, the biosensor of the present embodiment provides an improved assay precision.

Thus, it is possible to realize a biosensor capable of performing a high-precision assay by making the working electrode and the inner periphery of the counter electrode concentric with each other and by providing the counter electrode terminal 104 on the upper surface of the substrate.

Sixth Embodiment

Figure 3:
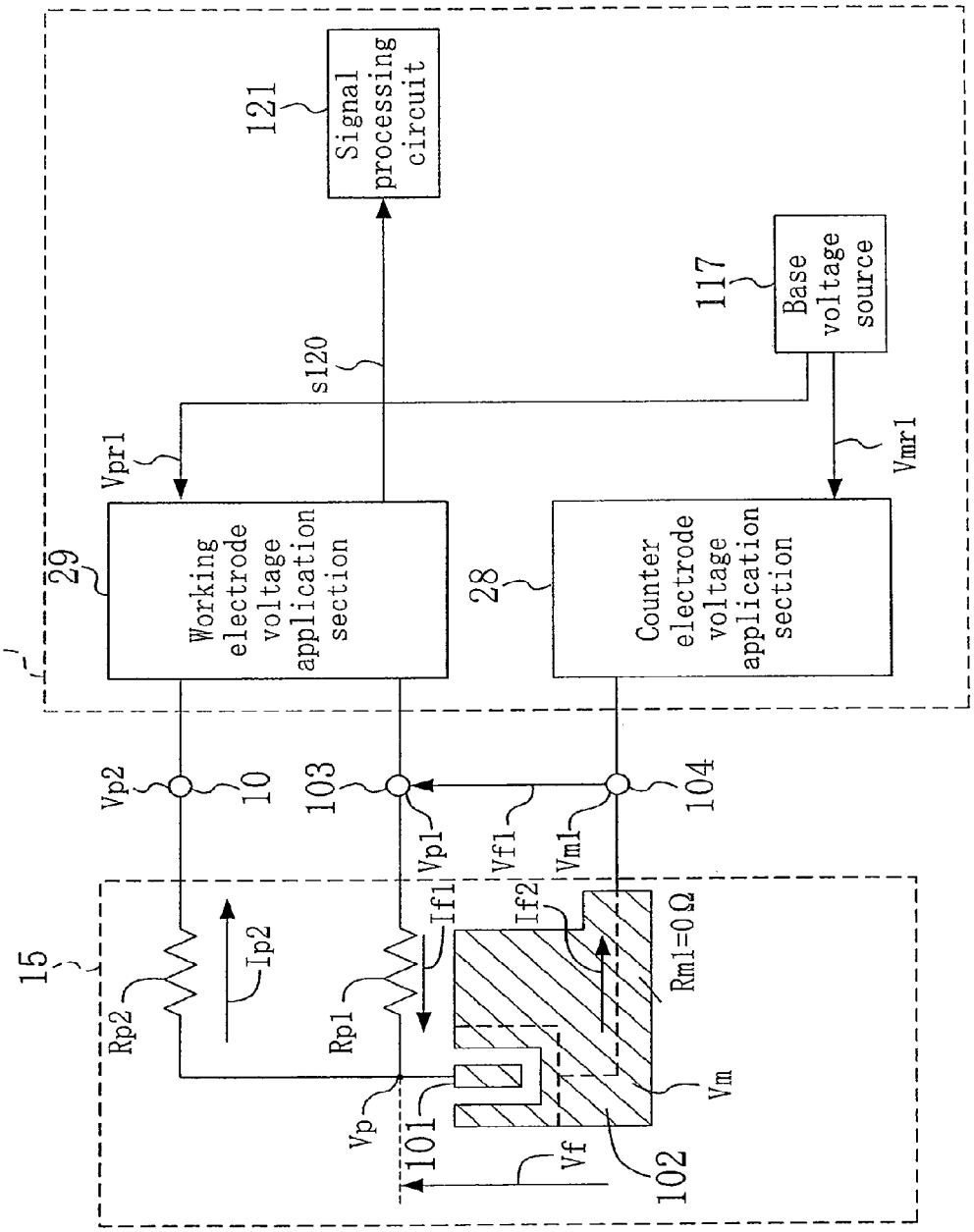
FIG. 3 is a circuit diagram illustrating a portion of a biosensor device of the sixth embodiment of the present invention.
Figure 4:
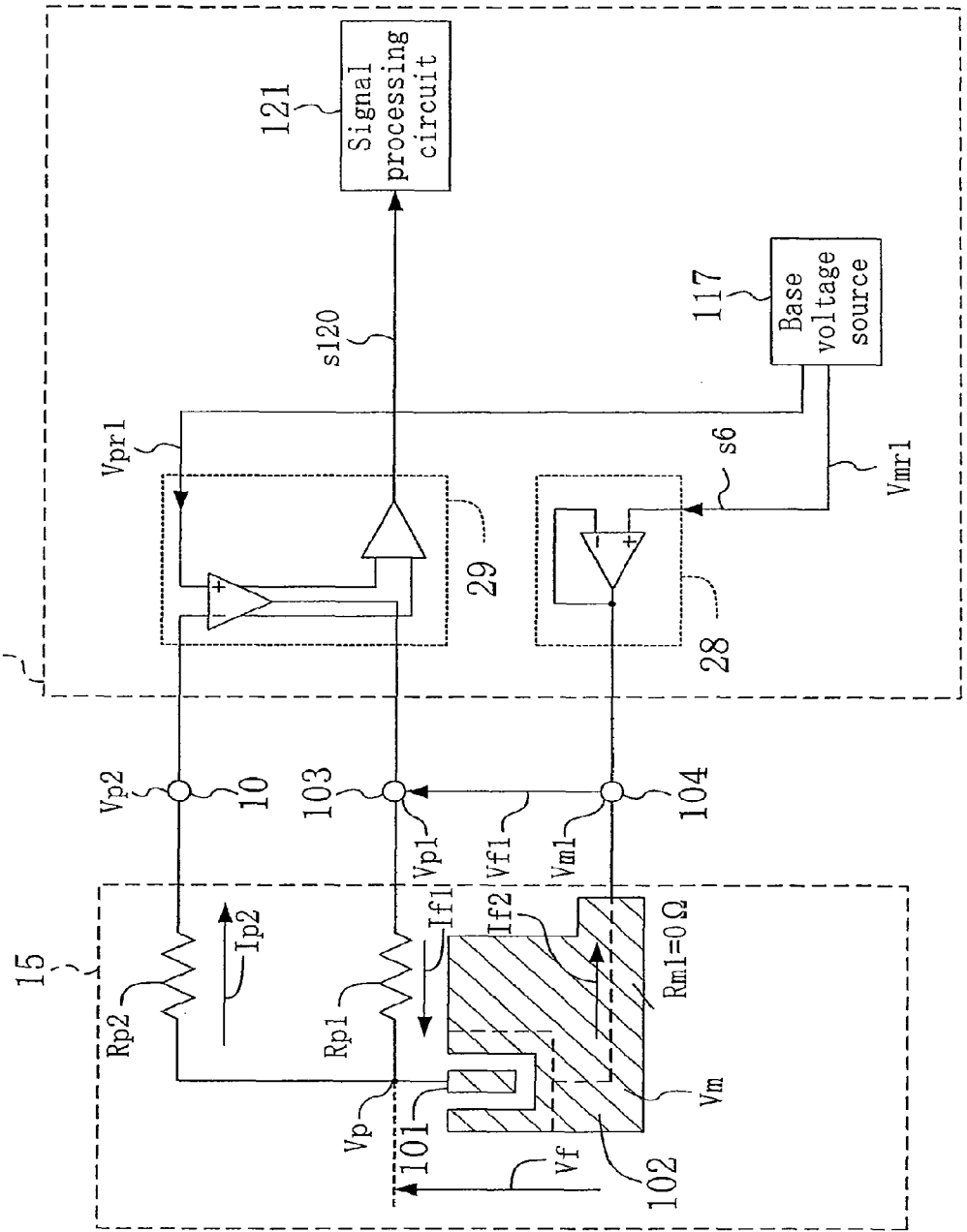
FIG. 4 is a circuit diagram illustrating a portion of the biosensor device of the sixth embodiment including specific configurations of a working electrode voltage application section and a counter electrode voltage application section.

FIG. 3 is a circuit diagram illustrating a portion of a biosensor device of the sixth embodiment of the present invention, and FIG. 4 is a circuit diagram illustrating a portion of the biosensor device of the present embodiment including specific configurations of a working electrode voltage application section 29 and a counter electrode voltage application section 28.

As illustrated in FIG. 3, the biosensor device of the present embodiment includes the biosensor 15, and the measurement circuit 16 connected to the biosensor 15.

The biosensor 15 includes the working electrode 101, the counter electrode 102 opposing the working electrode 101, the working electrode reference terminal 10 and the working electrode terminal 103 connected to the working electrode 101, and the counter electrode terminal 104 connected to the counter electrode 102. The working electrode 101 is connected to the working electrode reference terminal 10 and the working electrode terminal 103 by conductive lines each made of Cu, Al, or the like.

Moreover, the measurement circuit 16 includes the working electrode voltage application section 29 connected to the working electrode reference terminal 10 and the working electrode terminal 103 and having an ammeter, the counter electrode voltage application section 28 connected to the counter electrode terminal 104, the base voltage source 117 supplying the working electrode base voltage Vpr1 to the working electrode voltage application section 29 and the counter electrode base voltage Vmr1 to the counter electrode voltage application section 28, and the signal processing circuit 121 for processing the current input to the working electrode voltage application section 29. The working electrode voltage application section 29 is a voltage-current conversion circuit disclosed in Japanese Laid-Open Patent Publication No. 11-154833 (U.S. Pat. No. 5,986,910).

In the biosensor device of the present embodiment, the counter electrode base voltage Vmr1 generated from the base voltage source 117 is impedance-converted by the counter electrode voltage application section 28, and then the counter electrode terminal voltage Vm1 is applied from the counter electrode voltage application section 28. At this time, the following expression holds.

$$Vm1 = Vmr1 \quad (18)$$

Moreover, the working electrode base voltage Vpr1 and the working electrode reference terminal voltage Vp2 of the working electrode reference terminal 10 of the biosensor 15 are input to the working electrode voltage application section 29, and the working electrode control signal voltage Vp1 is supplied to the working electrode terminal 103 so that the voltage difference therebetween is substantially 0 V. At this time, the following expression holds.

$$Vp2 = Vpr1 \quad (19)$$

The value of the current flowing out to the working electrode terminal 103 is measured by the working electrode voltage application section 29, and a working electrode current level signal s120, which is the result of the measurement, is supplied to the signal processing circuit 121. Based on the measured current level, the concentration of the assayed component is calculated, and a result displaying operation, etc., is performed.

Moreover, since the input of the working electrode reference terminal 10 of the working electrode voltage application section 29 is at a high input impedance, the current flowing through the reference electrode is as shown in the following expression.

$$Ip2 = 0 \quad (20)$$

Therefore, the working electrode reference terminal voltage Vp2 and the working electrode voltage Vp satisfy the following expression.

$$Vp2 = Vp \quad (21)$$

Therefore, from Expressions (18), (19), (20) and (21), the following expression holds for the sensor application voltage Vf.

$$Vf = Vp - Vm$$
$$= Vp2 - (Vm1 + If2 \cdot Rm1)$$

Now, since Rm1=0Ω, $$Vf = Vp2 - Vm1$$
$$= Vpr1 - Vmr1.$$

Therefore, $$Vf = Vpr1 - Vmr1. \quad (22)$$

Thus, the voltage applied to the sensor application voltage Vf is always constant. Therefore, in the present sixth embodiment, substituting Expression (22) into Expression (8) yields the following expression.

$$If1 = f\{Q, (Vpr1 - Vmr1)\}$$

Therefore, $$If1 = f(Q). \quad (23)$$

Therefore, there is no influence at all of the line resistance Rp1 of the conductive line connecting the working electrode 101 to the working electrode terminal 103, and no error is contained in the blood glucose level, for example, assayed by the biosensor device.

The working electrode terminal voltage Vp1 is controlled by the working electrode voltage application section 29 as shown in the following expression.

$$Vp1 = Vpr1 + Rp1 \cdot If1 \quad (24)$$

The biosensor device of the present embodiment is different from the biosensor device of the first embodiment in that the biosensor device of the present embodiment includes the working electrode voltage application section 29 connected to both the working electrode reference terminal 10 and the working electrode terminal 103. With this structure, it is possible to omit the capacitor for stabilizing the circuit, whereby it is possible to reduce the overall circuit area.

Thus, also in the structure where the working electrode voltage application section 29 functions also as the working electrode potential reference circuit, it is possible to realize a high-precision biosensor device that is not influenced by the line resistance on the working electrode side.

Note that an operational amplifier in which the negative input is connected to the working electrode reference terminal 10, the positive input is connected to the base voltage source 117, and the output is connected to the working electrode terminal 103, as illustrated in FIG. 4, is shown as a specific example of the working electrode voltage application section 29. However, the present invention is not limited to this configuration.

Seventh Embodiment

Figure 5:
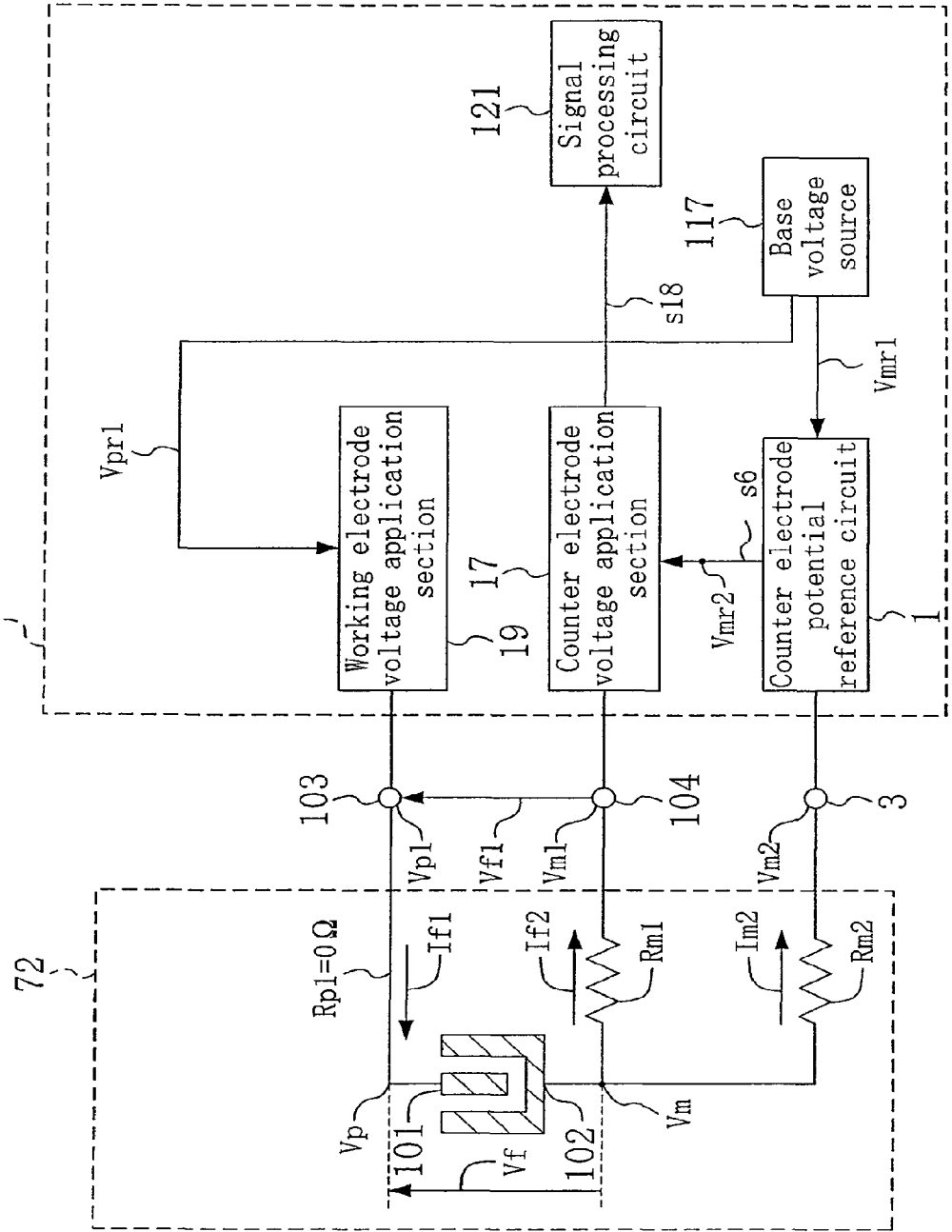
FIG. 5 is a circuit diagram illustrating a portion of a biosensor device of the seventh embodiment of the present invention.
Figure 6:
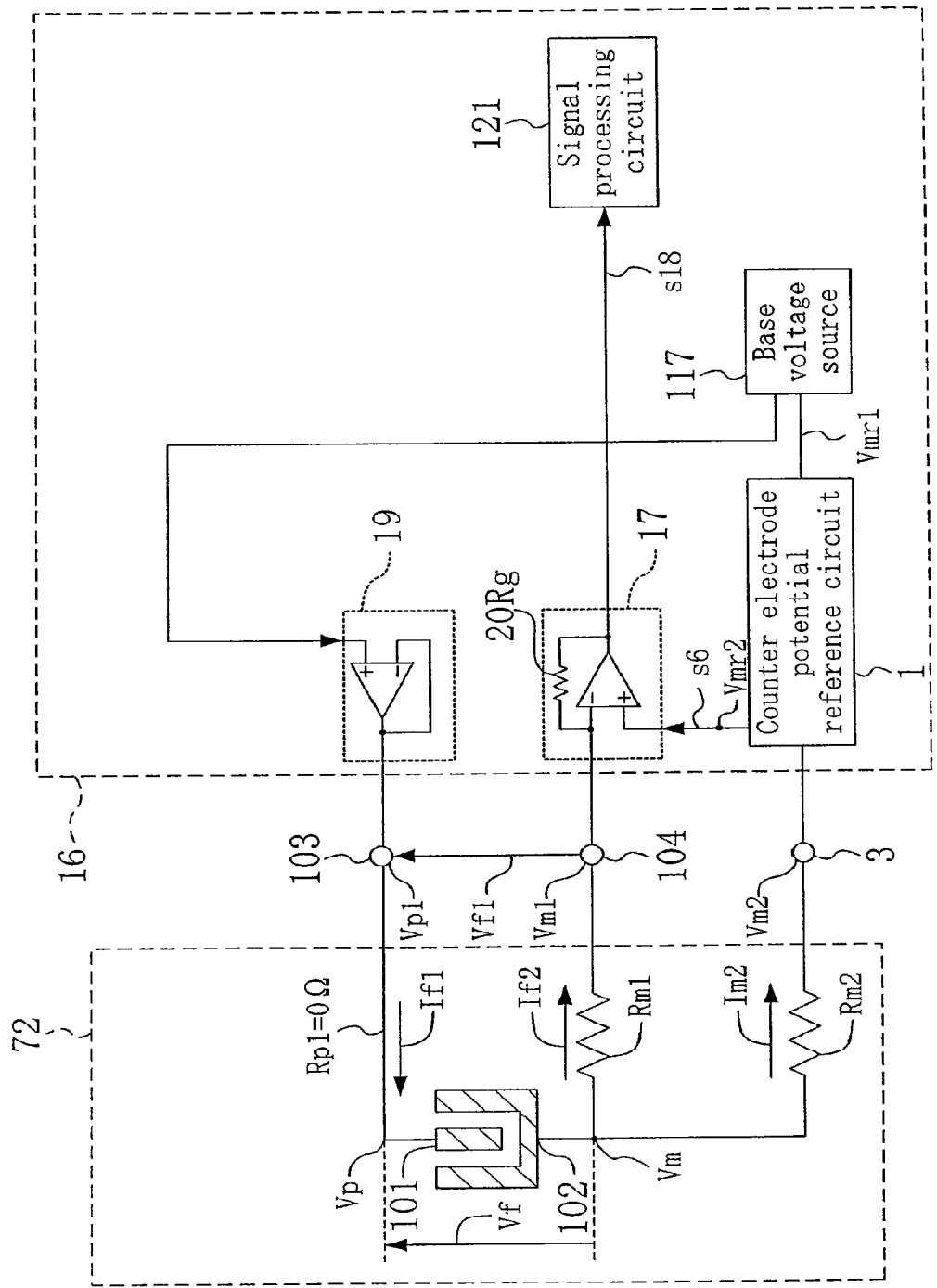
FIG. 6 is a circuit diagram illustrating a portion of the biosensor device of the seventh embodiment including specific configurations of a working electrode voltage application section and a counter electrode voltage application section.

FIG. 5 is a circuit diagram illustrating a portion of a biosensor device of the seventh embodiment of the present invention, and FIG. 6 is a circuit diagram illustrating a portion of the biosensor device of the present embodiment including specific configurations of a working electrode voltage application section 19 and a counter electrode voltage application section 17.

As illustrated in FIG. 5, the biosensor device of the present embodiment includes the biosensor 72, and the measurement circuit 16 connected to the biosensor 72.

The biosensor 72 includes the working electrode 101, the counter electrode 102 provided so as to oppose the working electrode 101, the working electrode terminal 103 connected to the working electrode 101, and the counter electrode terminal 104 and the counter electrode reference terminal 3 connected to the counter electrode 102. The cross-sectional area of the conductive line connecting the working electrode 101 to the working electrode terminal 103 is sufficiently large so that the line resistance can be made substantially 0Ω. The biosensor 72 includes the counter electrode reference terminal 3, as does the biosensor of the fourth embodiment.

Moreover, the measurement circuit 16 includes the working electrode voltage application section 19 connected to the working electrode terminal 103, the counter electrode voltage application section 17 connected to the counter electrode terminal 104 and having an ammeter, a counter electrode potential reference circuit 1 connected to the counter electrode reference electrode 3, the base voltage source 117 supplying the working electrode base voltage Vpr1 to the working electrode voltage application section 19 and the counter electrode base voltage Vmr1 to the counter electrode potential reference circuit 1, and the signal processing circuit 121 for processing a counter electrode current level signal s18 output from the counter electrode voltage application section 17 according to the input current.

In the biosensor device of the present embodiment, the working electrode base voltage Vpr1 generated from the base voltage source 117 is impedance-converted by the working electrode voltage application section 19, and then the working electrode terminal voltage Vp1 is supplied from the working electrode voltage application section 19 to the working electrode terminal 103. At this time, the following expression holds.

$$Vp1 = Vpr1 \quad (25)$$

Moreover, when the counter electrode base voltage Vmr1 generated from the base voltage source 117 and a working electrode reference terminal voltage Vm2 are input to the counter electrode potential reference circuit 1, the counter electrode potential reference circuit 1 generates a counter electrode control signal s6 so that the voltage difference therebetween is 0 V. The voltage of the counter electrode control signal s6 (working electrode control signal voltage) is Vmr2. At this time, the following expressions hold.

$$Vm2 = Vmr1 \quad (26)$$

$$Vm1 = Vmr2 \quad (27)$$

In FIG. 5, the current flowing out to the counter electrode terminal 104 is measured by the counter electrode voltage application section 17, and the result is supplied to the signal processing circuit 121 in the form of the counter electrode current level signal s18. Then, based on the measured current level, the concentration of the assayed component is calculated, and a result displaying operation, etc., is performed.

As in the first embodiment described above, the following expression holds for the sensor application voltage Vf.

$$\begin{aligned} Vf &= Vp - Vm \\ &= Vp1 - (Vm2 + If1 \cdot Rp1) \end{aligned}$$

Now, since Rp1=0Ω, $$\begin{aligned} Vf &= Vp1 - Vm2 \\ &= Vpr1 - Vmr1. \end{aligned}$$

Therefore, $$Vf = Vpr1 - Vmr1. \quad (28)$$

Since Vpr1 and Vmr1 are constant, the sensor application voltage Vf is always a constant value. Therefore, in the present third embodiment, substituting Expression (28) into Expression (8) yields the following expression.

$$If2 = f\{Q,(Vpr1-Vmr1)\}$$

Therefore, $$If2 = f(Q). \quad (29)$$

Therefore, the line resistance Rm1 of the conductive line on the counter electrode 102 side does not influence If2 flowing through the counter electrode terminal 104, whereby no error is contained in the final blood glucose level measured by the biosensor device.

The counter electrode terminal voltage Vm1 is controlled by the counter electrode potential reference circuit 1 and the counter electrode voltage application section 17 as shown in the following expression.

$$Vm1 = Vmr2$$

Therefore, $$Vm1 = Vmr1 - Rm1 \cdot If2. \quad (30)$$

Thus, it can be seen that with the seventh embodiment of the present invention, it is possible to perform a high-precision assay irrespective of the resistance of the conductive lines even with a 3-electrode structure including the counter electrode terminal 104 and the counter electrode reference electrode 3 on the counter electrode side. In addition, it requires a smaller number of components than in a case where four or more electrodes are provided, for example, whereby it is possible to realize a low-cost, high-precision biosensor device.

Moreover, in the specific circuit example illustrated in FIG. 6, the counter electrode voltage application section 17 has a circuit configuration in which a feedback resistance Rg20 is negatively fed back to an operational amplifier, and the working electrode voltage application section 19 has an operational amplifier in a null-amplifier configuration, i.e., a buffer circuit configuration. In this way, the counter electrode voltage application section 17 and the working electrode voltage application section 19 provide the functions as described above. Note that the counter electrode voltage application section 17 and the working electrode voltage application section 19 may alternatively have a different circuit configuration.

Eighth Embodiment

Figure 7:
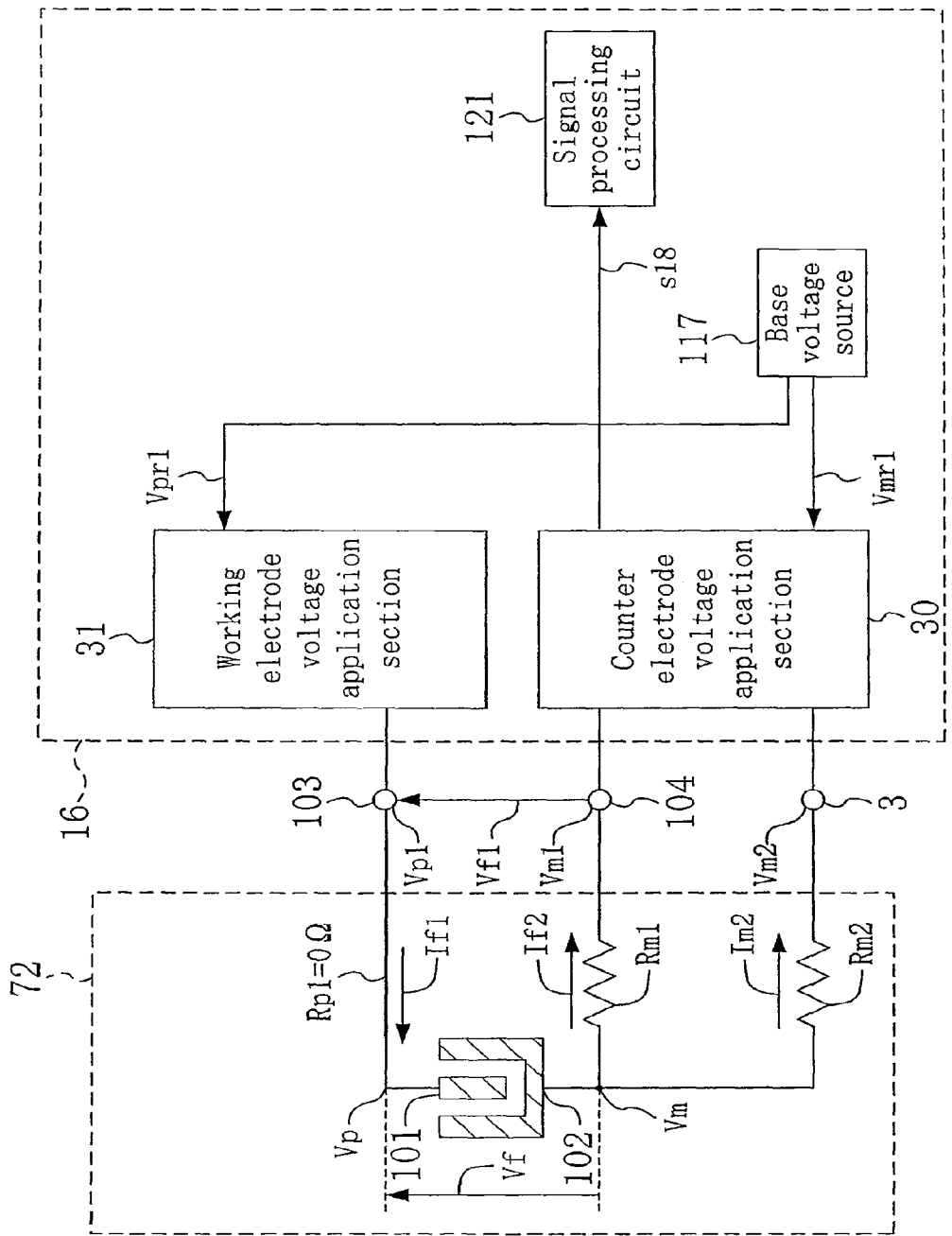
FIG. 7 is a circuit diagram illustrating a portion of a biosensor device of the eighth embodiment of the present invention.
Figure 8:
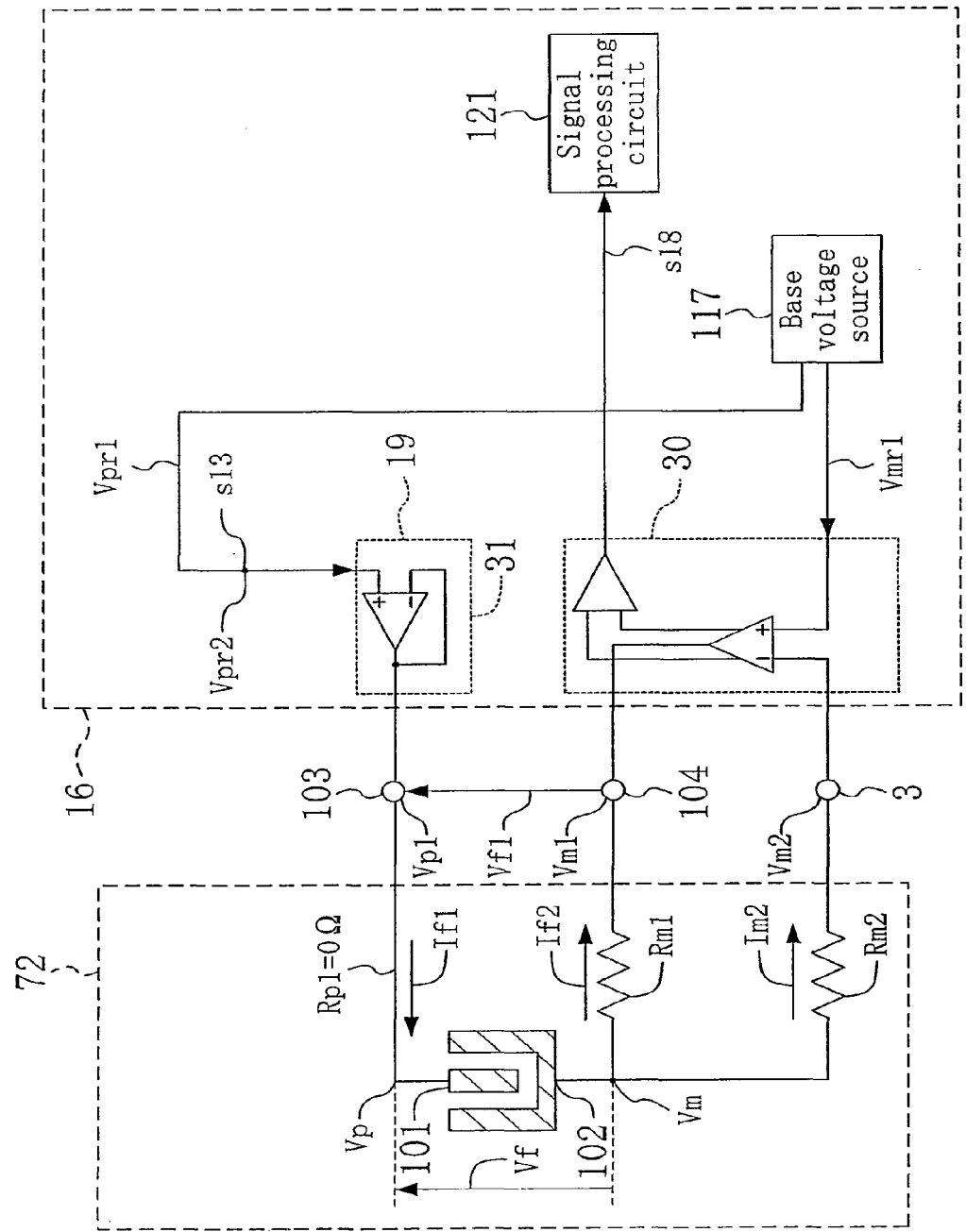
FIG. 8 is a circuit diagram illustrating a portion of the biosensor device of the eighth embodiment including specific configurations of a working electrode side potential reference voltage source and a counter electrode side potential reference voltage source with an ammeter.

FIG. 7 is a circuit diagram illustrating a portion of a biosensor device of the eighth embodiment of the present invention, and FIG. 8 is a circuit diagram illustrating a portion of the biosensor device of the present embodiment including specific configurations of a working electrode voltage application section 31 and a counter electrode voltage application section 30.

As illustrated in FIG. 7, the biosensor device of the present embodiment includes the biosensor 72, and the measurement circuit 16 connected to the biosensor 72.

The configuration of the biosensor 72 is the same as that of the seventh embodiment.

The measurement circuit 16 includes the working electrode voltage application section 31, the counter electrode voltage application section 30 connected to the counter electrode terminal 104 and the counter electrode reference electrode 3 and having an ammeter, the base voltage source 117 supplying the working electrode base voltage Vpr1 to the working electrode voltage application section 31 and the counter electrode base voltage Vmr1 to the counter electrode voltage application section 30, and the signal processing circuit 121 for processing the counter electrode current level signal s18 from the counter electrode voltage application section 30.

The biosensor device of the present embodiment is different from the seventh embodiment in that the counter electrode potential reference circuit 1 is absent, and the counter electrode voltage application section 30 is connected to both the counter electrode terminal 104 and the counter electrode reference electrode 3.

In the biosensor device of the present embodiment illustrated in FIG. 7, the counter electrode base voltage Vmr1 and the counter electrode reference electrode voltage Vm2 of the counter electrode reference electrode 3 are both input to the counter electrode voltage application section 30, and the counter electrode control signal voltage Vmr2 is supplied to the counter electrode terminal 104 so that the voltage difference therebetween is 0 V. At this time, the following expression holds.

$$Vm2 = Vmr1 \quad (31)$$

Moreover, the working electrode base voltage Vpr1 is impedance-converted by the working electrode voltage application section 31, and then the voltage Vp1 is supplied from the working electrode voltage application section 31 to the working electrode terminal 103. At this time, the following expression holds.

$$Vp1 = Vpr1 \quad (32)$$

On the other hand, the current flowing out to the counter electrode terminal 104 is measured by the counter electrode voltage application section 30, and the counter electrode current level signal s18 indicating the measurement result is supplied to the signal processing circuit 121. Then, the device assembly calculates the concentration of the assayed component, and a result displaying operation, etc., is performed.

As in the sixth embodiment described above, the following expression holds for the sensor application voltage Vf.

$$Vf = Vp - Vm$$
$$= Vp1 - (Vm2 + If1 \cdot Rp1)$$

Now, since Rp1=0Ω, $$Vf = Vp1 - Vm2$$
$$= Vpr1 - Vmr1.$$

Therefore, $$Vf = Vpr1 - Vmr1. \quad (33)$$

Thus, the sensor application voltage Vf is a constant voltage.

Therefore, substituting Expression (33) into Expression (8) yields the following expression.

$$If2 = f\{Q, (Vpr1 - Vmr1)\}$$

Therefore, $$If2 = f(Q). \quad (34)$$

Therefore, the blood glucose level measured by the biosensor device is not influenced by the line resistance Rm1 of the conductive line on the counter electrode 102 side, whereby no error occurs.

As described above, also when the counter electrode reference electrode 3 and the counter electrode terminal 104 are both connected to the counter electrode voltage application section 30, it is possible to realize a high-precision assay.

Moreover, in the specific circuit example illustrated in FIG. 8, the counter electrode voltage application section 30 has an operational amplifier in which the negative input is connected to the counter electrode reference electrode 3, the positive input is connected to the working electrode base voltage Vmr1, and the output is connected to the working electrode terminal 103. This is a voltage-current conversion circuit disclosed in Japanese Laid-Open Patent Publication No. 11-154833 (U.S. Pat. No. 5,986,910). Note that the present invention is not limited to this configuration.

Ninth Embodiment

A biosensor chip of the ninth embodiment of the present invention will now be described.

Figure 15:
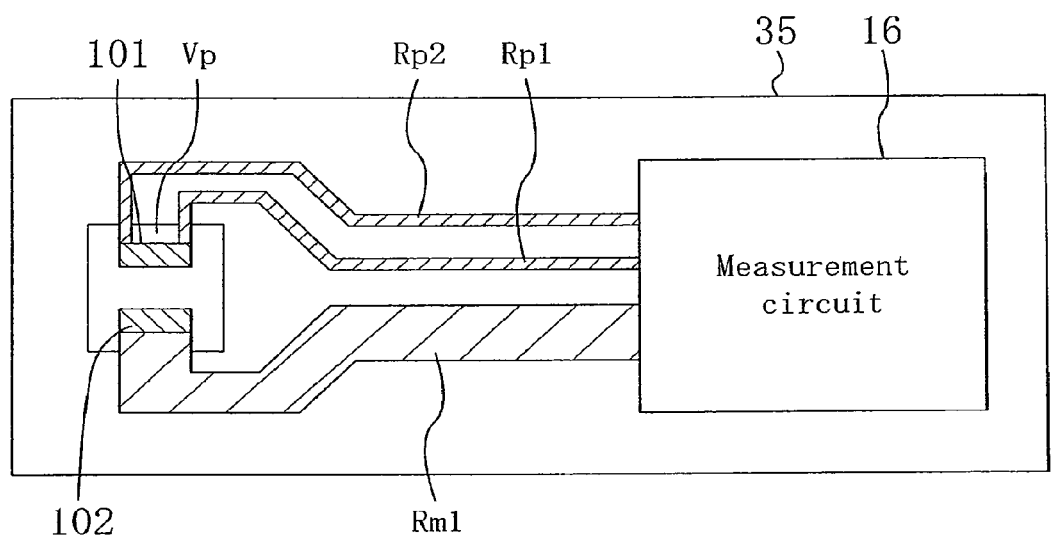
FIG. 15 is a plan view illustrating a biosensor chip of the ninth embodiment of the present invention.
Figure 16:
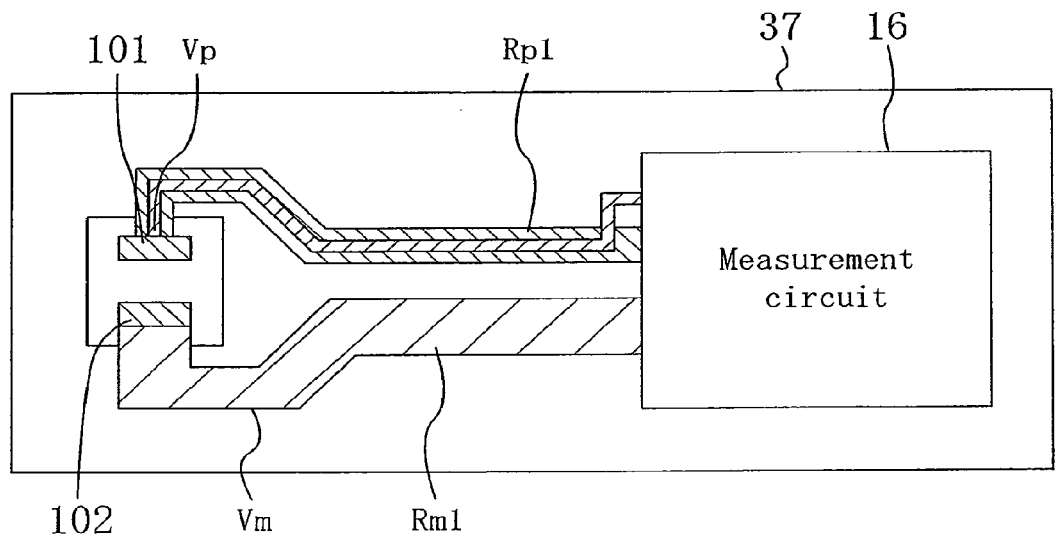
FIG. 16 is a plan view illustrating the first variation of the biosensor chip of the ninth embodiment.
Figure 17:
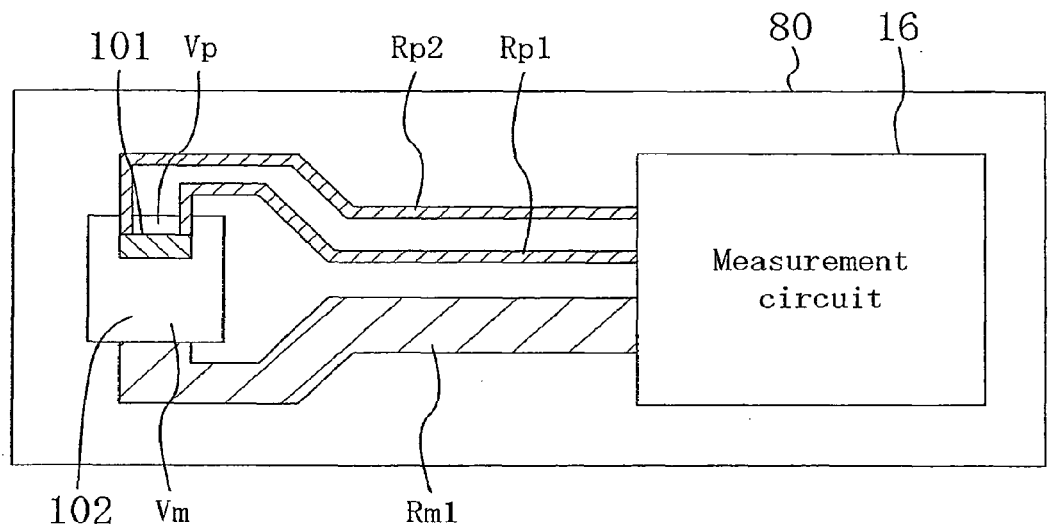
FIG. 17 is a plan view illustrating the second variation of the biosensor chip of the ninth embodiment.
Figure 18:
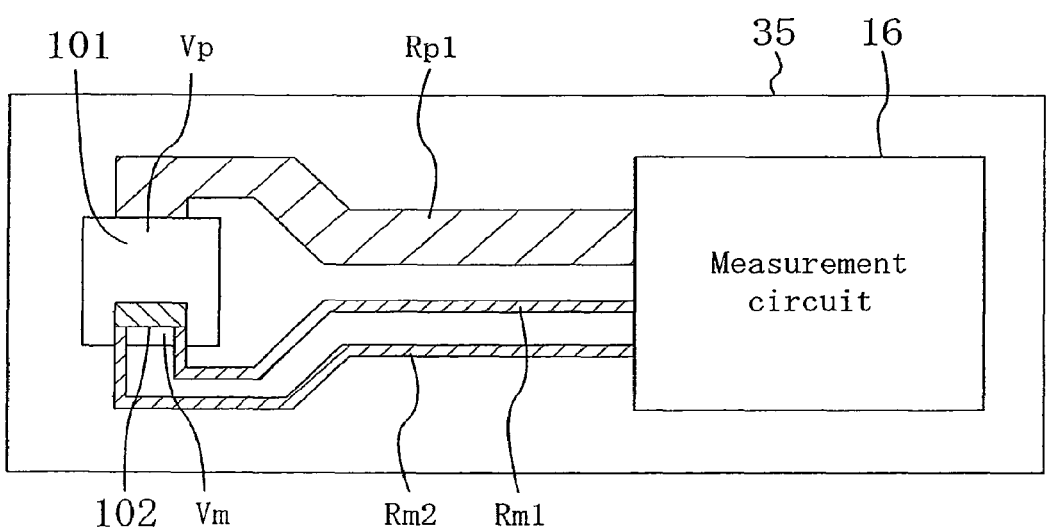
FIG. 18 is a plan view illustrating the third variation of the biosensor chip of the ninth embodiment.

FIG. 15 is a plan view illustrating the biosensor chip of the present embodiment, FIG. 16 is a plan view illustrating the first variation of the biosensor chip of the present embodiment, FIG. 17 is a plan view illustrating the second variation of the biosensor chip of the present embodiment, and FIG. 18 is a plan view illustrating the third variation of the biosensor chip of the present embodiment.

As illustrated in FIG. 15, a biosensor chip 35 of the present embodiment has a structure in which the biosensor of the first embodiment illustrated in FIG. 9 and the measurement circuit 16 are provided on the same substrate. The biosensor and the measurement circuit 16 are manufactured by using a microfabrication technique, and the conductive line connecting the working electrode 101 to the working electrode terminal 103 and the working electrode reference terminal 10 and the conductive line connecting the counter electrode 102 to the counter electrode terminal 104 are formed as thin films. Moreover, the conductive line on the counter electrode side and that on the working electrode side are made of a relatively inexpensive metal such as Al or Cu.

Moreover, the biosensor chip 35 of the present embodiment can be detachable from the device assembly, and is disposable.

Thus, by integrating the biosensor and the measurement circuit 16 together into a single chip, it is possible to reduce the size of the assay section, and it is possible to supply the biosensor chip inexpensively by using known mass-production techniques.

Note that when the conductive lines are formed by using a microfabrication technique, the conductive lines are formed as thin films, thereby increasing the line resistances Rp1, Rm1 and Rp2. However, in the biosensor device of the present invention, a high-precision measurement is realized irrespective of the line resistance, whereby it is possible to realize a biosensor chip that can be used for a high-precision measurement and that is inexpensive. Moreover, since the size is small, the overall size of the biosensor device can be reduced.

Note that not only the biosensor of the first embodiment, but also any other biosensor described above, can be integrated together with the measurement circuit into a chip.

Moreover, in the biosensor chip of the present embodiment, the common substrate to be used may be any substrate, including a semiconductor substrate such as a silicon substrate, an SOI (Silicon on Insulator) substrate, an SOS (Silicon on Sapphire) substrate, an insulative substrate such as a glass substrate, etc. Note however that it is necessary to choose a substrate that does not react with enzymes and reagents applied on the electrodes of the biosensor.

Moreover, a biosensor in which the conductive lines are multilayered as illustrated in FIG. 10 may also be provided on the common substrate with the measurement circuit 16, as illustrated in FIG. 16. By multilayering the conductive lines, the area of the biosensor can be further reduced, whereby it is possible to manufacture an even smaller biosensor chip 37.

Alternatively, the biosensors illustrated in FIG. 11 and FIG. 12 may be provided on the same substrate with the measurement circuit 16, as illustrated in FIG. 17. A biosensor chip 80 of this variation includes a common substrate shared by the measurement circuit 16, and a substrate with a biosensor provided thereon and a substrate with the measurement circuit 16 provided thereon are mounted on the common substrate. A counter electrode terminal is provided so as to extend across the entire reverse surface of the substrate with the biosensor provided thereon.

Moreover, as illustrated in FIG. 18, even a biosensor in which two electrodes, i.e., the counter electrode reference electrode and the counter electrode terminal illustrated in FIG. 13 and FIG. 14, are connected to the counter electrode can be provided on the same common substrate with the measurement circuit 16. Specifically, a substrate with the biosensor provided thereon and a substrate with the measurement circuit 16 provided thereon are mounted on the common substrate.

Tenth Embodiment

Figure 19:
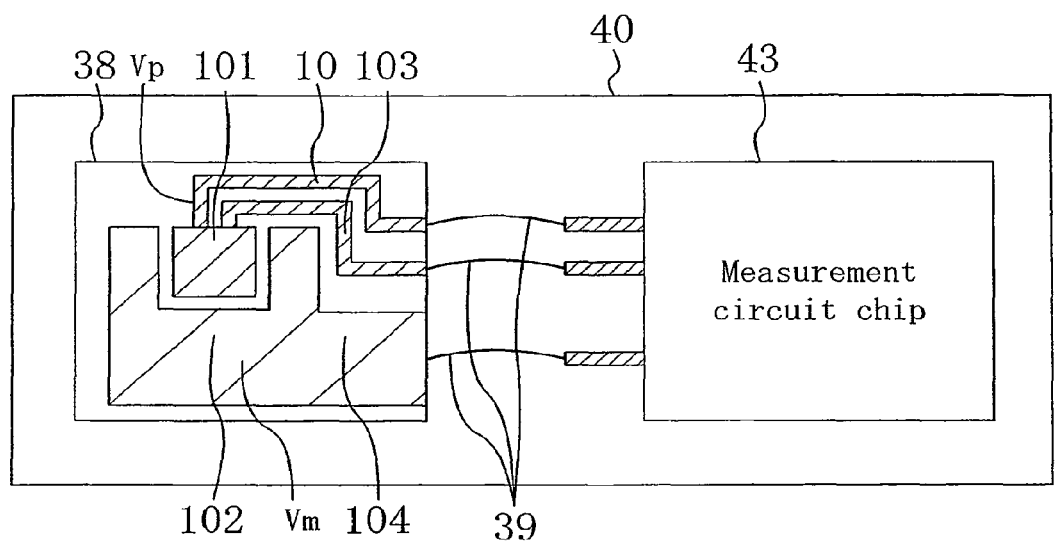
FIG. 19 is a plan view illustrating a biosensor chip of the tenth embodiment of the present invention.
Figure 20:
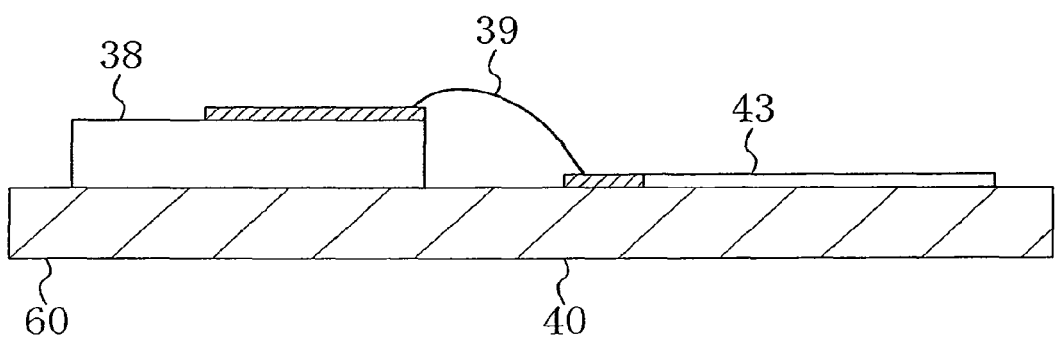
FIG. 20 is a cross-sectional view illustrating the biosensor chip of the tenth embodiment.

FIG. 19 is a plan view illustrating a biosensor chip 40 of the tenth embodiment of the present invention, and FIG. 20 is a cross-sectional view illustrating the biosensor chip 40 of the present embodiment.

As illustrated in FIG. 19 and FIG. 20, the biosensor chip 40 of the present embodiment includes a sensor chip 38 with a 3-electrode biosensor provided thereon, a measurement circuit chip 43 with a measurement circuit provided thereon, and a common substrate 60 supporting the sensor chip 38 and the measurement circuit chip 43. The counter electrode terminal 104, the working electrode terminal 103 and the working electrode reference terminal 10 of the biosensor are connected to the measurement circuit chip 43 by wires 39.

In a case where the substrate with the measurement circuit provided thereon has a poor affinity to, or is reactive with, the assay reagent, etc., in the biosensor including an enzyme and a mediator, it is difficult to provide such a substrate on the same common substrate with the substrate with the measurement circuit 16 provided thereon, as in the biosensor chip illustrated in FIG. 15. Therefore, a chip-on-chip structure is employed, as in the present embodiment. In the biosensor chip 40 of the present embodiment, a substrate with a biosensor provided thereon and a substrate with a measurement circuit provided thereon can be combined arbitrarily.

Moreover, there are cases where the same substance as that of the signal line of the measurement circuit 16 cannot be used for the conductive lines of the biosensor due to the type of the enzyme or mediator corresponding to the assayed component. Also in such a case, a configuration such as that of the present embodiment is useful, and it is possible with such a configuration to realize a sufficiently small biosensor chip.

With a chip-on-chip structure such as that of the present embodiment, any type of biosensor can be made into a small chip. Furthermore, since it does not involve any special processing step, it is possible to realize a low manufacturing cost.

Note that in the biosensor chip of the present embodiment, the sensor chip 38 and the measurement circuit chip 43 are arranged on the common substrate 60. However, the measurement circuit chip 43 may be arranged directly on the sensor chip 38 without using the common substrate 60. Alternatively, the biosensor chip may have a chip-on-chip structure in which the sensor chip 38 is arranged on the measurement circuit chip 43.

Moreover, while the sensor chip and the measurement circuit chip are connected to each other by wires in the present embodiment, the upper surface of the sensor chip and the upper surface of the measurement circuit chip may alternatively be arranged so as to face each other and connected to each other by solder bumps. Moreover, the chips may alternatively be connected to each other by a ball grid array (acronymed to BGA). Alternatively, in a case where a pad or electrode passing through the substrate is provided, chips may be stacked on each other and can still be connected to each other via the through electrode. With these methods, the signal transmission path is shortened, whereby the error may be further reduced.

Eleventh Embodiment

Figure 21:
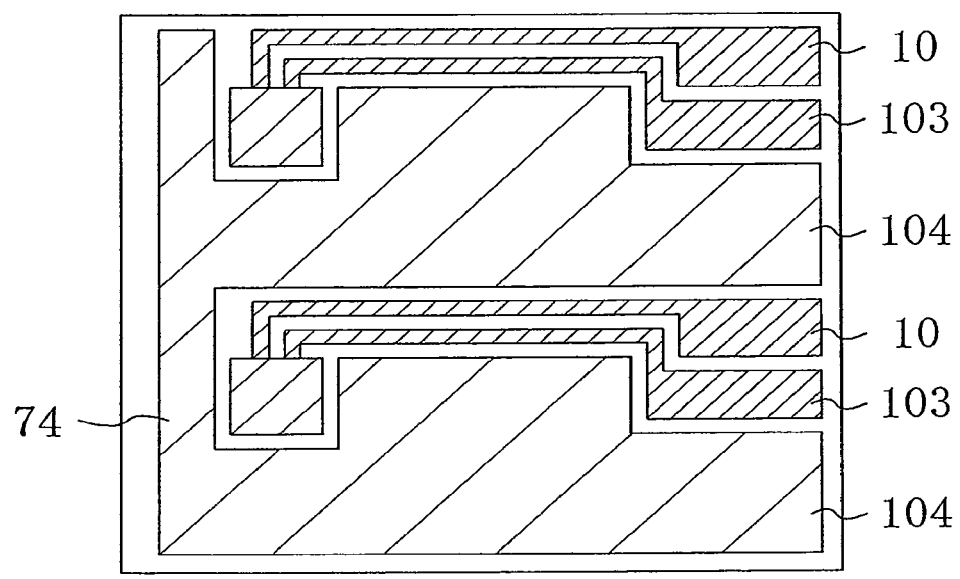
FIG. 21 is a plan view illustrating a biosensor of the eleventh embodiment of the present invention.

FIG. 21 is a plan view illustrating a biosensor of the eleventh embodiment of the present embodiment.

As illustrated in FIG. 21, a biosensor 74 of the present embodiment includes two 3-electrode biosensors formed on the same substrate, each including the working electrode terminal 103, the working electrode reference terminal 10 and the counter electrode terminal 104, such as that described in the first embodiment, for example, wherein the two counter electrode terminals 104 are integrated together into a common terminal. As the two counter electrode terminals 104 are integrated together into a common terminal, the number of electrodes is reduced, whereby it is possible to reduce the size, manufacturing cost, etc., of the biosensor.

Thus, by arranging two biosensors using different assay reagents made of enzymes, mediators, etc., corresponding to different assayed components, it is possible to assay different factors at once, thus making it possible to perform a plurality of tests at the same time and reducing the burden on the patient. The number of types of biosensors to be mounted on a single biosensor device is not limited to any particular number as long as it is two or more. For practical purposes, it is preferred, for example, to make it possible to perform, with a single biosensor chip, a plurality of tests that are necessary for diagnosing a particular disease, or to make it possible to quickly perform a periodic medical examination with a single biosensor chip. For this purpose, three or more biosensors may be formed on the same substrate, although FIG. 21 illustrates an example with only two biosensors formed on the same substrate.

Moreover, the biosensor chip with biosensors mounted thereon is detachable, whereby it is possible to selectively use different biosensor chips according to the purpose of the test while using the same device assembly.

Note that while the counter electrode terminals are integrated together as a common terminal in the biosensor of the present embodiment, any electrodes that can be integrated together may be integrated together into a common electrode. For example, by arranging two 3-electrode biosensors in a symmetrical pattern, adjacent working electrode reference terminals 10 can be integrated together into a common terminal.

Twelfth Embodiment

Figure 22:
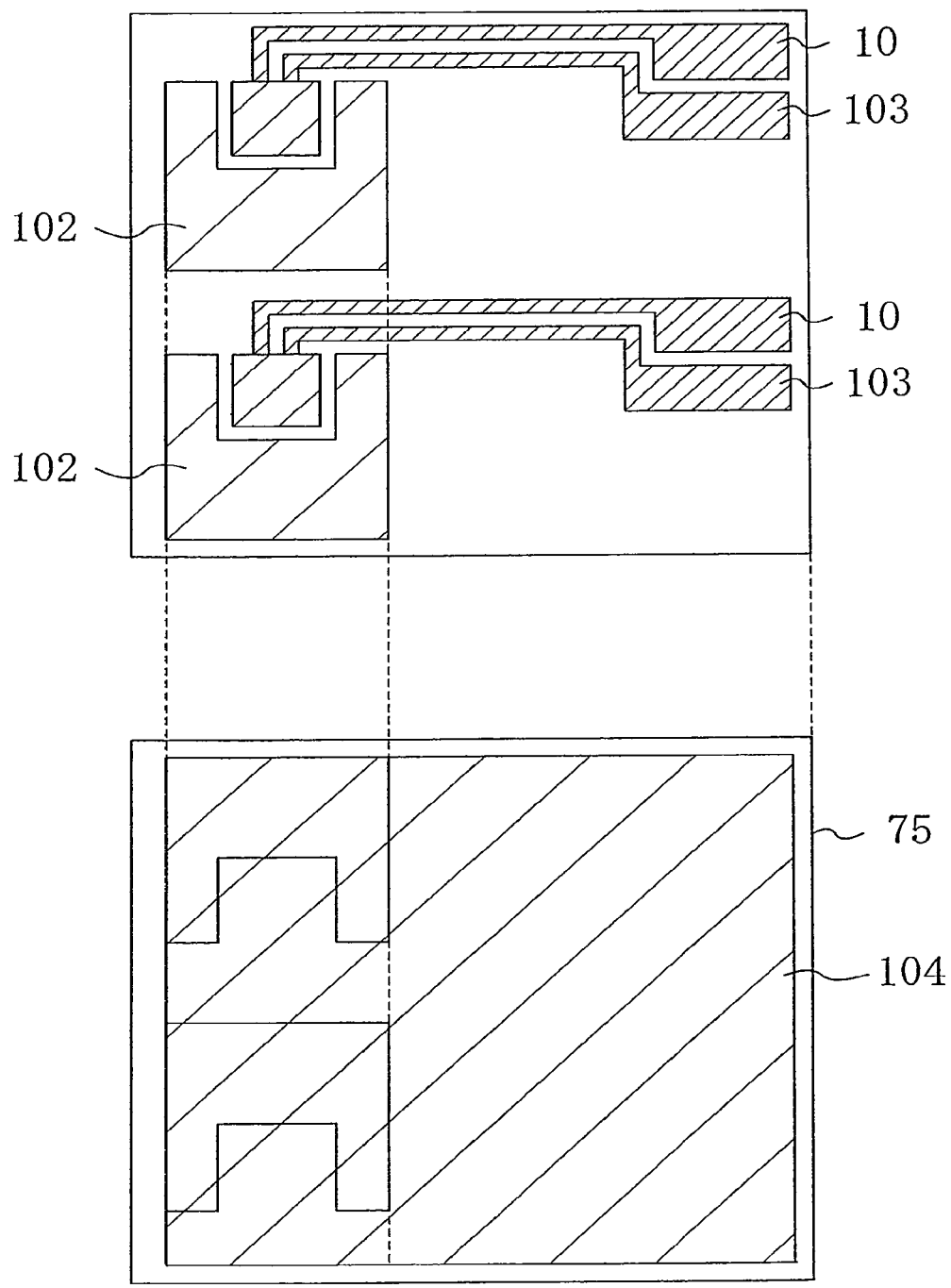
FIG. 22 shows a plan view and a perspective view illustrating a biosensor of the twelfth embodiment of the present invention.

FIG. 22 shows a plan view and a perspective view illustrating a biosensor 75 of the twelfth embodiment of the present invention.

As illustrated in the figure, the biosensor 75 of the present embodiment includes two biosensors of the second embodiment formed on the same substrate, wherein the two counter electrode terminals 104 are integrated together into a common terminal. Thus, a common counter electrode terminal 104 connected to two counter electrodes 102 is provided so as to extend across the entire reverse surface of the biosensor 75.

Also with a biosensor in which the counter electrode terminal is provided so as to extend across the entire reverse surface, two or more biosensors can be arranged together while integrating the counter electrode terminals together into a common terminal, so that it is possible to assay different assayed substances at the same time, while reducing the number of electrodes and reducing the size. Moreover, as the number of electrodes is reduced, the manufacturing process is also simplified. Moreover, by integrating the counter electrode terminals of the biosensors together into a common terminal, it is possible to ensure an even larger area and to bring the resistance value closer to the ideal value of 0Ω.

Note that while two biosensors are arranged together in the present embodiment, three or more biosensors may alternatively be arranged together.

Moreover, also in a case where a plurality of biosensors are arranged together, in each of which the counter electrode is provided so as to extend across the entire upper surface of the substrate as in the fifth embodiment, the counter electrode terminals can be integrated together into a common terminal.

Moreover, also in a case where the conductive lines or electrodes on the counter electrode side or the working electrode side are multilayered, two or more biosensors can be integrated into a single biosensor.

Thirteenth Embodiment

Figure 23:
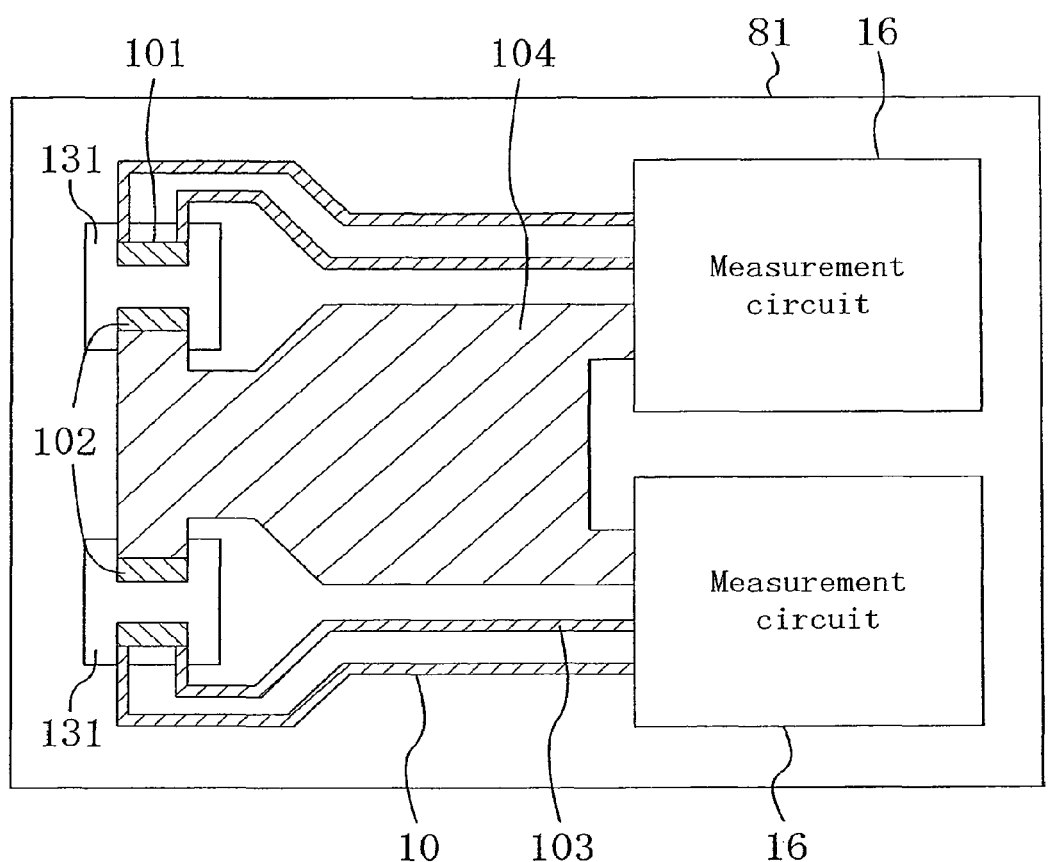
FIG. 23 is a plan view illustrating a biosensor chip of the thirteenth embodiment of the present invention.

FIG. 23 is a plan view illustrating a biosensor chip 81 of the thirteenth embodiment of the present embodiment.

As illustrated in the figure, the biosensor chip 81 of the present embodiment includes two biosensors and the measurement circuits 16 connected to the respective biosensors, the biosensors each including a sensor section 131 having three electrodes, i.e., the working electrode terminal 103, the working electrode reference terminal 10 and the counter electrode terminal 104. The biosensors and the measurement circuits 16 are provided on the same substrate. Moreover, the counter electrode terminals 104 of the adjacent biosensors are integrated together into a common terminal.

Each of the biosensors can assay a different substance, whereby it is possible to perform a plurality of assays at the same time.

Note that while FIG. 23 illustrates an example where each biosensor and the measurement circuit 16 are arranged next to each other, the present invention may employ an alternative structure, e.g., a structure where a chip with a measurement circuit provided thereon is stacked on a biosensor. In such a case, the measurement circuit and the biosensor may be connected to each other by a wire, a BGA or a through electrode passing through the substrate.

Fourteenth Embodiment

Figure 24:
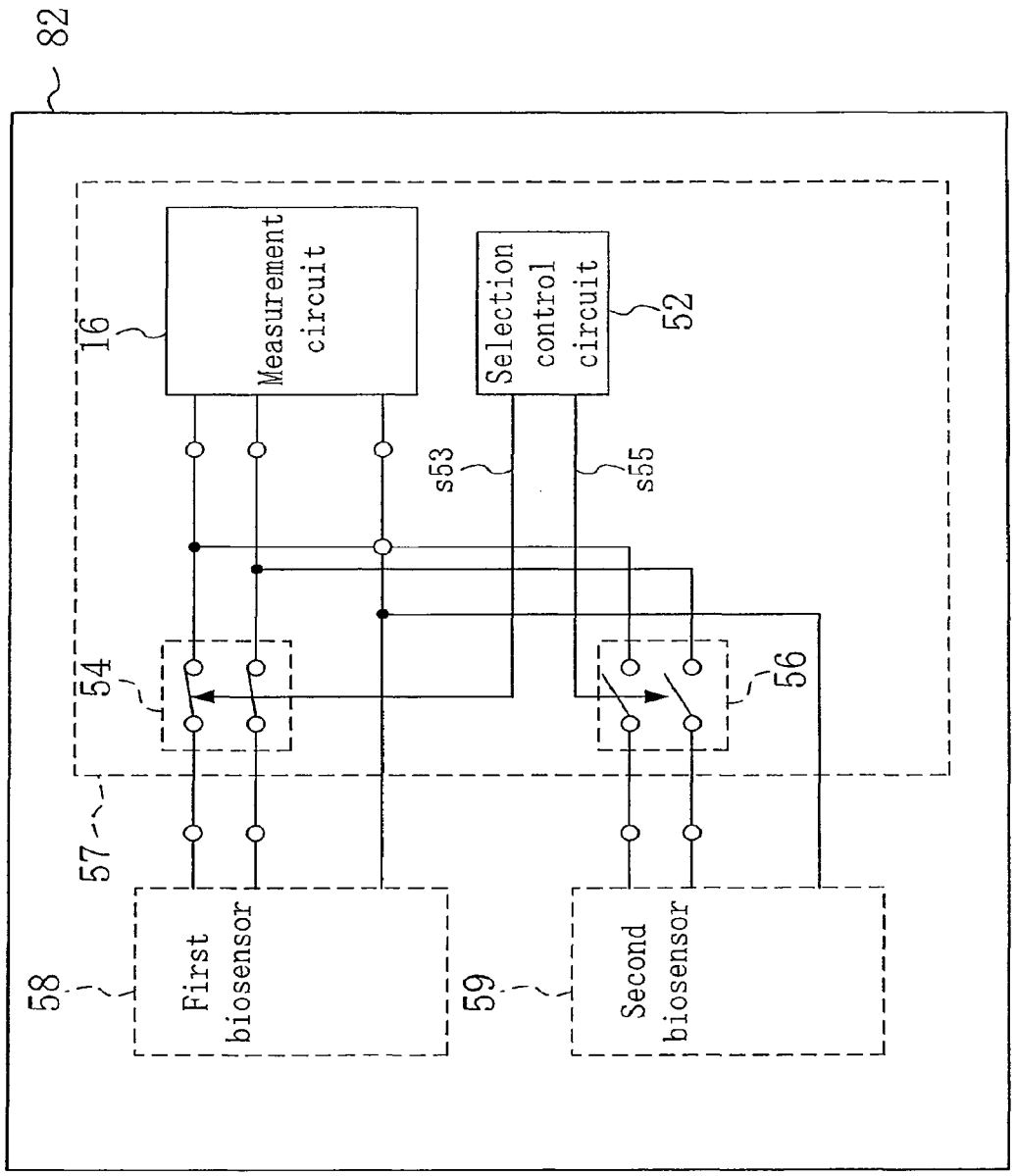
FIG. 24 is a circuit diagram illustrating the configuration of a biosensor chip of the fourteenth embodiment of the present invention.
Figure 25:
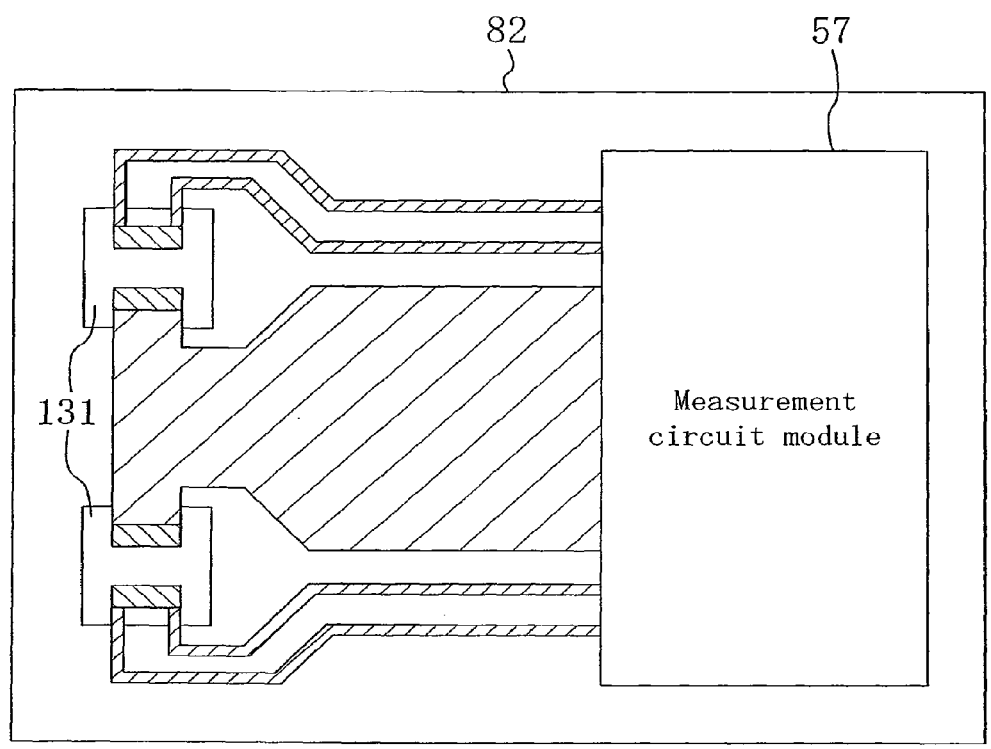
FIG. 25 is a plan view illustrating the biosensor chip of the fourteenth embodiment.

FIG. 24 is a circuit diagram illustrating a biosensor chip 82 of the fourteenth embodiment of the present invention, and FIG. 25 is a plan view illustrating the biosensor chip 82 of the present embodiment.

As illustrated in FIG. 24, the biosensor chip 82 of the present embodiment includes a first biosensor 58, a second biosensor 59, and a measurement circuit module 57 connected to the first biosensor 58 and the second biosensor 59.

As illustrated in FIG. 25, the first biosensor 58 and the second biosensor 59 each include a working electrode terminal, a working electrode reference terminal and a counter electrode, and the counter electrodes of the biosensors are connected to each other.

The measurement circuit module 57 includes the measurement circuit 16 connected to the first biosensor 58 and the second biosensor 59, a first group of switches 54 provided between the working electrode terminal and the working electrode reference terminal of the first biosensor 58 and the measurement circuit 16, a second group of switches 56 provided between the working electrode terminal and the working electrode reference terminal of the second biosensor 59 and the measurement circuit 16, and a selection control circuit 52 for turning ON/OFF the first group of switches 54 and the second group of switches 56.

The selection control circuit 52 supplies a connection control signal s53 to control the switching of the first group of switches 54 and a connection control signal s55 to control the switching of the second group of switches 56. Specifically, when an assay is performed by the first biosensor 58, the first group of switches 54 and the second group of switches 56 are turned ON and OFF, respectively, whereas when an assay is performed by the second biosensor 59, the first group of switches 54 and the second group of switches 56 are turned OFF and ON, respectively.

With the biosensor chip 82 of the present embodiment, an assay can be performed with only one measurement circuit for two biosensors, whereby it is possible to assay a plurality of substances and to further reduce the chip area. Moreover, with this structure, it is possible to reduce the manufacturing cost.

In the biosensor chip of the present embodiment, the first group of switches 54 and the second group of switches 56 may have some on-state resistance. However, since the on-state resistance is equivalently included in the line resistance of the conductive line of the biosensor, the assay precision is not lowered in the present circuit configuration.

Note that two biosensors are formed on the same substrate in the biosensor chip of the present embodiment, three or more biosensors may alternatively be formed on the same substrate. Moreover, since a biosensor to be measured can be selected by a switch, three or more biosensors may be connected to one measurement circuit.

Moreover, while the first biosensor 58, the second biosensor 59 and the measurement circuit module 57 are formed on the same substrate in the present embodiment, chips each having a biosensor or a measurement circuit module thereon may alternatively be mounted on a common substrate.

Alternatively, a plurality of chips may be stacked on one another and connected together by a BGA, a through electrode or a wire.

Note that while the biosensor chip of the present embodiment includes a 3-electrode biosensor having a working electrode terminal, a working electrode reference terminal and a counter electrode terminal, the biosensor chip may alternatively include a 3-electrode biosensor having a working electrode terminal, a counter electrode terminal and a counter electrode reference electrode.

Fifteenth Embodiment

Figure 26:
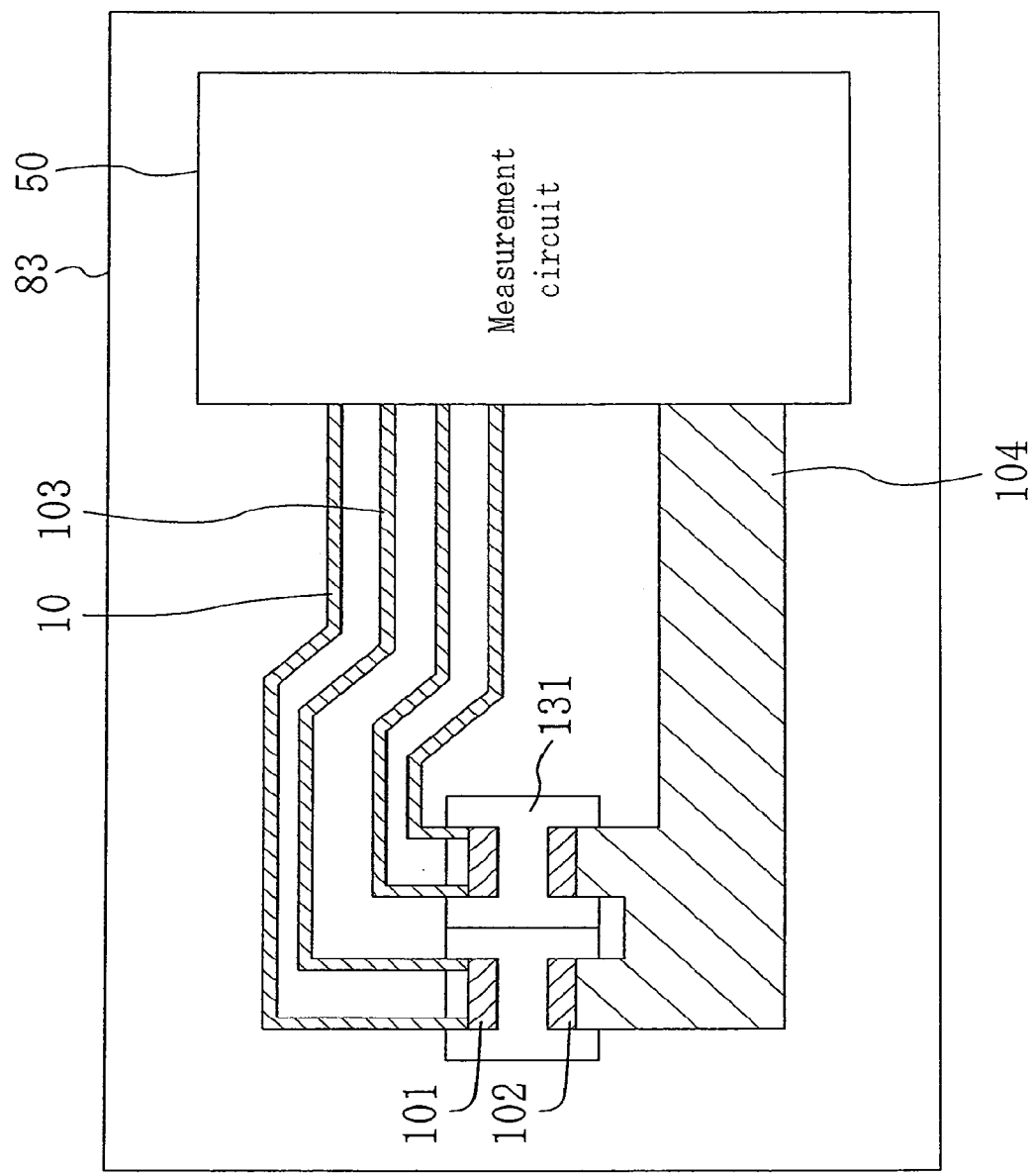
FIG. 26 is a plan view illustrating a biosensor chip of the fifteenth embodiment of the present invention.

FIG. 26 is a plan view illustrating a biosensor chip 83 of the fifteenth embodiment of the present invention.

As illustrated in FIG. 26, the biosensor chip 83 of the present embodiment includes two biosensors and a measurement circuit 50 connected to the two biosensors on the same substrate, each biosensor including the working electrode terminal 103, the working electrode reference terminal 10, the counter electrode terminal 104, and the sensor section 131 for reacting an assayed fluid.

A feature of the biosensor chip 83 of the present embodiment is that the sensor sections 131 of the biosensors corresponding to different assayed components are provided adjacent to each other. The reaction section includes a counter electrode and a working electrode on which an assay reagent made of an enzyme, a mediator, etc., is applied.

In the biosensor chip of the present embodiment, the reaction sections of the two biosensors are adjacent to each other, whereby two different assays can be performed only by dripping a single drop of blood sample. Thus, the structure of the dripping section of the biosensor is simplified. Moreover, it requires a very small amount of blood sample, thereby imposing a very little burden on the subject for blood collection.

Note that in the biosensor chip of the present embodiment, reaction sections of three or more different biosensors may alternatively be provided adjacent to one another. Then, it is possible to perform three or more different assays with a simple dripping section structure. Moreover, it is possible to reduce the amount of blood sample required.

Sixteenth Embodiment

While the embodiments described above are directed to a biosensor including three terminals, and a biosensor chip and a biosensor device having the same, this and subsequent embodiments are directed to examples where the biosensor includes four terminals.

Figure 27:
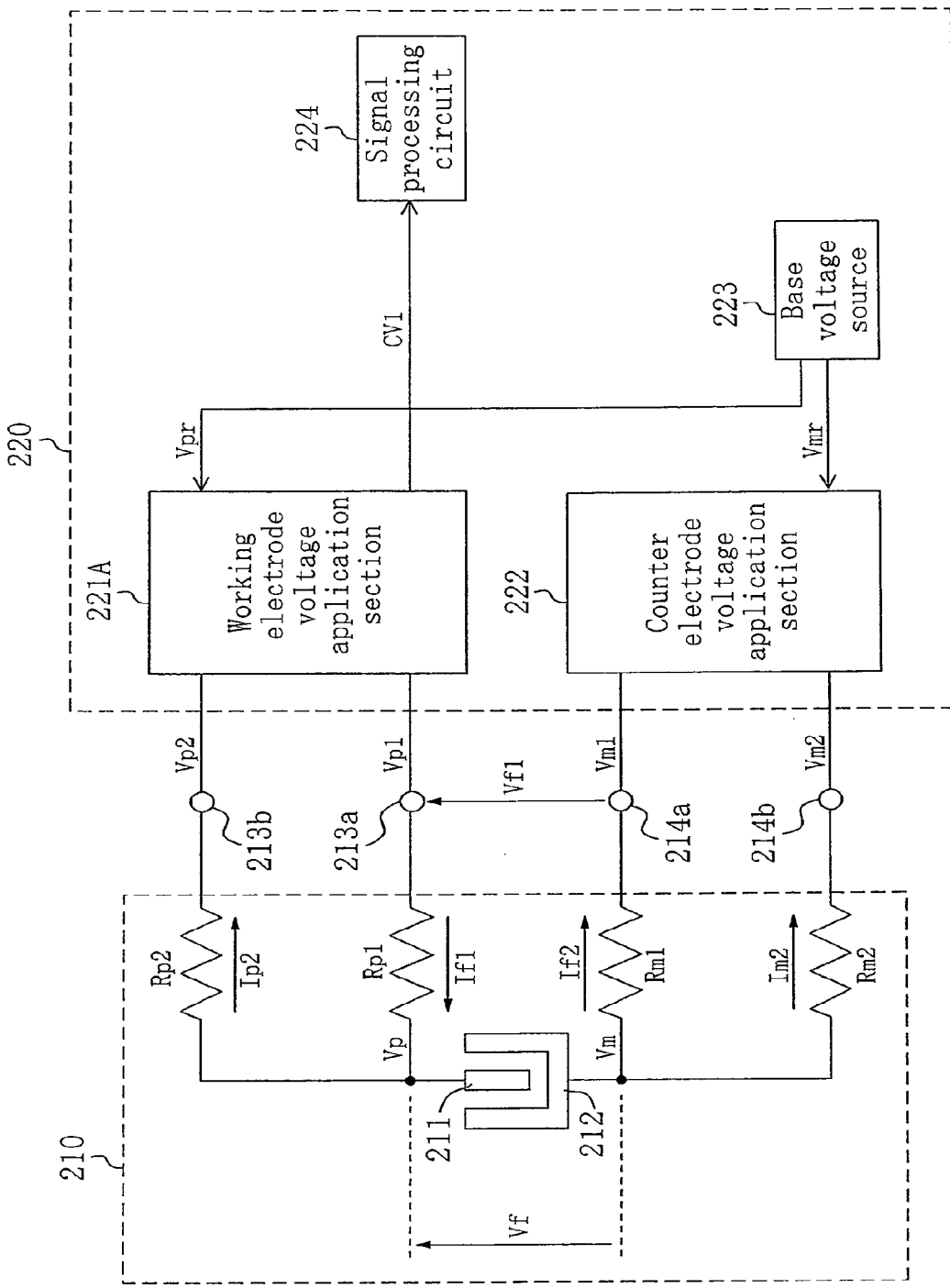
FIG. 27 is a circuit configuration diagram illustrating a biosensor device of the sixteenth embodiment of the present invention.
Figure 28:
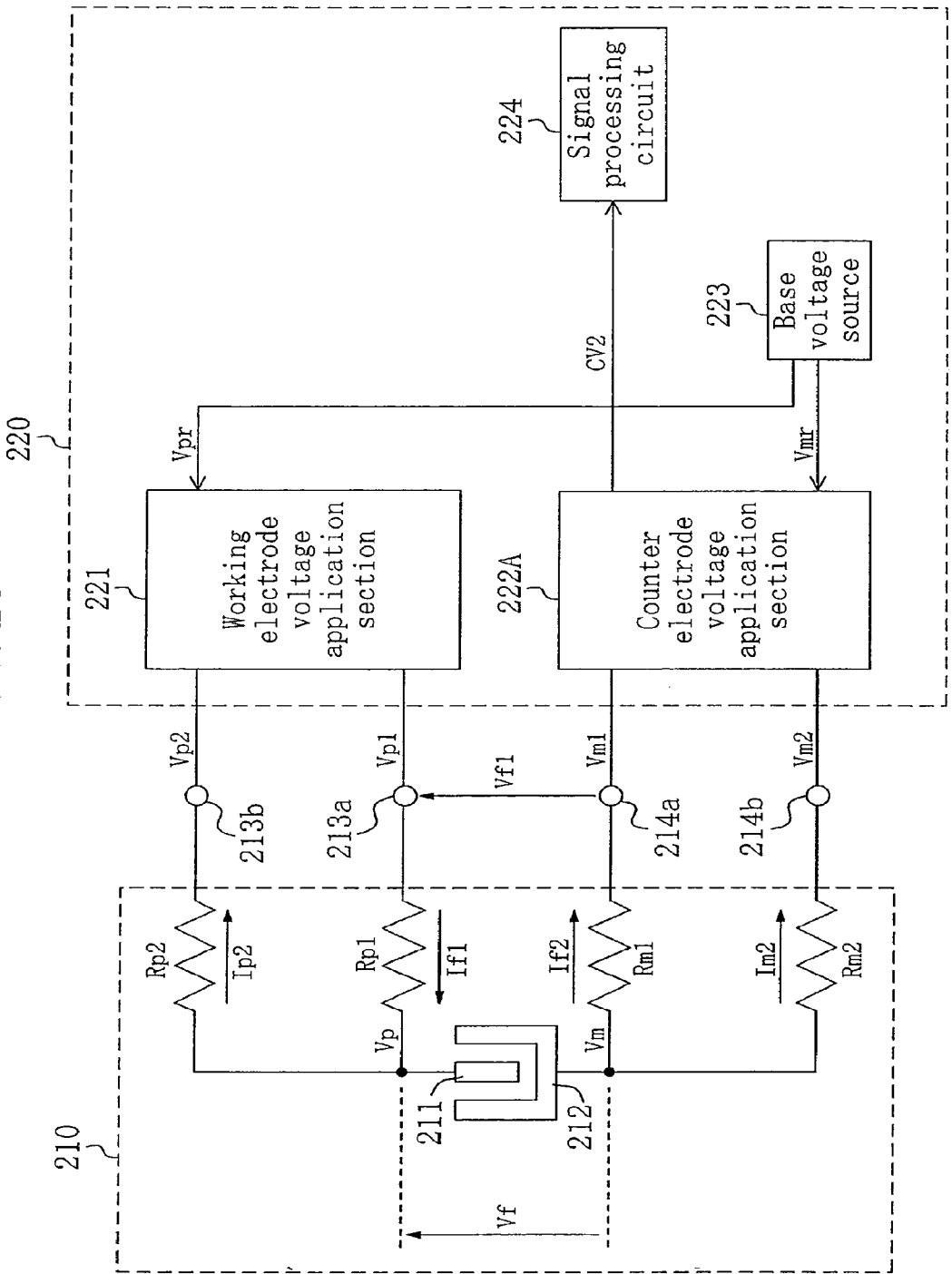
FIG. 28 is a circuit configuration diagram illustrating the biosensor device of the sixteenth embodiment of the present invention.

FIG. 27 and FIG. 28 each show a circuit configuration of a biosensor device of the sixteenth embodiment of the present invention. The biosensor device illustrated in these figures includes a biosensor 210 of the present invention attached thereto, wherein a measurement circuit 220 and the biosensor 210 are electrically connected to each other. The structure of the biosensor 210 will be described later. Note that in addition to the biosensor 210 and the measurement circuit 220 as described herein, the biosensor device includes a data analysis device, an assay result display section, etc., as necessary.

The measurement circuit 220 illustrated in FIG. 27 includes a working electrode voltage application section 221A for applying the voltage Vp1 (corresponding to the "first working electrode voltage" of the present invention) to a working electrode terminal 213a (corresponding to the "first working electrode terminal" of the present invention) of the biosensor 210, a counter electrode voltage application section 222 for applying the voltage Vm1 (corresponding to the "first counter electrode voltage" of the present invention) to a counter electrode terminal 214a (corresponding to the "first counter electrode terminal" of the present invention) of the biosensor 210, a base voltage source 223 for supplying a voltage Vpr (corresponding to the "working electrode base voltage" of the present invention) and a voltage Vmr (corresponding to the "counter electrode base voltage" of the present invention) to the working electrode voltage application section 221A and the counter electrode voltage application section 222, respectively, and a signal processing circuit 224 for processing a working electrode current level signal CV1 output from the working electrode voltage application section 221A.

On the other hand, the measurement circuit 220 illustrated in FIG. 28 includes a working electrode voltage application section 221 and a counter electrode voltage application section 222A instead of the working electrode voltage application section 221A and the counter electrode voltage application section 222, respectively, and the signal processing circuit 224 processes a counter electrode current level signal CV2 output from the counter electrode voltage application section 222A.

The working electrode voltage application section 221 references the voltage Vp2 of a working electrode reference terminal 213b of the biosensor 210. The working electrode voltage application section 221 only references the voltage Vp2, and the input impedance is high, whereby the current Ip2 flowing through the working electrode reference terminal 213b is substantially zero. Therefore, there is no voltage drop due to the resistance value Rp2 of the working electrode reference terminal 213b, and the voltage Vp2 and the voltage Vp (corresponding to the "second working electrode voltage" of the present invention) can be considered to be equal to each other. Thus, essentially, the working electrode voltage application section 221 references the voltage Vp of a working electrode 211 via the working electrode reference terminal 213b, and generates the voltage Vp1 so that the voltage Vp is matched with the given voltage Vpr.

In addition to the function of the working electrode voltage application section 221 described above, the working electrode voltage application section 221A has a function of measuring the working electrode current If1 flowing through the working electrode terminal 213a, and it outputs the working electrode current level signal CV1 according to the measured level of the working electrode current If1.

The counter electrode voltage application section 222 references the voltage Vm2 of a counter electrode terminal 214b (corresponding to the "second counter electrode terminal" of the present invention) of the biosensor 210. The counter electrode voltage application section 222 only references the voltage Vm2, and the input impedance is high, whereby a current Im2 flowing through the counter electrode terminal 214b is substantially zero. Therefore, there is no voltage drop due to a resistance value Rm2 of the counter electrode terminal 214b, and the voltage Vm2 and a voltage Vm (corresponding to the "second counter electrode voltage" of the present invention) can be considered to be equal to each other. Thus, essentially, the counter electrode voltage application section 222 references the voltage Vm of a counter electrode 212 via the counter electrode terminal 214b, and generates the voltage Vm1 so that the voltage Vm is matched with the given voltage Vmr.

In addition to the function described above, the counter electrode voltage application section 222A has a function of measuring the counter electrode current If2 flowing through the counter electrode terminal 214a, and it outputs the counter electrode current level signal CV2 according to the measured level of the counter electrode current If2.

FIG. 29 shows some circuit examples of the working electrode voltage application sections 221 and 221A and the counter electrode voltage application sections 222 and 222A. The configurations of the circuits illustrated in the figure will now be described successively.

Figure 29A:
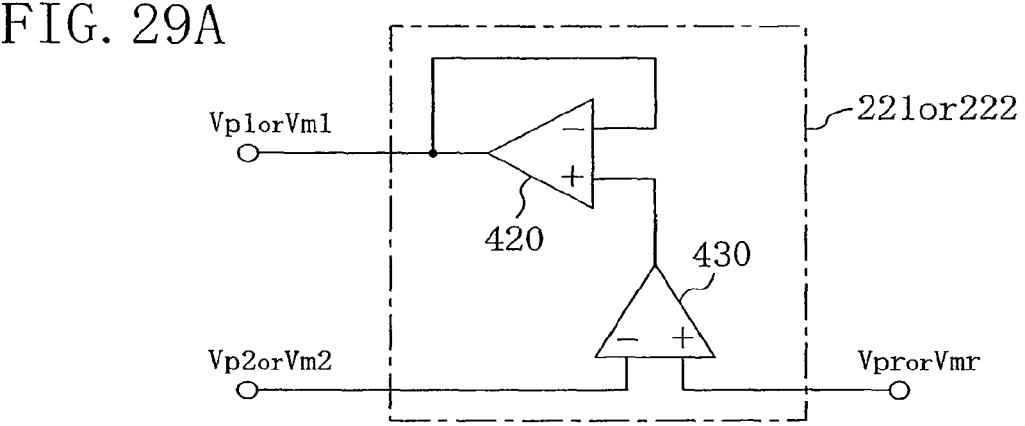
FIGS. 29A-C show circuit diagrams each illustrating a working electrode voltage application section and a counter electrode voltage application section in the biosensor device of the sixteenth embodiment.
Figure 44:
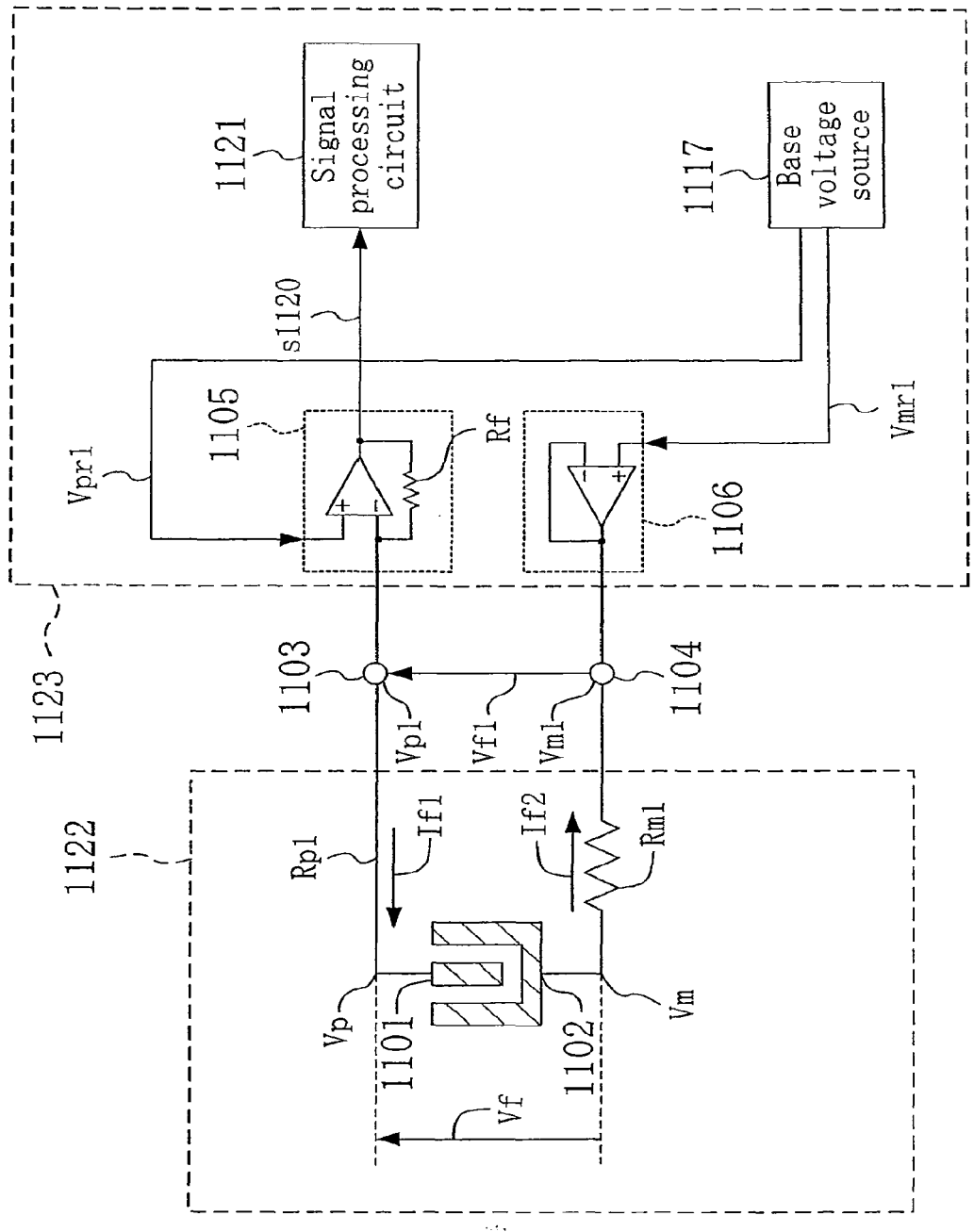
FIG. 44 is a circuit diagram illustrating a portion of the conventional biosensor device including specific circuit configuration examples of the working electrode voltage application section and the counter electrode voltage application section.
Figure 45:
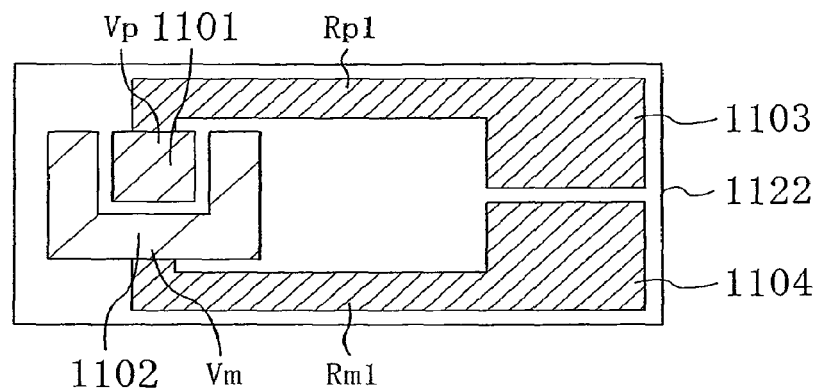
FIG. 45 is a plan view illustrating the structure of a conventional biosensor.
Figure 46:
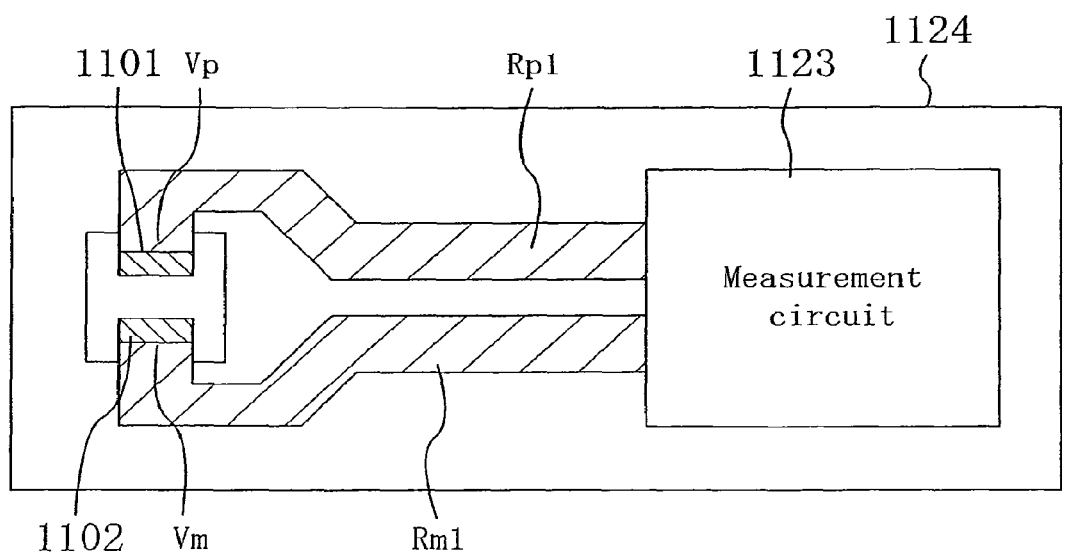
FIG. 46 is a plan view illustrating the structure of the biosensor chip in the conventional biosensor device illustrated in FIG. 44.

FIG. 29(a) shows a circuit example of the working electrode voltage application section 221 or the counter electrode voltage application section 222. The working electrode voltage application section 221 or the counter electrode voltage application section 222 illustrated in the figure has a configuration in which the output of a voltage reference circuit 430, instead of the voltage Vpr or the voltage Vmr, is given to a counter electrode side voltage source 1106 of the conventional measurement circuit 1123 illustrated in FIG. 44. The working electrode voltage application section 221 will now be described as an example.

The voltage reference circuit 430 is an operational amplifier whose inverting input terminal and non-inverting input terminal are given the voltages Vp2 and Vpr, respectively. The voltage reference circuit 430 outputs a voltage so that the voltage Vp2 and the voltage Vpr are equal to each other. An operational amplifier being a voltage source 420 receives this voltage as its input, and outputs the voltage Vp1 corresponding to the input voltage.

Figure 29B:
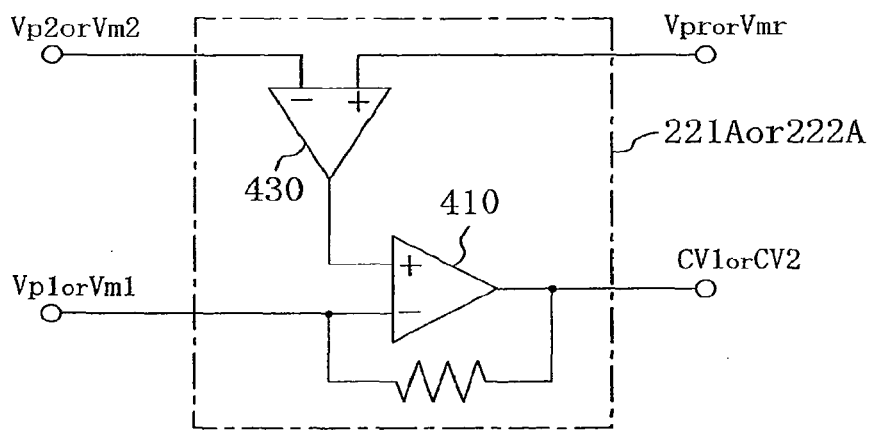

FIG. 29(b) shows a circuit example of the working electrode voltage application section 221A or the counter electrode voltage application section 222A. The working electrode voltage application section 221A or the counter electrode voltage application section 222A illustrated in the figure has a configuration in which the output of the voltage reference circuit 430, instead of the voltage Vpr1 or the voltage Vmr1, is given to the voltage source 210 in the conventional biosensor device illustrated in FIG. 44. The working electrode voltage application section 221A will now be described as an example.

An operational amplifier being the voltage reference circuit 430 outputs a voltage so that its inputs, i.e., the voltage Vp2 and the voltage Vpr, are equal to each other. The output voltage is given to the non-inverting input terminal of the operational amplifier being the voltage source 420. A resistive element is provided in the negative feedback section of the operational amplifier, whereby the working electrode current level signal CV1 according to the level of the working electrode current If1 flowing through the resistive element is output.

Figure 29C:
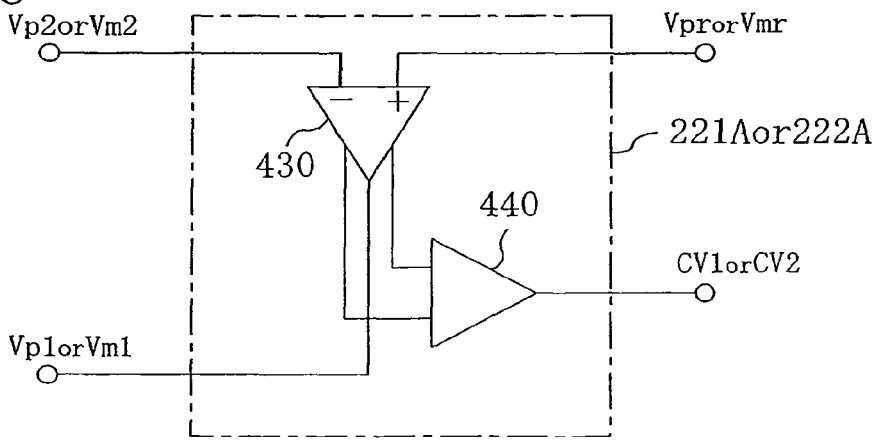

FIG. 29(c) shows a circuit example of the working electrode voltage application section 221A or the counter electrode voltage application section 222A. The working electrode voltage application section 221A or the counter electrode voltage application section 222A illustrated in the figure includes the voltage reference circuit 430 and a voltage-current conversion circuit 440. This circuit has a similar configuration to that of the voltage-current conversion circuit disclosed in Japanese Laid-Open Patent Publication No. 11-154833 or U.S. Pat. No. 5,986,910, for example. The working electrode voltage application section 221A will now be described as an example.

The voltage reference circuit 430 outputs the voltage Vp1 so that its inputs, i.e., the voltage Vp2 and the voltage Vpr, are equal to each other. The voltage-current conversion circuit 440 receives as its input a signal for controlling the output of the voltage reference circuit 430, and outputs the working electrode current level signal CV1.

Next, the voltage applied to the biosensor 210 by the measurement circuit 220 of the present embodiment, and the current measured by the measurement circuit 220 will be described.

The voltage Vp1 is generated by the working electrode voltage application section 221 or 221A so that the voltage Vp and the voltage Vpr are matched with each other, and the voltage Vp1 is applied to the working electrode terminal 213a. In this way, even if a voltage drop occurs due to the resistance value Rp1 of the working electrode terminal 213a, the voltage Vp can be fixed to the voltage Vpr.

Similarly, the voltage Vm1 is generated by the counter electrode voltage application section 222 or 222A so that the voltage Vm and the voltage Vmr are matched with each other, and the voltage Vm1 is applied to the counter electrode terminal 214a. In this way, even if a voltage drop occurs due to the resistance value Rm1 of the counter electrode terminal 214a, the voltage Vm can be fixed to the voltage Vmr.

Therefore, the voltage Vf applied by the measurement circuit 220 between the working electrode 211 and the counter electrode 212 of the biosensor 210 is as shown in Expression (35) below.

$$Vf=(Vpr-Vmr) \tag{35}$$

Then, from Expression (8) and Expression (35), a current If flowing through the biosensor 210 in response to the voltage application is as shown in Expression (36) below.

$$If=f\{Q,Vpr-Vmr\} \tag{36}$$

Comparing Expression (35) and Expression (7) with each other shows that there is no voltage drop due to the line resistances Rp1 and Rm1 of the working electrode terminal 213a and the counter electrode terminal 214a in Expression (35). Thus, the voltage Vf applied between the working electrode 211 and the counter electrode 212 can be set to a predetermined value irrespective of the line resistances of the working electrode terminal 213a and the counter electrode terminal 214a of the biosensor 210. Therefore, no error is contained in the current flowing through the biosensor 210. The current is measured as the working electrode current If1 or the counter electrode current If2 by the working electrode voltage application section 221A or the counter electrode voltage application section 222A, and converted to the working electrode current level signal CV1 or the counter electrode current level signal CV2. The working electrode current level signal CV1 or the counter electrode current level signal CV2 is processed by the signal processing circuit 224 to calculate the concentration of the assayed chemical substance.

As described above, according to the present embodiment, it is possible to apply a predetermined voltage Vf between the working electrode 211 and the counter electrode 212 irrespective of the line resistances of the working electrode terminal 213a and the counter electrode terminal 214a of the biosensor 210. Thus, it is possible to measure an accurate current level with no error, thereby improving the assay precision of the biosensor device. Particularly, in the biosensor device of the present embodiment, the working electrode reference terminal 213b and the counter electrode reference terminal 214b are provided, whereby it is possible to further improve the assay precision as compared with a case where only one of the reference terminals is provided.

Note that in the working electrode voltage application section 221 or the counter electrode voltage application section 222 illustrated in FIG. 29(a), the voltage source 420 may be omitted and the output of the voltage reference circuit 430 may be used directly as the voltage Vp1 or the voltage Vm1. Moreover, the voltage source 420 and the voltage reference circuit 430 may be implemented as an element other than an operational amplifier. Such a change does not at all detract from the effects of the present invention.

Moreover, where one of the working electrode 211 and the counter electrode 212 is a first electrode and the other is a second electrode, the first voltage application section for applying the first voltage (e.g., the voltage Vp1) to the first terminal (e.g., the working electrode terminal 213a) connected to the first electrode (e.g., the working electrode 211) is a conventional voltage application section, while the second voltage application section for applying the second voltage (e.g., the voltage Vm1) to the second terminal (e.g., the counter electrode terminal 214a) connected to the second electrode (e.g., the counter electrode 212) is a voltage application section of the present embodiment (e.g., the counter electrode voltage application section 222). The second voltage application section references the third voltage (e.g., the voltage Vm) of the second electrode via the third terminal (e.g., the counter electrode terminal 214b) connected to the second electrode, and generates the second voltage so that the third voltage and a given base voltage (e.g., the voltage Vmr) are matched with each other. Thus, even when one of the working electrode voltage application section 221 or 221A and the counter electrode voltage application section 222 or 222A is omitted, it is possible to realize a biosensor device with an improved precision over the prior art.

Seventeenth Embodiment

Figure 30:
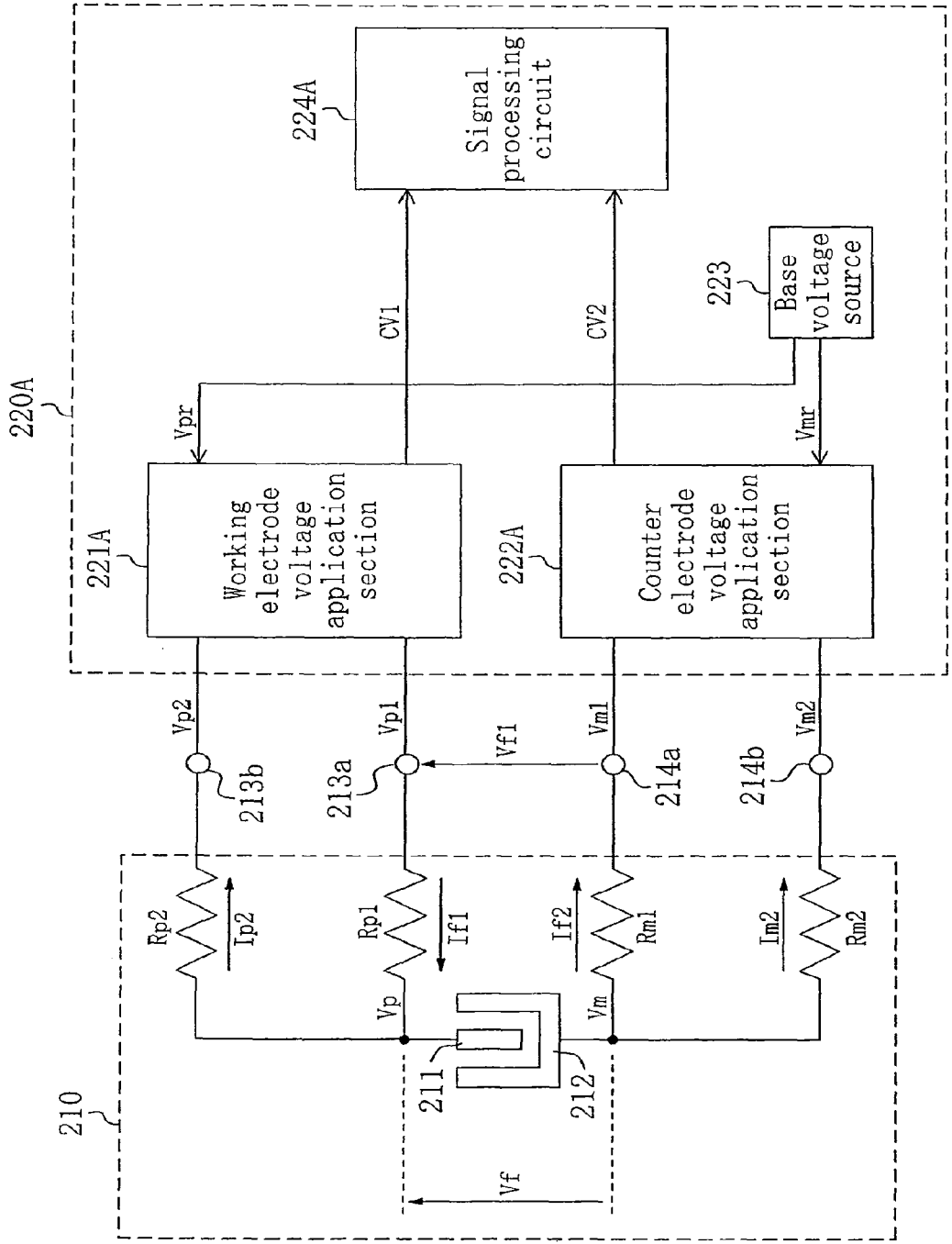
FIG. 30 is a circuit configuration diagram illustrating a biosensor device of the seventeenth embodiment of the present invention.

FIG. 30 shows a circuit configuration of a biosensor device of the seventeenth embodiment of the present invention. A measurement circuit 220A of the present embodiment includes the working electrode voltage application section 221A and the counter electrode voltage application section 222A described in the sixteenth embodiment as means for applying a voltage to the working electrode terminal 213a and the counter electrode terminal 214a, respectively, of the biosensor 210, and processes the working electrode current level signal CV1 and the counter electrode current level signal CV2 output from the voltage application sections to analyze the assayed chemical substance. The measurement circuit 220A will now be described, where what has already been described in the sixteenth embodiment will not be described again, and the same reference numerals as those used in FIG. 27 and FIG. 28 will be used.

The working electrode voltage application section 221A measures the current If1 flowing through the working electrode terminal 213a as the current flowing through the biosensor 210, and outputs the working electrode current level signal CV1. The working electrode voltage application section 221A may employ various configurations other than those of the circuits illustrated in FIG. 29(b) and FIG. 29(c).

The counter electrode voltage application section 222A measures the current If2 flowing through the counter electrode terminal 214a as the current flowing through the biosensor 210, and outputs the counter electrode current level signal CV2. The counter electrode voltage application section 222A may employ various configurations other than those of the circuits illustrated in FIG. 29(b) and FIG. 29(c).

A signal processing circuit 224A processes the working electrode current level signal CV1 and the counter electrode current level signal CV2. While the signal to be processed is either the working electrode current level signal CV1 or the counter electrode current level signal CV2 in the sixteenth embodiment, these signals are both used in the present embodiment, thereby doubling the amount of information on the current flowing through the biosensor 210. Therefore, the S/N ratio can be improved by about 6 db over the sixteenth embodiment.

As described above, according to the present embodiment, the assay precision of the biosensor device can be further improved (by about 6 db in terms of S/N ratio). Moreover, processing both the working electrode current level signal CV1 and the counter electrode current level signal CV2 provides an effect of reducing the common-mode noise.

Eighteenth Embodiment

Figure 31:
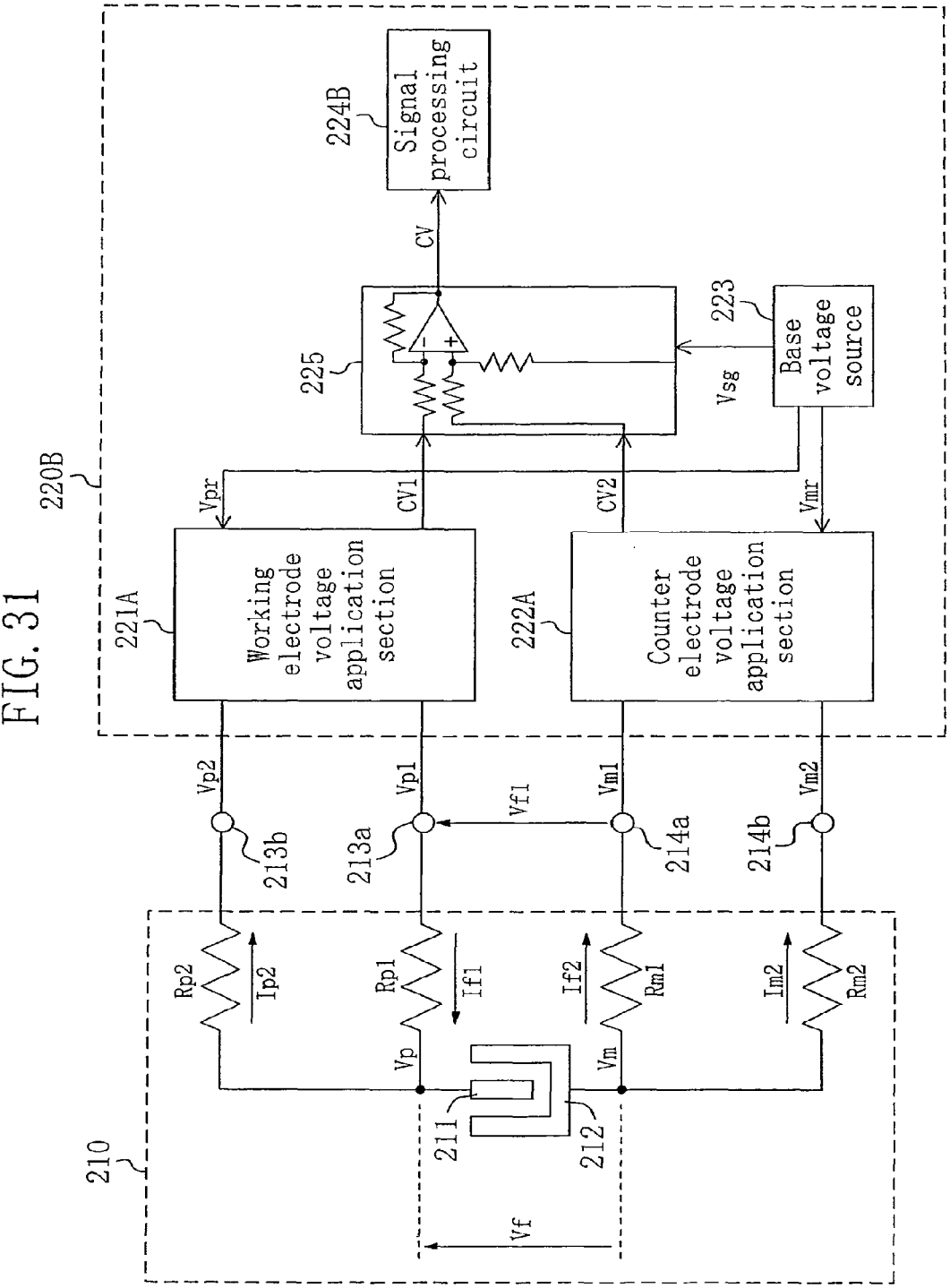
FIG. 31 is a circuit configuration diagram illustrating a biosensor device of the eighteenth embodiment of the present invention.

FIG. 31 shows a circuit configuration of a biosensor device of the eighteenth embodiment of the present invention. A measurement circuit 220B of the present embodiment is similar to the measurement circuit 220A of the seventeenth embodiment, but further includes a current level signal generation section 225. The measurement circuit 220B will now be described, where what has already been described in the seventeenth embodiment will not be described again, and the same reference numerals as those used in FIG. 30 will be used.

The current level signal generation section 225 receives, as its inputs, the working electrode current level signal CV1 and the counter electrode current level signal CV2, and outputs a current level signal CV representing the level of the current flowing through the biosensor 210. The current level signal generation section 225 can be implemented as a differential signal converter, for example, as illustrated in FIG. 31. The differential signal converter adds together two input signals to output one signal. Thus, in the present embodiment, the current level signal CV is the result of adding together the working electrode current level signal CV1 and the counter electrode current level signal CV2.

A signal processing circuit 224B is substantially the same in structure as the signal processing circuit 224 in the measurement circuit 220 of the sixteenth embodiment, and receives the current level signal CV as its input to calculate the concentration of the assayed chemical substance.

As described above, according to the present embodiment, the working electrode current level signal CV1 and the counter electrode current level signal CV2 are converted by the current level signal generation section 225 into a single current level signal CV, whereby the configuration of the signal processing circuit 224B can be simplified as compared with that of the seventeenth embodiment. Thus, it is possible to reduce the size and the cost of the biosensor device. Note that the current level signal generation section 225 can be implemented as an element other than the differential signal converter illustrated in FIG. 31.

Nineteenth Embodiment

Figure 32:
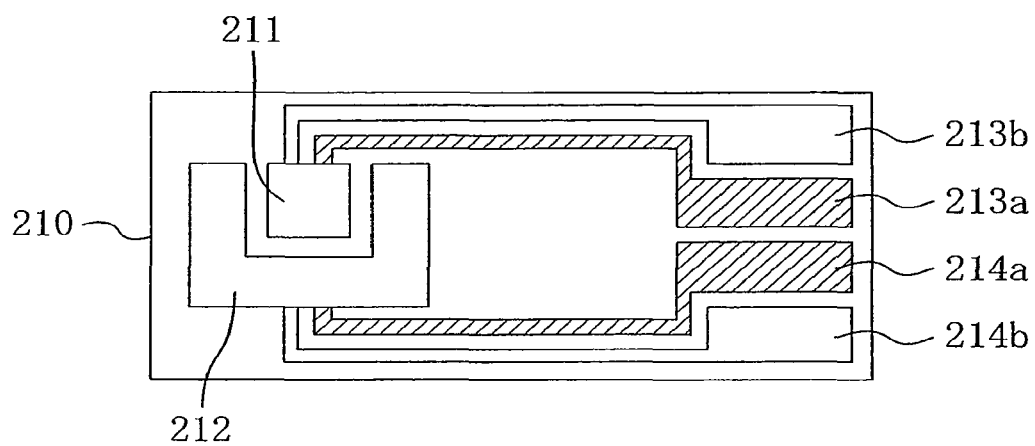
FIG. 32 is a plan view illustrating a biosensor of the nineteenth embodiment of the present invention.

FIG. 32 illustrates the structure of a biosensor of the nineteenth embodiment of the present invention. The biosensor 210 of the present embodiment is used by the measurement circuits 220, 220A and 220B of the first to eighteenth embodiments described above, for example.

The biosensor 210 includes the working electrode terminal 213a, 13b extending from the working electrode 211, and the counter electrode terminal 214a and the counter electrode reference terminal 214b extending from the counter electrode 212. Although not shown in the figure, an assay reagent made of an enzyme, a mediator, etc., according to the assayed chemical substance is applied on the sensor section including the combination of the working electrode 211 and the counter electrode 212. With the biosensor 210, it is possible to electronically detect the binding reaction between a pair of chemical substances, such as an oligonucleotide, an antigen, an enzyme, a peptide, an antibody, a DNA fragment, an RNA fragment, glucose, lactic acid and cholesterol, or between molecular structures thereof.

The working electrode terminal 213a is a terminal for voltage application from the measurement circuit (device assembly), and the working electrode reference terminal 213b is an electrode for referencing the voltage. Note however that the position of the working electrode terminal 213a and that of the working electrode reference terminal 213b may be switched around.

Similarly, the counter electrode terminal 214a is a terminal for voltage application from the measurement circuit, and the counter electrode reference terminal 214b is a terminal for referencing the voltage. Again, the positions of the terminals may be switched around.

As a voltage is applied between the working electrode terminal and the counter electrode terminal, the biosensor 210 outputs a current according to the concentration of a particular chemical substance contained in the body fluid such as blood placed on the sensor section. Then, the voltage at the working electrode 211 and the voltage at the counter electrode 212 can be known by referencing the voltage at the working electrode reference terminal and the voltage at the counter electrode reference terminal, respectively.

As described above, according to the present embodiment, the working electrode terminal 213a, the working electrode reference terminal 213b, the counter electrode terminal 214a and the counter electrode reference terminal 214b are provided in the biosensor 210, whereby it is possible to adjust the voltages applied to the working electrode 211 and the counter electrode 212 while referencing the voltages at the working electrode 211 and the counter electrode 212, and thus it is possible to control the voltage applied between the working electrode 211 and the counter electrode 212 to a predetermined value. Thus, it is possible to eliminate the current error due to the line resistance without using a low-resistance noble metal for the lines connected to the working electrode terminal 213a, the working electrode reference terminal 213b, the counter electrode terminal 214a and the counter electrode reference terminal 214b.

Note that while the biosensor of the present embodiment includes one working electrode terminal, one working electrode reference terminal, one counter electrode terminal and one counter electrode reference terminal, the present invention is not limited to this, and more of these terminals may alternatively be provided. Specifically, two or more of each of the working electrode terminal, the working electrode reference terminal, the counter electrode terminal and the counter electrode reference terminal may alternatively be provided, and the number of working electrode terminals and the number of counter electrode terminals may be different from each other. Moreover, the number of working electrode terminals and the number of working electrode reference terminals may be different from each other, and the number of counter electrode terminals and the number of counter electrode reference terminals may be different from each other.

Moreover, where one of the working electrode 211 and the counter electrode 212 is a first electrode and the other is a second electrode, the number of terminals for the first electrode (e.g., the working electrode 211) may be one, while the number of terminals for the second electrode (e.g., the counter electrode 212) is more than one. Also with a biosensor having such a structure, it is possible to reduce the current error due to the line resistance over the prior art by using one of the terminals connected to the second electrode for applying a voltage to the second electrode while using another one of the terminals for referencing the voltage at the second electrode.

Twentieth Embodiment

Figure 33:
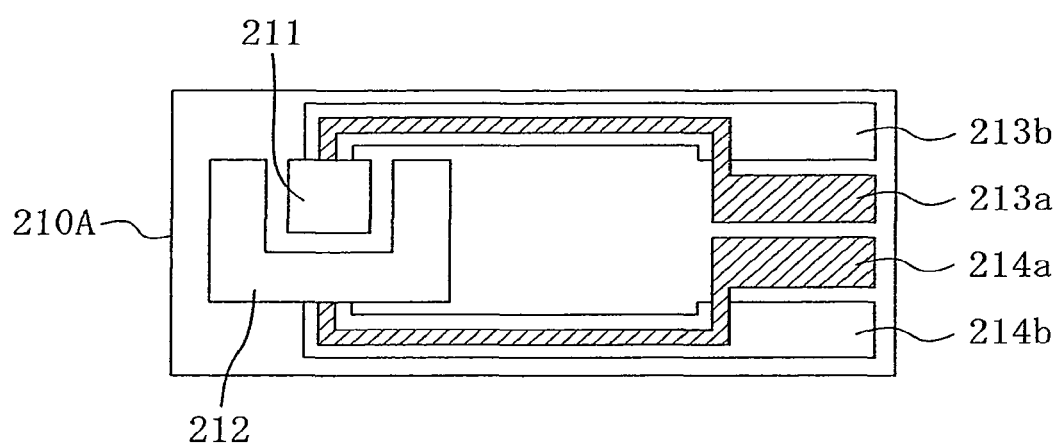
FIG. 33 is a plan view illustrating a biosensor of the twentieth embodiment of the present invention.

FIG. 33 illustrates the structure of a biosensor of the twentieth embodiment of the present invention. A biosensor 210A of the present embodiment is similar to the biosensor 210 of the nineteenth embodiment, except that the electrodes are provided in a multilayered structure. As illustrated in the figure, the working electrode terminal 213a and the working electrode reference terminal 213b are layered over each other (so as to overlap each other as viewed from above), while the counter electrode terminal 214a and the counter electrode reference terminal 214b are layered over each other. In this way, it is possible to reduce the size of the biosensor, and further to reduce the cost thereof.

Note that while the working electrode terminal and the working electrode reference terminal are layered over each other, and the counter electrode terminal and the counter electrode reference terminal are layered over each other, in the present embodiment, the present invention is not limited to this. For example, it is possible to obtain an effect as described above by layering the working electrode terminal and the counter electrode terminal over each other, by layering the working electrode terminal and the counter electrode reference terminal over each other, or by layering the working electrode reference terminal and the counter electrode terminal over each other.

Twenty-First Embodiment

Figure 34:
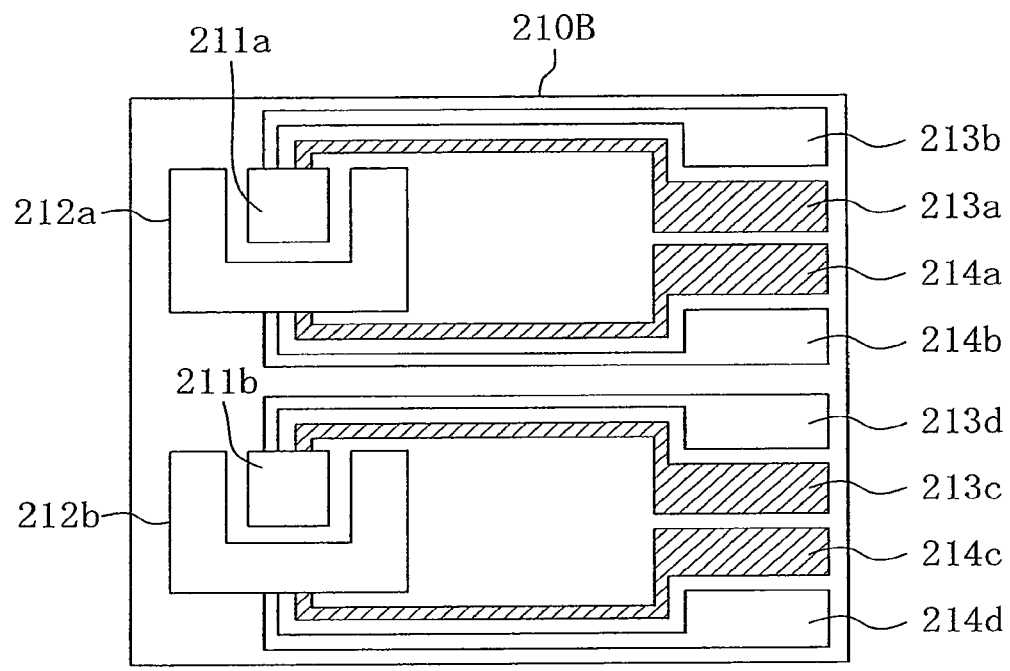
FIG. 34 is a plan view illustrating a biosensor of the twenty-first embodiment of the present invention.

FIG. 34 illustrates the structure of a biosensor of the twenty-first embodiment of the present invention. In a biosensor 210B of the present embodiment, two biosensors 210 of the nineteenth embodiment are formed on the same substrate. Although not shown in the figure, different assay reagents made of enzymes, mediators, etc., corresponding to different assayed chemical substances are applied on the sensor section including the combination of a working electrode 211a and a counter electrode 212a, and on the sensor section including the combination of a working electrode 211b and a counter electrode 212b. Thus, by providing a plurality of sensor sections on the same substrate, it is possible to assay a plurality of chemical substances at once, and it is possible to realize a biosensor of a higher performance and a lower price.

Note that while the biosensor 210B of the present embodiment includes two sensor sections, it may alternatively include three or more sensor sections.

Twenty-Second Embodiment

Figure 35:
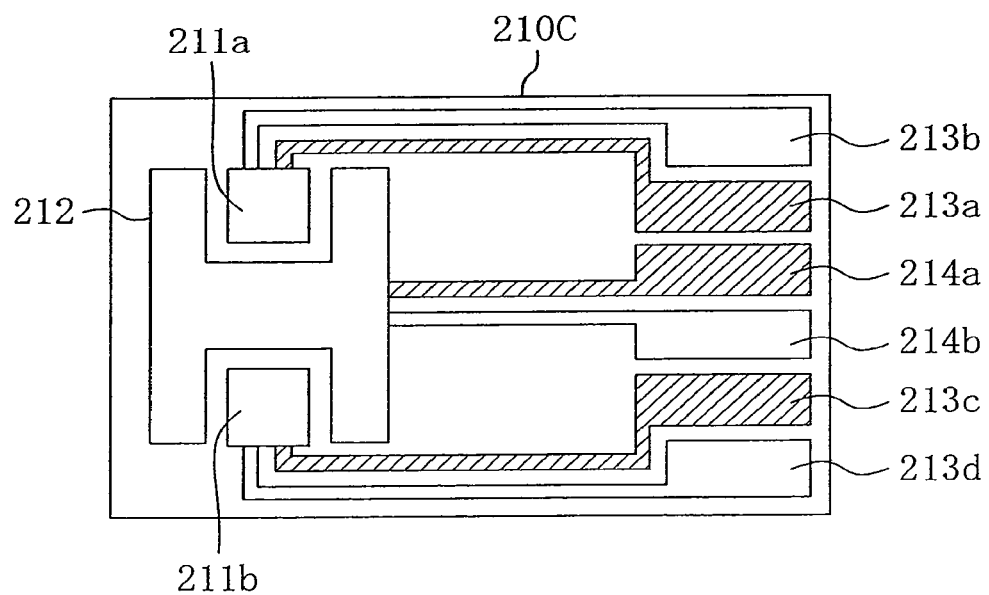
FIG. 35 is a plan view illustrating a biosensor of the twenty-second embodiment of the present invention.

FIG. 35 illustrates the structure of a biosensor of the twenty-second embodiment of the present invention. A biosensor 210C of the present embodiment is similar to the biosensor 210B of the twenty-first embodiment, except that the counter electrodes 212a and 212b are integrated into a single piece. The counter electrode 212 of the biosensor 210C is both for the working electrode 211a and for the working electrode 211b. In other words, the working electrodes 211a and 211b share a single counter electrode 212. Therefore, it is possible to omit a counter electrode terminal 214c and a counter electrode reference terminal 214d in the biosensor 210B, and it is sufficient for the biosensor 210C to include one counter electrode terminal 214a and one counter electrode reference terminal 214b. Thus, it is possible to further reduce the size of the biosensor.

Note that while two working electrode 211a and 211b share a single counter electrode 212 in the present embodiment, three or more working electrodes may be provided in the biosensor, the working electrodes sharing a single counter electrode. Conversely, a plurality of counter electrodes may be provided in the biosensor so as to share a single working electrode.

Twenty-Third Embodiment

Figure 36:
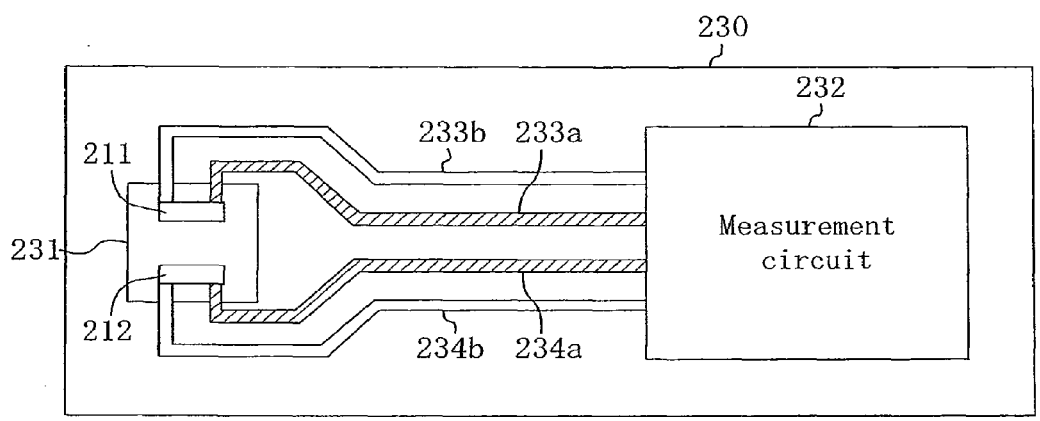
FIG. 36 is a plan view illustrating a biosensor chip of the twenty-third embodiment of the present invention.

FIG. 36 illustrates the structure of a biosensor chip of the twenty-third embodiment of the present invention. A biosensor chip 230 of the present embodiment includes a sensor section 231 and a measurement circuit 232. An assay reagent made of an enzyme, a mediator, etc., according to the assayed chemical substance is applied on the sensor section 231, and as a voltage is applied thereto, the sensor section 231 outputs a current according to the concentration of a particular chemical substance contained in the body fluid such as blood placed thereon. The measurement circuit 232 applies a voltage to the sensor section 231, and measures the output current. Moreover, the sensor section 231 and the measurement circuit 232 are electrically connected to each other by working electrode lines 233a and 233b and the counter electrode lines 234a and 234b.

The portion including the sensor section 231, the working electrode lines 233a and 233b and the counter electrode lines 234a and 234b has a similar structure to that of the biosensor of the nineteenth embodiment. Specifically, the working electrode line 233a and the counter electrode line 234a are used for applying voltages to the working electrode 211 and the counter electrode 212, respectively, whereas the working electrode line 233b and the counter electrode line 234b are used for referencing voltages at the working electrode 211 and the counter electrode 212, respectively. Moreover, the measurement circuit 232 has a similar circuit configuration to those of the measurement circuits 220, 220A, 220B and 220C described in the first to eighteenth embodiments. Thus, the biosensor chip 230 includes a biosensor and a biosensor device of the present invention formed on a single chip.

The working electrode lines 233a and 233b and the counter electrode lines 234a and 234b in the biosensor chip 230 are formed as thin films by a microfabrication process, whereby the resistance values thereof are increased. However, according to the present embodiment, it is possible to measure a current without being influenced by the resistance values, as described above. Therefore, it is possible to realize a biosensor chip that has a high precision and a very small size and is inexpensive.

Note that the substrate on which the biosensor chip 230 is formed may be of any material or structure as long as it is a substrate on which the sensor section 231 and the measurement circuit 232 can be formed, such as a silicon substrate, a silicon-on-insulator substrate, a silicon-on-sapphire substrate, or a glass substrate.

Moreover, where one of the working electrode 211 and the counter electrode 212 is a first electrode and the other is a second electrode, the first voltage application section for applying the first voltage (e.g., the voltage Vp1) to the first line (e.g., the working electrode line 233a) connecting the first electrode (e.g., the working electrode 211) to the measurement circuit 232 is a conventional voltage application section, while the second voltage application section for applying the second voltage (e.g., the voltage Vm1) to the second line (e.g., the counter electrode line 234a) connecting the second electrode (e.g., the counter electrode 212) to the measurement circuit 232 is a voltage application section of the present embodiment (e.g., the counter electrode voltage application section 222 or 222A). The second voltage application section references the third voltage (e.g., the voltage Vm) of the second electrode via the third line (e.g., the counter electrode line 234b) connecting the second electrode to the measurement circuit 232, and generates the second voltage so that the third voltage and a given base voltage (e.g., the voltage Vmr) are matched with each other. Thus, even if one of the working electrode voltage application section 221 or 221A and the counter electrode voltage application section 222 or 222A is omitted in the measurement circuit 232, it is possible to realize a biosensor chip that has a high precision and a very small size and is inexpensive.

Twenty-Fourth Embodiment

Figure 37:
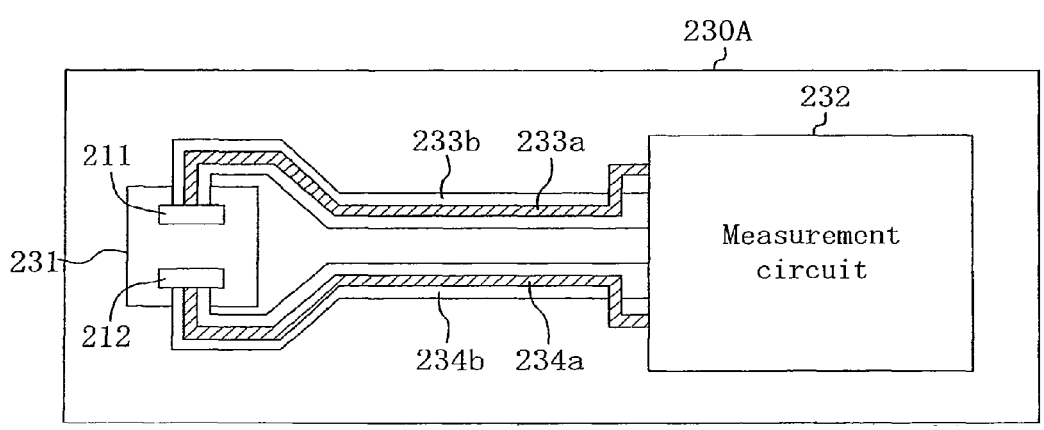
FIG. 37 is a plan view illustrating a biosensor chip of the twenty-fourth embodiment of the present invention.

FIG. 37 illustrates the structure of a biosensor chip of the twenty-fourth embodiment of the present invention. A biosensor chip 230A of the present embodiment is similar to the biosensor chip 230 of the twenty-third embodiment, except that the lines are provided in a layered structure. As illustrated in the figure, the working electrode lines 233a and 233b are layered over each other, while the counter electrode lines 234a and 234b are layered over each other. Thus, it is possible to reduce the size of the biosensor chip, and to reduce the price thereof.

Note that while the working electrode lines are layered over each other, or the counter electrode lines are layered over each other, in the present embodiment, an effect similar to that described above can also be obtained by layering a working electrode line and a counter electrode line over each other.

Twenty-Fifth Embodiment

Figure 38:
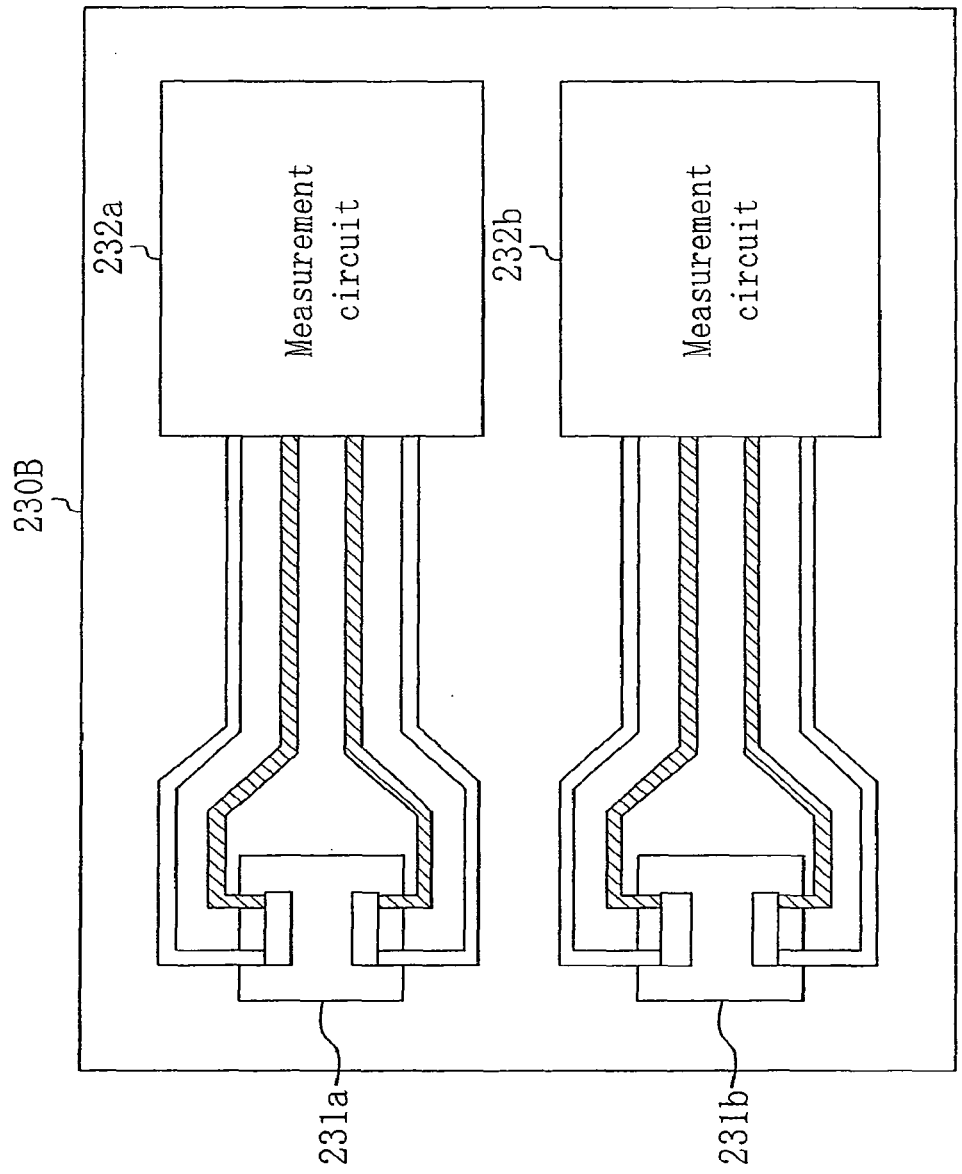
FIG. 38 is a plan view illustrating a biosensor chip of the twenty-fifth embodiment of the present invention.

FIG. 38 illustrates the structure of a biosensor chip of the twenty-fifth embodiment of the present invention. A biosensor chip 230B of the present embodiment is similar to the biosensor chip 230 of the twenty-third embodiment, except that two sensor sections and two measurement circuits are formed on the same substrate. Although not shown in the figure, an assay reagent made of an enzyme, a mediator, etc., corresponding to the assayed chemical substance is applied on a sensor section 231a and a sensor section 231b. Thus, by providing a plurality of sensor sections on the same substrate, it is possible to measure a plurality of chemical substances at once, whereby it is possible to realize a biosensor chip of a higher performance and a lower price.

Note that while two sensor sections are provided in the biosensor chip 230B in the present embodiment, three or more sensor sections may alternatively be provided.

Twenty-Sixth Embodiment

Figure 39:
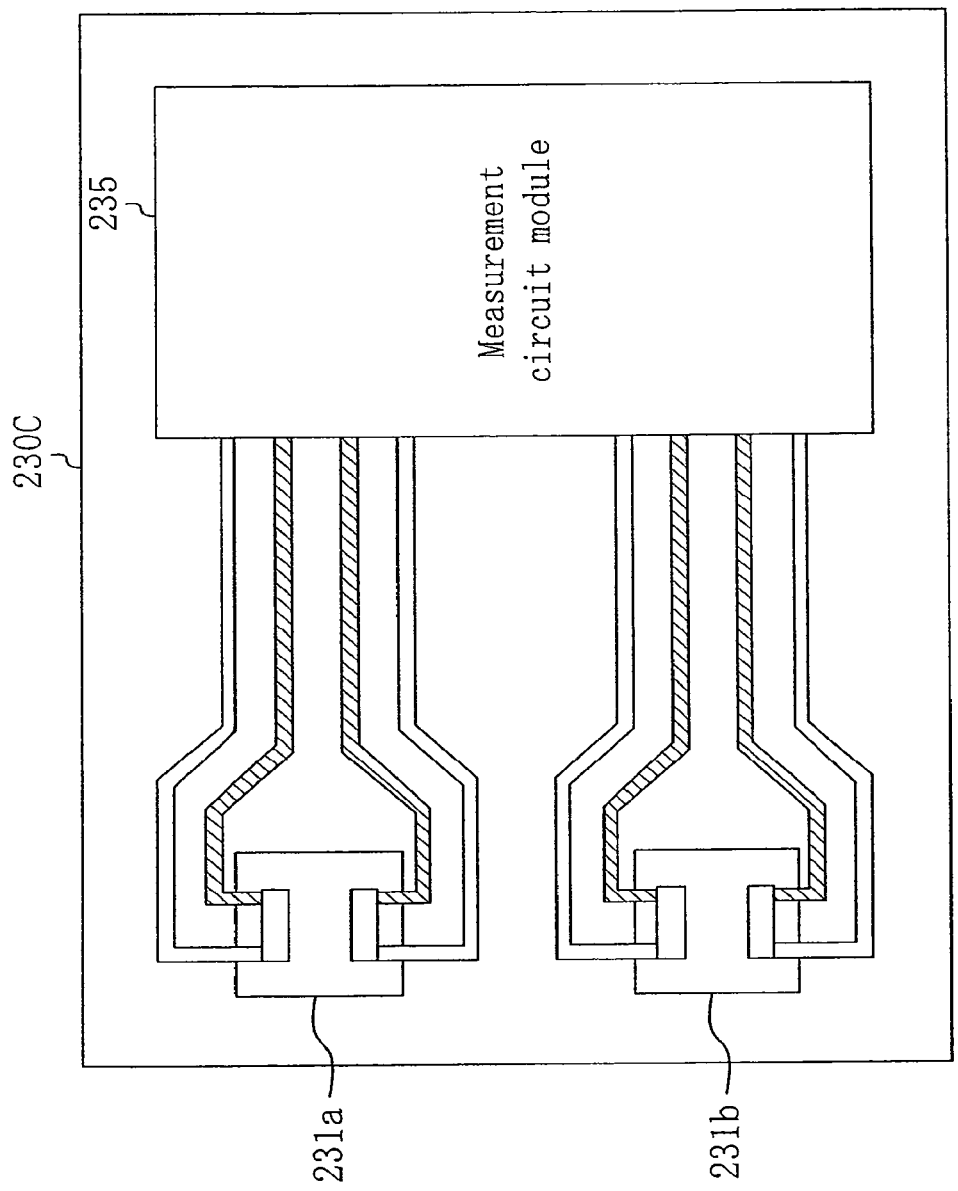
FIG. 39 is a plan view illustrating a biosensor chip of the twenty-sixth embodiment of the present invention.

FIG. 39 illustrates the structure of a biosensor chip of the twenty-sixth embodiment of the present invention. A biosensor chip 230C of the present embodiment is similar to the biosensor chip 230B of the twenty-fifth embodiment, except that measurement circuits 232a and 232b are integrated together into a single measurement circuit module 235.

Figure 40:
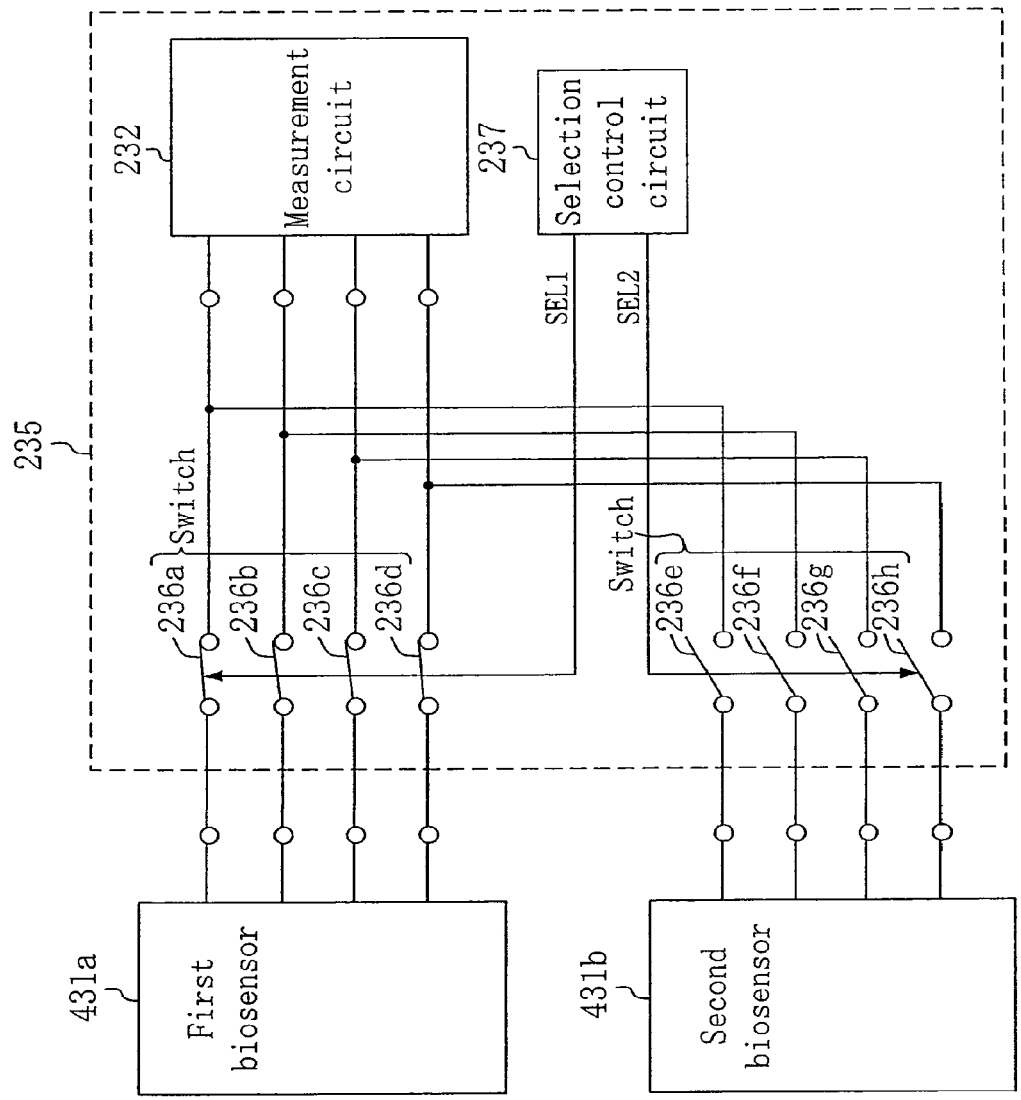
FIG. 40 is a circuit configuration diagram illustrating a measurement circuit module of the twenty-sixth embodiment.

FIG. 40 illustrates the circuit configuration of the measurement circuit module 235. The measurement circuit module 235 includes the measurement circuit 232, switches 236a, 236b, 236c and 236d for turning ON/OFF the connection between a first biosensor 431a and the measurement circuit 232, switches 236e, 236f, 236g and 236h for turning ON/OFF the connection between a second biosensor 431b and the measurement circuit 232, and a selection control circuit 237 for controlling the operation of the switches 236a to 236h. Note that the switches 236a to 236h and the selection control circuit 237 correspond to the "switching means" of the present invention.

The selection control circuit 237 closes/opens all of the switches 236a to 236d by using a control signal SEL1. Moreover, it closes/opens all of the switches 236e to 236h by using a control signal SEL2. Note however that the switches 236a to 236h will not be all closed at the same time. Specifically, the selection control circuit 237 selects one of the first biosensor 431a and the second biosensor 431b, and controls the switches 236a to 236h so that the selected biosensor and the measurement circuit 232 are electrically connected to each other.

By providing the switches 236a to 236h between the biosensors 431a and 431b and the measurement circuit 232, the resistance value increases. However, according to the present invention, it is possible to measure an accurate current level irrespective of the resistance value, as already described above.

As described above, according to the present embodiment, biosensors can be switched to one another, whereby it is possible to reduce the number of measurement circuits to be provided, as compared with the biosensor chip 230B of the twenty-fifth embodiment. Thus, it is possible to further reduce the size of the biosensor chip.

Note that while two control signals SEL1 and SEL2 are used to control the switches 236a to 236h in the present embodiment, the present invention is not limited to this. For example, the switches 236a to 236h may be controlled by using only the control signal SEL1, or the biosensors may be switched to one another by other methods.

Twenty-Seventh Embodiment

Figure 41:
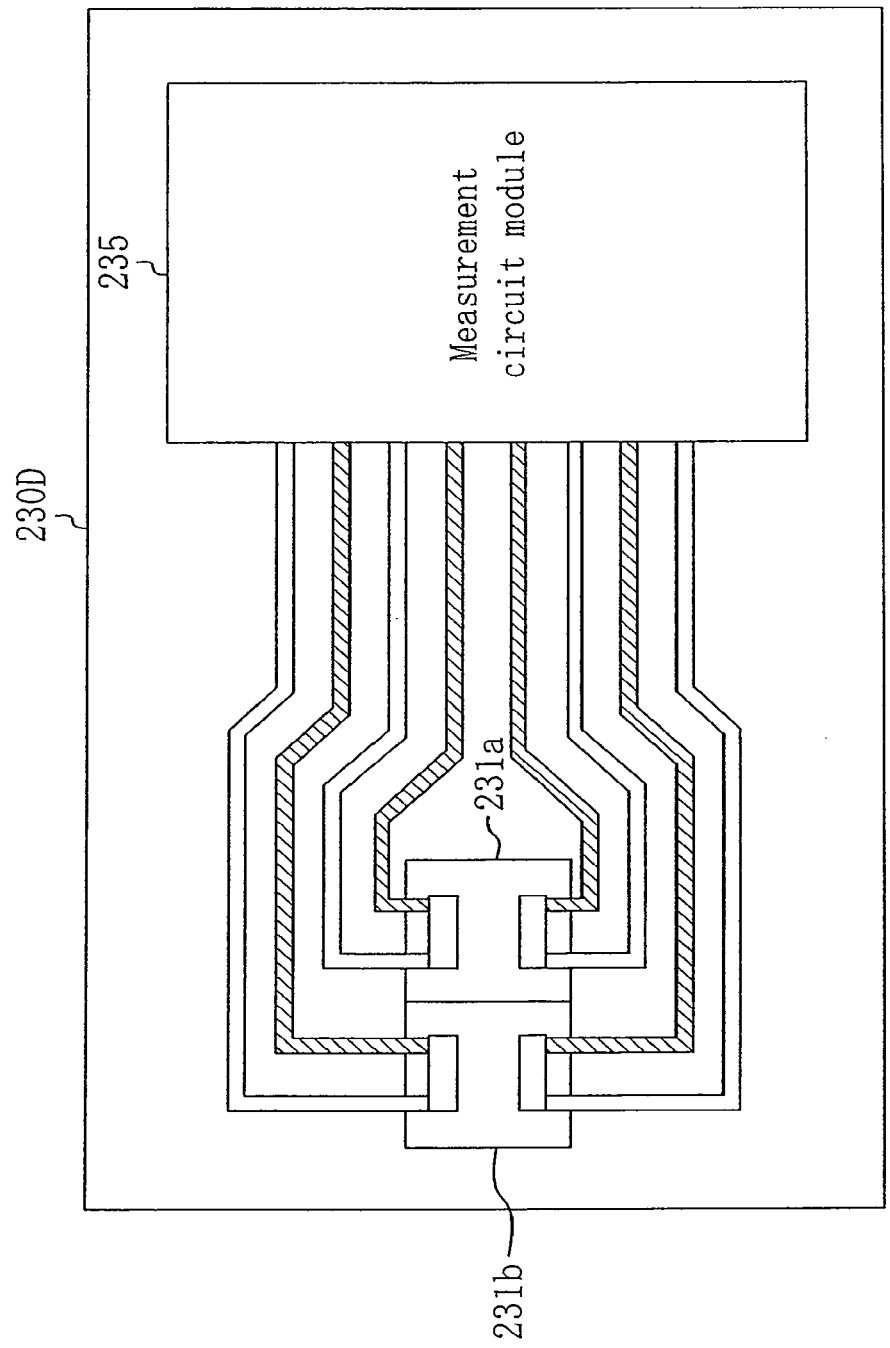
FIG. 41 is a plan view illustrating a biosensor chip of the twenty-seventh embodiment of the present invention.

FIG. 41 illustrates the structure of a biosensor chip of the twenty-seventh embodiment of the present invention. The circuit configuration of a biosensor chip 230D of the present embodiment is similar to that of the biosensor chip 230C of the twenty-sixth embodiment. What is different from the biosensor chip 230C is that the sensor sections 231a and 231b are arranged adjacent to each other. If a plurality of sensor sections 231a and 231b are arranged adjacent to each other, it is possible to analyze a plurality of chemical substances by placing a body fluid sample such as blood only at a single point rather than a plurality of points.

As described above, the present embodiment requires a very small amount of a body fluid sample such as blood, thereby reducing the burden on the patient for blood collection, etc. Moreover, with the sensor sections being adjacent to each other, it is possible to simplify the structure of the section on which the sample is placed.

Note that by arranging the sensor sections adjacent to each other in a biosensor, it is possible to obtain an effect similar to that described above.

Twenty-Eighth Embodiment

Figures 42A, 42B:
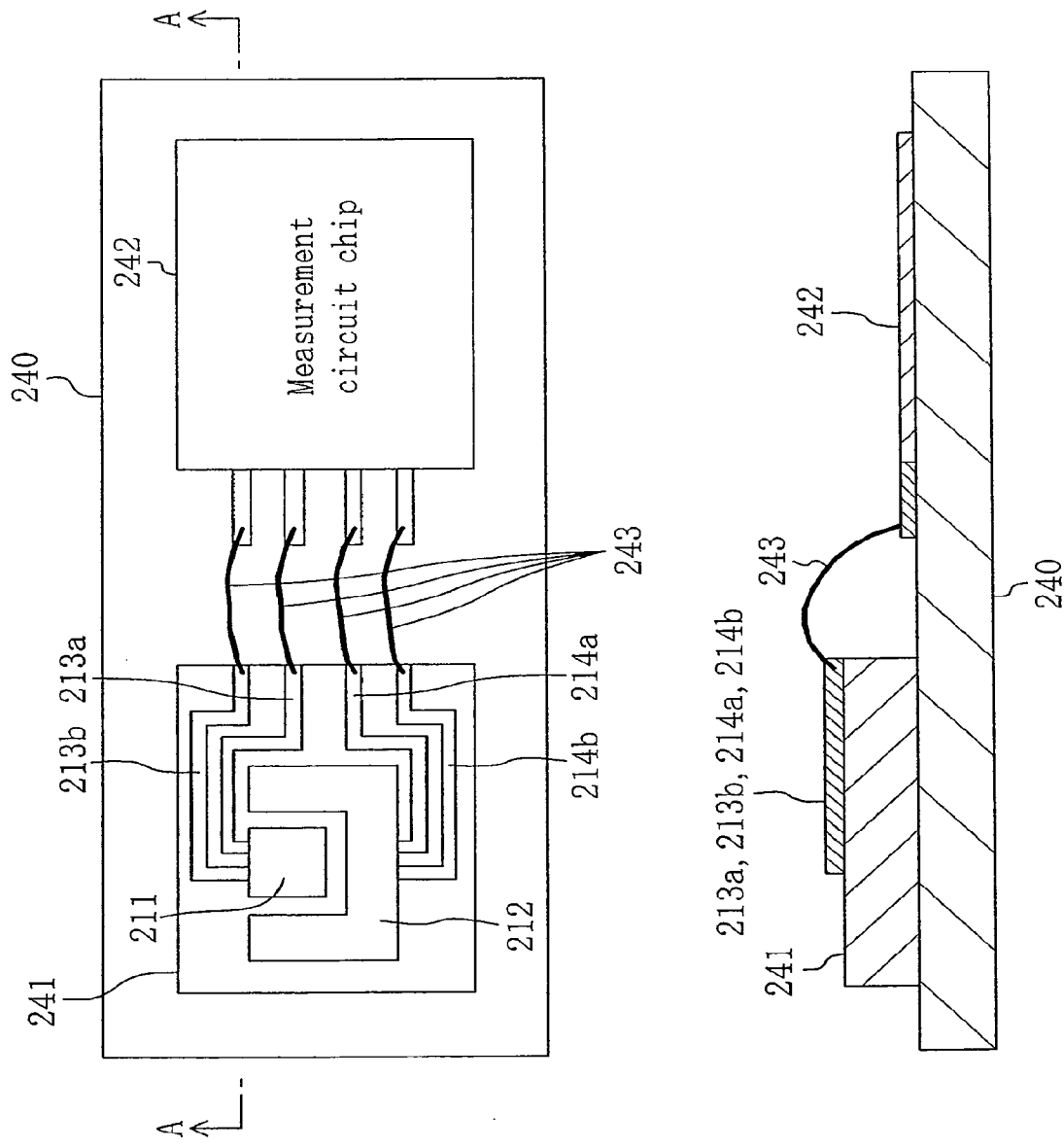
FIG. 42A is a structure diagram illustrating a biosensor chip of the twenty-eighth embodiment of the present invention.
FIG. 42B is a cross-sectional view taken along line A-A in FIG. 42A.
Figure 43:
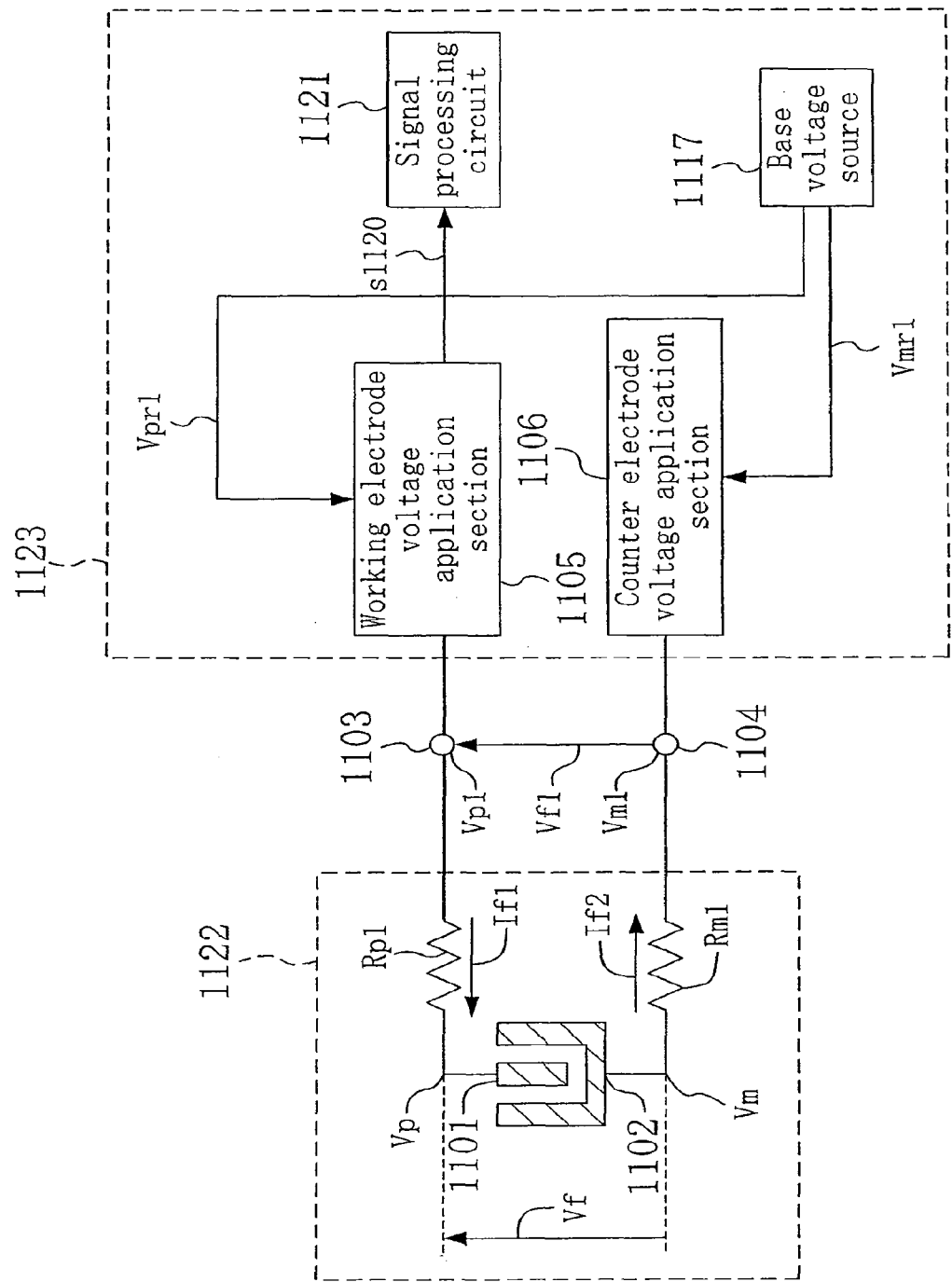
FIG. 43 is a circuit diagram illustrating a portion of a conventional biosensor device.

FIG. 42 illustrates the structure of a biosensor chip of the twenty-eighth embodiment of the present invention. A biosensor chip 240 of the present embodiment is similar to the biosensor chip 230 of the twenty-third embodiment, except that the biosensor chip 240 has a chip-on-chip structure, where a sensor chip 241 and a measurement circuit chip 242 are provided, instead of the sensor section 231 and the measurement circuit 232, respectively, in different semiconductor integrated circuits, with the chips being formed on the same substrate. The working electrode terminal 213a, the working electrode reference terminal 213b, the counter electrode terminal 214a and the counter electrode reference terminal 214b of the sensor chip 241 are electrically connected to the measurement circuit chip 242 via wires 43. Note that FIG. 42(b) is a cross-sectional view taken along line A-A in FIG. 42(a).

In the twenty-third embodiment, if the assay reagent applied on the sensor section 231 in the biosensor chip 230 is not suited for the substrate material on which the measurement circuit chip 242 is formed, i.e., the substrate material of the biosensor chip 230, in terms of the affinity or non-reactiveness, it will be very difficult to from the sensor section 231 and the measurement circuit chip 242 on the same substrate. Moreover, this is also true when the assay reagent is not suited for the working electrode lines 233a and 233b and the counter electrode lines 234a and 234b. However, with the biosensor chip 240 of the present embodiment, the sensor chip 241 and the measurement circuit chip 242 are formed in different semiconductor integrated circuits, whereby such a problem does not occur.

As described above, according to the present embodiment, a biosensor chip is formed in a chip-on-chip structure, whereby it is possible to realize biosensor chips with various assay reagents. This expands the variety of objects that can be assayed by the biosensor chip.

Note that while the sensor chip 241 and the measurement circuit chip 242 are arranged on a support substrate in the present embodiment, the present invention is not limited to this. Alternatively, the support substrate may be omitted, in which case the measurement circuit chip 242 may be arranged directly on the sensor chip 241, or the sensor chip 241 may be arranged directly on the measurement circuit chip 242.

Moreover, while the sensor chip 241 and the measurement circuit chip 242 are connected to each other by the wires 43, they may alternatively be connected to each other by a ball grid array (BGA), or the like, instead of the wires 43.

Moreover, the biosensor chip 240 of the present embodiment is obtained by providing the biosensor chip 230 of the twenty-third embodiment in a chip-on-chip structure, the present invention is not limited to this. For example, the biosensor chips 230A to 230D of the ninth to twenty-seventh embodiments, or biosensor chips of other structures, may be provided in a chip-on-chip structure.

INDUSTRIAL APPLICABILITY

The biosensor device and the biosensor of the present invention can suitably be used for assaying a biological substance, e.g., in a device for assaying the blood glucose level.

The invention claimed is:

1. A method for performing assays of a fluid using a biosensor that comprises a first electrode set including a working electrode and a counter electrode; a working electrode terminal and a first reference terminal that are connected to the working electrode; a counter electrode terminal and a second reference terminal that are connected to the counter electrode; and a second electrode set including two electrodes; wherein the second electrode set is disposed near the first electrode set; the method comprising:
   connecting the biosensor to a measurement circuit;
   performing an assay of the fluid based on a current flowing through the working electrode terminal or the counter electrode terminal;
   controlling a voltage between the working electrode and the counter electrode using a voltage detected by the first reference terminal and a voltage detected by the second reference terminal; and
   performing another assay of the fluid based on a current flowing between the two electrodes of the second electrode set.

2. The method of claim 1, wherein substantially no current flows through the first reference terminal and the second reference terminal during the step of performing the assay based on a current flowing through the working electrode terminal or the counter electrode terminal.

3. The method of claim 1, wherein the assays are different assays.

4. The method of claim 1, wherein the connecting step comprises the steps of:
   connecting the working electrode terminal to a first terminal of the measurement circuit;
   connecting the first reference terminal to a second terminal of the measurement circuit;
   connecting the counter electrode terminal to a third terminal of the measurement circuit; and
   connecting the second reference terminal to a fourth terminal of the measurement circuit;
   wherein the first terminal and the third terminal are located between the second terminal and the fourth terminal.

5. The method of claim 4, wherein:
   the biosensor has two electrode terminals respectively connected to the two electrodes of the second electrode set; and
   the connecting step further comprises connecting the two electrode terminals to a fifth terminal and a sixth terminal of the measurement circuit, respectively, the fifth terminal and the sixth terminal being located between the first terminal and the third terminal.

6. The method of claim 1, wherein in the step of performing the assay of the fluid based on the current flowing through the working electrode terminal or the counter electrode terminal, the measurement circuit uses an amplifier having high input impedance, an input of the amplifier being connected to the first reference terminal.

7. The method of claim 1, wherein in the step of performing the assay of the fluid based on the current flowing through the working electrode terminal or the counter electrode terminal, the measurement circuit uses an amplifier having high input impedance, an input of the amplifier being connected to the second reference terminal.

8. A device configured to be connected to a biosensor that comprises: a first electrode set including a working electrode and a counter electrode; a working electrode terminal and a first reference terminal that are connected to the working electrode; a counter electrode terminal and a second reference terminal that are connected to the counter electrode; and a second electrode set including two electrodes, wherein the second electrode set is disposed near the first electrode set; the device comprising:
- a measurement circuit for performing an assay of a fluid based on a current flowing between the working electrode and the counter electrode and for performing another assay of the fluid based on a current flowing between the two electrodes of the second electrode set, wherein the measurement circuit controls a voltage between the working electrode and the counter electrode using a voltage at the first reference terminal and a voltage at the second reference terminal during the assay performed by the first electrode set.

9. A device configured to be connected to a biosensor that comprises: a first electrode set including a working electrode and a counter electrode; a working electrode terminal and a first reference terminal that are connected to the working electrode; a counter electrode terminal and a second reference terminal that are connected to the counter electrode; and a second electrode set including two electrodes, wherein the second electrode set is disposed near the first electrode set; the device comprising:
- a measurement circuit for performing an assay of a fluid based on a current flowing between the working electrode and the counter electrode and for performing another assay of the fluid based on a current flowing between the two electrodes of the second electrode set;
- a first terminal configured to be connected to the working electrode terminal;
- a second terminal configured to be connected to the first reference terminal;
- a third terminal configured to be connected to the counter electrode terminal; and
- a fourth terminal configured to be connected to the second reference terminal.

10. The device of claim 9, wherein the first terminal and the third terminal are located between the second terminal and the fourth terminal.

11. The device of claim 9, further comprising:
- a fifth terminal configured to be connected to an electrode terminal of the biosensor that is connected to one of the two electrodes of the second electrode set; and
- a sixth terminal configured to be connected to an electrode terminal of the biosensor that is connected to the other one of the two electrodes of the second electrode set.

12. The device of claim 11, wherein the fifth terminal and the sixth terminal are located between the first terminal and the third terminal.

13. The device of claim 9, wherein substantially no current flows through the second terminal and through the fourth terminal during the assay performed by the first electrode set.

14. The device of claim 9, further comprising an amplifier with high input impedance, an input of the amplifier being connected to the second terminal.

15. The device of claim 9, further comprising an amplifier with high input impedance, an input of the amplifier being connected to the fourth terminal.

16. A device configured to be connected to a biosensor that comprises: a first electrode set including a working electrode and a counter electrode; a working electrode terminal and a first reference terminal that are connected to the working electrode; a counter electrode terminal and a second reference terminal that are connected to the counter electrode; and a second electrode set including two electrodes, wherein the second electrode set is disposed near the first electrode set; the device comprising:
- a measurement circuit for performing an assay of a fluid based on a current flowing between the working electrode and the counter electrode and for performing another assay of the fluid based on a current flowing between the two electrodes of the second electrode set; and
- a switch control circuit for controlling connection between the first electrode set and the measurement circuit and for controlling connection between the second electrode set and the measurement circuit.

* * * * *